United States Patent
Fischer et al.

(10) Patent No.: US 7,351,879 B2
(45) Date of Patent: Apr. 1, 2008

(54) COMPOSITIONS AND METHODS FOR MODULATING PLANT DEVELOPMENT

(75) Inventors: Robert Fischer, El Cerrito, CA (US); Tetsu Kinoshita, Shizuoka (JP); Ramin Yadegari, Tucson, AZ (US); Mary Gehring, Berkeley, CA (US); Jack Okamuro, Oak Park, CA (US); Van-Dinh Dang, Oak Park, CA (US)

(73) Assignee: The Regents of the University of California, Oakland, CA (US)

( * ) Notice: Subject to any disclaimer, the term of this patent is extended or adjusted under 35 U.S.C. 154(b) by 275 days.

(21) Appl. No.: 11/051,456

(22) Filed: Feb. 4, 2005

(65) Prior Publication Data

US 2005/0229270 A1 Oct. 13, 2005

Related U.S. Application Data

(63) Continuation of application No. 10/176,884, filed on Jun. 21, 2002, now Pat. No. 6,906,244.

(60) Provisional application No. 60/300,506, filed on Jun. 22, 2001.

(51) Int. Cl.
*C12N 15/29* (2006.01)
*C12N 15/82* (2006.01)
*A01H 5/00* (2006.01)

(52) U.S. Cl. .................... 800/298; 536/24.1; 800/287; 435/320.1

(58) Field of Classification Search ............... 536/24.1; 800/298, 287; 435/320.1
See application file for complete search history.

(56) References Cited

OTHER PUBLICATIONS

Yadegari et al (2000, The Plant Cell 12:2367-2381).*

Chaudhury, et al.,; "Fertilization-independent seed development in *Arabidopsis thaliana*"; 1997, *Proc. Natl. Acad. Sci.*, vol. 94, pp. 4223-4228.

Goodrich, et al.; "A Polycomb-group gene regulates homeotic gene expression in *Arabidopsis*"; 1997, *Nature*, vol. 38616, pp. 44-51.

Grossniklaus, et al.; "Maternal Control of Embryongenesis by MEDEA, A Polycomb Group Gene in *Arabidopsis*"; 1998, *Science*, vol. 280, pp. 446-450.

Gutjahr, et al.; "The Polycomb-group gene, extra sex combs, encodes a nuclear member of the WD-40 repeat family"; 1995, *The EMBO Journal*, vol. 14, No. 17, pp. 4296-4306.

Holtorf, Sonke et al.; "Comparison of different constitutive and inducible promoters for the overexpression of transgenes in *Arabidopsis thaliana*"; 1995, *Plant Mol. Biol.*, vol. 29, pp. 637-646.

Ingram, Richard et al.; "Transgenic Tobacco Plants Expressing the *Drosophila* Polycomb (Pc) Chromodomain Show Developmental Alterations: Possible Role of Pc Chromodomain Proteins in Chromatin-Mediated Gene Regulation in Plants"; 1999, *The Plant Cell*, vol. 11, pp. 1047-1060.

Jenuwein, et al., "SET domain proteins modulate chromatin domains in eu- and heterochromatin", CMLS, Cell. Mol. Life Sci., 54: 80-93 (1998).

Miki, et al.; "Procedures for Introducing Foreign DNA into Plants"; 1993, *Methods in Plants Molecular Biology and Biotechnology*, pp. 67-88.

Ohad, Nir, et al.; "A mutation that allows endosperm development without fertilization"; 1999 *Proc. Natl. Acad. Sci.*, vol. 93, pp. 5319-5324.

Pirrota, V.; "PcG complexes and chromatin silencing"; 1997, *Current Opinion in Genetics & Development*, vol. 7, pp. 249-258.

Van Der Krol, Alexander R. et al.; "Antisense genes in plants: an overview"; 1988, *Gene*, vol. 72, pp. 45-50.

\* cited by examiner

*Primary Examiner*—Stuart F. Baum
(74) *Attorney, Agent, or Firm*—Townsend and Townsend and Crew LLP

(57) ABSTRACT

The present invention provides compositions and methods for modulating plant development by modulating the expression or activity of plant polycomb genes including FIE and MEA.

8 Claims, 1 Drawing Sheet

FIGURE 1

Alignment of Identified and Putative Histone Acetyltransferases

```
GCN5 family
hP/CAP     98   LALIKDGRVIGGICF  (6)  GFIEIVFCAVTSNEQVKGYGTHLPTHLKEYHIKHL  (4)  LTYADEYAIGYF-KKQGFSKEI
hGCN5     546   LALIKDGRVIGGICF  (6)  GFIEIVFCAVTSNEQVKGYGTHLMTHLKEYHIKHM  (4)  LTYADEYAIGYFIKKQGFSKDI
yGcn5p    141   AVIRKPLTVVGGIDY  (6)  EFAEIVFCAISSIEQVRGYGAHLMTHLKDYVRNTS  (4)  LTYADNYAIGYF-KKQGFTKEI
tHatA     149   VILKNKQKVIGGICF  (6)  RFAEVAFLAVTANEQVRGYGTRLMNKFKDHMQKON  (5)  LTYADNFAIGYF-KKQGFTKDH
Consensus       lalikdgrViGGIcf        gF EivFcAvtsnEQVkGYGthLMNhlKeyhikhn         LTYAD yAIGYF KKQGFsKei SAS family (aka MYST)
ySas2         --STMPIGFFSKDLVSY   QQNNIACIILFPPYQRRGLGLLLIEFSYKLSQLEGV   ISGPEVPLSPFGLIGHLK
hTIP60        CKGFHLVGYFSKEKEST   EDYNVACILTLPPYQRRGYGKLLIEFSYELSKVEGK   TSTPEKPLSDLGLLSYRS
dmMOF         -EGSHIVGYFSKEKKSL   ENYNVACIIVLFPHQRKGEGKLLIAFSYELSRKEGV   ISSPEKPLSDLGRLSYRS
yMof          ELGHHLVGYFSKEHESA   DGYNVACILTLPCYQRVGYGVLLIEFSYELSKKENK   VSSPEKPLSDLGLLSYRA
spYD6D        GQECXVIGYFSKEKRSA   SDYNVSCILTLPIYQRRGYGVFLIDFSYLLTQVEGK   LSSPEKPLSDLGLVTYRS
hMOZ          VKGOHLVGYFSKEHHCQ   QKANVSCIKTLPCYQRKGYGFFLIDFSYLLSKREGQ   AGSPEKPLSDLGRLSYMA
ySas3         AAKPHFVGYFSKEHPNS   NDYNLSCILTLFIYQPKGYGQFLMEFSYLLSRKESK   FGTPEKPLSDLGLLTYPT
ceR07B5.6     DIECHPAGYFSKEHYEP   DVNNISCIHTLPCYGEKGLGFRLILISYALSRKEKH   FSGPEQPLSELGRKALGG
Consensus      g hivGyFSKek s      yNV CIltlP yQrrGyGk LiefSY LekkEg       gtPEkPLSdlGlleYr yKL087    448   YEPDEKDILIGUTRL  (27)  GSVVPLHSRDPRKFPHQGEGTLUMEBAERIAKEEH  (5)  SVISGVGVRNYYGKLGYELDG
yHat1p    179   LLNKETKELIGFVTT  (19)  FRAKISQFLIFPPYENKGHGSCLYBAIIQSWLELK  (14)  DDLRDRNDIQRLRKLGYDAVF
YOR109          HPCYELKRLSNGSF         YSSD---SDLTSTLHRGVGQHSLST--DTYEEEY YPR193c                                --IYINDLYVDENSPVKGAGGKLIQFVYDELDKLG            T
YBH6       32   AFDTETGDAIGPA-HY (10)  EVVNHNDIAYTERARVKGVGRKLIEFVYSPADELG  (7)  TDHYNHRAQLLYTKVAYKTDK
YMR069w         MLTEETGLVEGDALHE (3)   PVIYLYEVHVASAHRGHGIGPRLLEHALCDG
ySpt10                                 VVTGTFLVN-AGI-RGKGIGKTLMETFIEWSKKLG
spATS1                                 VGIYLEDLYVRPQFRGKGIGSYDLSKLARESLRI
Concensus                              -viyi dlyv   RgkGvGrkLiefv ea klg
```

COMPOSITIONS AND METHODS FOR MODULATING PLANT DEVELOPMENT

CROSS-REFERENCES TO RELATED APPLICATIONS

The present application claims priority to U.S. patent application Ser. No. 10/176,884, filed Jun. 21, 2002 and issued as U.S. Pat. No. 6,906,244, which claims priority to U.S. Patent Application No. 60/300,506, filed Jun. 22, 2001.

STATEMENT AS TO RIGHTS TO INVENTIONS MADE UNDER FEDERALLY SPONSORED RESEARCH AND DEVELOPMENT

This invention was made with Government support under Grant No. 2000-01539, awarded by the United States Department of Agriculture. The government has certain rights in this invention.

BACKGROUND OF THE INVENTION

The life cycle and body plan of flowering plants differs from that of invertebrate and vertebrate animal. During animal embryogenesis, a smaller version of the adult is generated with a full complement of nearly complete organs and germ line. Plant embryos establish only the basic root-shoot axis, a cotyledon storage organ(s), and stem cell populations, called the root and shoot apical meristems, that continuously generate new organs throughout post-embryonic development. In *Arabidopsis*, the seedling shoot apical meristem produces the vegetative stem and leaves of the plant. In response to genetic and environmental information, the shoot apical meristem undergoes a dramatic transition, enters the reproductive phase, and becomes the primary inflorescence meristem. See, e.g., M. Koornneef, et al., *Annu. Rev. of Plant Physiol. Plant Mol. Biol.* 49, 345-370 (1998); Y. Y. Levy & C. Dean, *Plant Cell* 10, 1973-1998 (1998); M. Pineiro & G. Coupland, *Plant Physiol.* 117, 1-8 (1998); T. Araki, *Curr Opinion in Plant Biology* 4, 63-68 (2001).

During the early reproductive phase, the inflorescence meristem generates secondary inflorescence meristems subtended by specialized cauline leaves. During the late reproductive phase, solitary flowers are formed composed of sepals, petals, stamens bearing male gametophytes, and carpels bearing female gametophytes. See E. A. Schultz, et al., *Development* 119, 745-765 (1993). Fertilization of the egg by one sperm produces the embryo, whereas fertilization of the adjacent central cell by a second sperm produces the endosperm, an organ that nutritionally supports the development of the embryo with the seed.

Polycomb proteins are essential regulators of animal embryogenesis. See V. Pirrotta, *Cell* 93, 333-336 (1998). They have evolved to control different processes depending upon the distinct life cycle and body plan of the organism. In *Drosophila* and mouse, polycomb proteins are responsible for the long-term repression of homeotic genes. This repression ensures that each body segment bears a distinct array of homeotic transcription factors which determine its identity. During *Caenorhabditis* embryogenesis, polycomb proteins are required to establish the germ line. The WD-motif polycomb proteins, as exemplified by the related *Drosophila* ESC(S. S. Sathe, et al., *Mech. Dev.* 52, 77-87 (1995)), mouse EED (A. Schumacher, et al. *Nature* 383, 250-253 (1996)), and *Caenorhabditis* MES6 proteins (I. Korf, et al., *Development* 125, 2469-2478 (1998)), play an essential role in polycomb complex assembly. The WD repeats form surface loops that are used as scaffolds for the generation of protein complexes including additional polycomb proteins (e.g., SET-domain polycombs) and histone deacetylase that remodel chromatin and repress gene transcription (J. van der Vlag, et al., *Nat. Genet.* 23, 474-478 (1999); F. Tie, et al., *Development* 128, 275-266 (2001)).

Polycomb proteins are also important for plant reproduction (Pirrotta, supra). *Arabidopsis* FIE (FERTILIZATION INDEPENDENT ENDOSPERM) is a WD-motif polycomb related to ESC, EED, and MES6 (N. Ohad, et al., *Plant Cell* 11, 407-415 (1999)). Prior to fertilization, FIE prevents the premature replication of the central cell to form an endosperm, and after fertilization, the maternal FIE allele is essential for seed viability (R. Vinkenoog, et al., *Plant Cell* 12, 2271-2282 (2000); N. Ohad, et al., *Proc. Natl. Acad. Sci. USA* 93, 5319-5324 (1996)). Because maternal mutant fie alleles are not transmitted to the next generation, it has not been possible to generate and examine the phenotype of homozygous fie mutant seedlings or plants (Ohad, 1996, supra; Ohad, 1999, supra; A. M. Chaudhury, et al., *Proc. Natl. Acad. Sci. USA* 94, 4223-4228 (1997)). The Arabadopsis polycomb gene, MEDEA (MEA), contains a SET domain with homology to the *Drosophila* polycomb gene enhancer of zeste (E(z)) (Grossniklaus, et al., *Science* 280, 446-450 (1998)). The MEA gene product interacts with FIE.

Thus, the extent that polycomb gene complexes regulate post-embryonic plant development is not known. The present invention addresses this and other problems.

BRIEF SUMMARY OF THE INVENTION

The present invention provides methods for modulation of development in a plant by modulation of a plant polycomb gene product, such as FIE or MEA, in a non-endosperm tissue in a plant.

In some aspects, the plant polycomb gene product is at least 80% identical to SEQ ID NO:2 or SEQ ID NO:14. In some aspects of the invention, the plant polycomb gene product is SEQ ID NO:2 or SEQ ID NO:14.

In some aspects, activity of the FIE polypeptide is sufficient for the plant to produce viable seed.

In some aspects of the invention, the method includes introducing into a plant an expression cassette, the expression cassette comprising a promoter operably linked to the polynucleotide, or its complement, encoding a plant polycomb gene product.

In some embodiments the expression cassette encodes a plant polycomb gene product at least 80% identical to SEQ ID NO:2 or SEQ ID NO:14. In some embodiments the plant polycomb gene product is a FIE polypeptide (SEQ ID NO:2) or a MEA polypeptide (SEQ ID NO:14).

In some aspects, the expression cassette is an antisense expression cassette, the antisense expression cassette comprising a promoter operably linked to the complement of the polynucleotide encoding a polypeptide least 80% identical to (SEQ ID NOS:2 or 14, respectively). In some aspects of the invention, the polypeptide is identical to SEQ ID NO:2 or SEQ ID NO:14.

In some aspects of the invention, the promoter can be, for example tissue-specific or inducible.

In some aspects, the promoter comprises a polynucleotide at least 50% identical to SEQ ID NO:3. In some aspects, the promoter comprises a polynucleotide at least 50% identical to SEQ ID NO:3. In some aspects of the invention, the promoter comprises a polynucleotide selected from the group consisting of SEQ ID NO:4, SEQ ID NO:5 and SEQ ID NO:6.

In some aspects of the invention, the plant is homozygous for a mutation in a polynucleotide encoding a polypeptide at least 80% identical to SEQ ID NO:2 or SEQ ID NO:14.

In some aspects of the invention, the plant is characterized by:

(a) modulated root development compared to a naturally occurring plant;

(b) ectopic expression of a seed or embryo gene product;

(c) modulated timing of transition from vegetative to reproductive development compared to a naturally occurring plant;

(d) modulated expression of a floral meristem identity gene product compared to a naturally occurring plant;

(e) modulated cotyledon development compared to a naturally occurring plant;

(f) modulated hypocotyl development compared to a naturally occurring plant;

(g) modulated leaf development compared to a naturally occurring plant;

(h) modulated petiole development compared to a naturally occurring plant;

(i) modulated shoot development compared to a naturally occurring plant; or (j) ectopic shoot formation.

For example, the floral meristem identity gene product can be selected from the group consisting of LEAFY, APETALA1 APETTALLA1, APETALA3 APETTALLA3, PISTILLATA and AGAMOUS.

In some embodiments of the invention, the activity is modulated by modulating histone acetylation in a cell. For example, a FIE/HAT fusion peptide or MEA/HAT fusion peptide can be expressed in the plant. Examples of FIE/HAT and MEA/HAT fusion peptides include, but are not limited to, SEQ ID NOS:8 and 16, respectively.

The present invention also provides an isolated nucleic acid molecule comprising a polynucleotide selected from the group consisting of SEQ ID NO:4, SEQ ID NO:5 and SEQ ID NO:6.

BRIEF DESCRIPTION OF THE DRAWINGS

FIG. 1: Alignment of identified and putative histone acetyltransferase (HAT) functional domains (SEQ ID NOS: 45-54, 59-66 and 73-89). Consensus HAT functional domain sequences =SEQ ID NOS:45, 55-58, 67-72 and 89-91. Specifically, for the GCN5 family of HAT functional domains. SEQ ID NOs:45 refers to amino acids 98-113 of hP/CAF. SEQ ID NOs:46 and 47 refer to the next two segments shown for hP/CAF, 35 and 21 amino acids, respectively. SEQ ID NO:48 refers to the last 22 amino acid segment depicted for hGCN5. SEQ ID NOs:49-51 describe the three segments depicted for yGcn5p, of 15, 35, and 21 amino acids, respectively. Similarly, SEQ ID NOs:52-54 describe the three segments shown for tHatA. The consensus sequences for the GCN5 family of HAT functional domains are described by SEQ ID NOs:55-58 as follows: SEQ ID NO:55 represents the 32 amino acid fragment starting with EIV; SEQ ID NO:56 refers to the next 5 amino acid fragment, SEQ ID NO:57 refers to the next 6 amino acid fragment, and SEQ ID NO:58 refers to the last 9 amino acids shown for the consensus sequence.

Regarding the SAS family of HAT functional domains, SEQ ID NOs:59-66 describe the entire length of the sequences shown for ySas2, hTIP60, dmMOF, yMof, spYD6D, hMOZ, ySas3, and ceR07B5.8. The consensus sequences for this family are depicted in SEQ ID NOs:67-72. SEQ ID NO:67 refers to the 10 amino acid consensus sequence in the first segment, starting with HIV. SEQ ID NO:68 refers to the 6 amino acid consensus sequence in the second segment, starting with CIL. SEQ ID NO:69 refers to the next fragment of 8 amino acids, SEQ ID NO:70 refers to the next amino acid fragment of 6 amino acids, and SEQ ID NO:71 describes the next 6 amino acid fragment. SEQ ID NO:72 describes the last segment of 16 amino acids.

The next set of HAT functional domains is described in SEQ ID NOs:73-91. SEQ ID NOs:73-75 refer to the three segments of yKL087 of 15, 35, and 21 amino acids, respectively. SEQ ID NOs:76-78 refer to the three segments shown for yHat1p of 15, 35, and 21 amino acids, respectively. SEQ ID NOs:79 and 80 describe the segments shown for YOR109 of 15 and 30 amino acids. SEQ ID NO 81 refers to the entire length of YPR193. SEQ ID NOs:82-84 describe the three segments shown for YEH6 of 15, 35, and 21 amino acids respectively. SEQ ID NOs:85 and 86 refer to the two segments shown for YMR069w. SEQ ID NOs:87 and 88 refer to the entire lengths of ySpt10 and spATS1. The consensus sequence for the last group of HAT functional domains are listed as SEQ ID NOs:89-91, with SEQ ID NO:89=VIYI, SEQ ID NO:90=DLYV, and SEQ ID NO:91=RGKGVGRKLIEFV.

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like. In contrast, a polynucleotide sequence or polypeptide sequence "endogenous" to a plant refers to a native sequence which is introduced into the plant, or a predecessor generation of the plant, by a sexual cross and that is not a transgenic or other synthetic sequence. Of course, standard genetic manipulations of plants (e.g., by crossing non-transgenic plants).

The phrase "host cell" refers to a cell from any organism. Preferred host cells are derived from plants, bacteria, yeast, fungi, insects or other animals. Methods for introducing polynucleotide sequences into various types of host cells are well known in the art.

The "biological activity of a polypeptide" refers to any molecular activity or phenotype that is caused by the polypeptide. The "activity of FIE", "activity of MEA", "activity of a polypeptide related to SEQ ID NO:2" or the "activity of a polypeptide related to SEQ ID NO:14" includes the ability to modulate plant development, including (1) plant endosperm production (see, e.g., Ohad et al. *Plant Cell* 11:407-415 (1999); U.S. Pat. No. 6,229,064), (2) timing of transition from vegetative to reproductive structures (3) root development and (4) expression of embryonic and seed-specific genes, including seed storage proteins, in vegetative tissues.

The phrase "floral meristem identity gene product" refers to a gene product that promotes conversion of a shoot meristem to a floral meristem and/or modulates the identity of floral organs in a plant. Expression of a floral meristem identity gene product such as APETALA1 (AP1), CAULIFLOWER (CAL) or LEAFY (LFY) ((D. Weigel, et al., *Nature* 377:495-500 (1995); M. A. Mandel, et al., *Nature* 377:522-524 (1995); Kempin, et al., *Science* 1267(5197): 522-5 (1995)) in shoot meristem can convert shoot meristem to floral meristem in a plant. Additional floral meristem identity gene products include, for instance, AGAMOUS (AG), APETTALA3 (AP3), and PISTILLATA (PI) (G. Parcy, et al., *Nature* 395:561-566 (1998)) and SEP1, SEP2, and SEP3 (Pelaz, et al., *Nature* 405:200-203 (2000)). While all of the gene products described above were originally derived from *Arabidopsis*, those of skill in the art will recognize that orthologous gene products from a variety of plant species, as well as variants substantially identical to such gene products, are known or can be isolated using routine molecular biology techniques.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

A "polycomb group gene" is a member of a group of genes whose gene products include transcriptional repressors. See, e.g., Francis and Kingston, *Nature Reviews*, 2:409-421(2001); Gutjahr et al., *EMBO J.* 14:4296-4306 (1995). Gene products of polycomb group genes play a role in gene silencing, acting to remodel chromatin and thus altering accessibility of DNA to the factors required for gene transcription. The designation "polycomb group gene" refers to nucleic acid sequences that are homologous to gene products involved in the zygotic development of the anterior-posterior axis. Polycomb group gene products have been identified in a number of species including *Drosophila*, mice and plants.

Eleven polycomb gene groups have been described based on protein structure (Francis and Kingston, *Nature Reviews* 2:409-421 (2001)). See Table 1.

TABLE 1

List of Polycomb Group gene products

| Gene | Complex | Protein domain(s) |
|---|---|---|
| polycomb | PRC1 | Carboxy-terminal domain; chromodomain |
| polyhomeotic | PRC1 | SPM, H1, zinc finger |
| posterior sex combs | PRC1 | Homology region = RING (zinc finger) + helix-turn-helix |
| dring | PRC1 | RING |
| sex comb on midleg | PRC1 (small fraction only) | SPM |
| enhancer of zeste | E(z)/Esc | SET |
| extra sex combs | E(z)/Esc | WD40 repeats |
| additional sex combs | | |
| super sex combs | | |
| multi sex combs | | |
| polycomb-like cramped | | PHD fingers |
| pleiohomeotic sex comb extra | | Zinc fingers |
| enhancer or polycomb | Yeast homologue present in NuA4 HAT complex | |
| suppressor of zeste 2 | | HR region (shared with Pscc) |

Examples of known polycomb genes can be found in Table 2.

TABLE 2

Polycomb Group Subunits

| Genes | Species | GI number-Source |
| --- | --- | --- |
| Additional sex combs (Asx) | Drosophila | GI: 3292939 |
| Bmi-1 | mouse | GI: 115066 |
| Curly leaf (CLF) | Arabidopsis | GI: 179919 |
| Cramped | Drosophila | GI: 5869804 |
| Enhancer of Zeste (E(z)) | Drosophila | GI: 404864 |
| Enhancer of polycomb | Drosophila | GI: 3757890 |
| Extra sex combs (Esc) | Drosophila | GI: 2133657 or GI: 1050997 |
| FIE | Arabidopsis | GI: 4567095 |
| FIS2 | Arabidopsis | GI: 4185501 |
| MEA | Arabidopsis | GI: 3089625 |
| Mel-18 | mouse | GI: 126937 |
| Multi sex combs (mxc) | Drosophila | GI: 6746602 |
| Pleiohomeotic (pho) | Drosophila | GI: 3258627 |
| Polycomb (Pc) | Drosophila | GI: 129718 |
| Polycomb-like (Pcl) | Drosophila | GI: 521181 |
| Polyhomeotic distal | mouse | GI: 1490546 |
| Polyhomeotic proximal (php) | Drosophila | GI: 730323 |
| Posterior sexcombs (Psc) | Drosophila | GI: 548613 or GI: 103177 |
| Sexcomb extra (Sce) | Drosophila | |
| Sex comb on midleg (Scm) | Drosophila | GI: 1293574 |
| Suppressor-2 of zeste | Drosophila | GI: 236137 (partial) |
| Su(z)2(D) | Drosophila | |
| Super sex combs (sxc) | Drosophila | |

In some embodiments, the polycomb group gene products comprise a WD or SET domain. See, e.g., Ng, et al. *Mol. Cell. Biol.* 17:6663-6672 (1997); Sondek, et al. *Nature* 379:369-374 (1996). An exemplary SET domain is (SEQ ID NO:19)
SDVHGWGAFTWDSLKKNEYLGEYTGELITHDEANERGRIEDRIGSSYLFT

LNDQLEIDARRKGNEFKFLNHSARPNCYAKLMIVRGDQRIGLFAERAIEE

GEELFFDYCYGPEHA.

WD domains are approximately 40 amino acids bordered by a Trp-Asp (WD). WD-repeat-containing proteins typically contain at least three copies of a WD-repeat (tryptophan-aspartate repeat), and sometimes comprise at least 4, 5, 6 or more repeats. The sequence motif that encodes a structural repeat is typically about 25-35 amino acids and sometimes about 30-32 and sometimes 31 amino acids long,. This repeat is described by the following profile, where x is any amino acid:

(G/A) H x x x (V/I) x x (V/L/I/C) x (F/W/L/I/V) x x [0-2] (P?S/D) (DIN/S) (G/S/P) [0-3] x (L/I/V/F) (A/V/L/I) (S/T) (G/A/S/C) (S/G/A) x D x (T/S) (I/V/L/A) (K/R) (V/L/I) (W/F/Y) (D/N).

The number in bracets represent the number of preceding amino acids can occur. Amino acids in parentheses represent different options at that position, with the first residue the most common. In the *Arabadopsis* FIE (SEQ ID NO:2), residues 317-364 encompass a WD40 repeat.

Exemplary polycomb group gene products of the invention include, e.g., the proteins substantially identical to polypeptide encoded by the *Arabidopsis* Mea, FIS2, FIE, E(z), CLF, or TSO1-like genes or homologs thereof.

A "FIE nucleic acid" and "FIE polynucleotide sequence" of the invention is a subsequence or full length polynucleotide sequence of a gene that encodes a polypeptide involved in organ development, which, when the maternal allele is mutated, allows for increased production of the endosperm and/or abortion of the embryo, and which acts as a repressor of transcription. Exemplary FIE polynucleotides encode polypeptides substantially identical to SEQ ID NO:2, and include the nucleic acid sequence displayed in SEQ ID NO:1. FIE polypeptides have at least one FIE activity described herein.

FIE nucleic acids are members of a new class of plant regulatory genes that encode polypeptides with sequence identity to members of the polycomb group genes first identified in *Drosophila*. Polycomb group gene products and their homologues in other species are responsible for repression of homeotic genes. The proteins are a heterogenous group that interact with each other to form large complexes that bind DNA and thereby control gene expression. For a review of polycomb complex genes, see, Pirrotta *Cur. Op. Genet. Dev.* 7:249-258 (1997). Eleven groups of polycomb genes have been identified. FIE (e.g., SEQ ID NO:1) is related to the group encoding proteins comprising WD40 repeats (see, Gutjahr et al. *EMBO J.* 14:4296-4306 (1995).

"MEA nucleic acid" and "MEA polynucleotide sequence" of the invention is a subsequence or full length polynucleotide sequence of the gene that encodes a polypeptide involved in plant organ development. MEA nucleic acids are members of a class of plant regulatory genes that have sequence identity to the polycomb group genes encoding proteins containing a SET domain, e.g., *Drosophila* E(z) (Grossniklaus, et al., Science 280, 446-450 (1998)). Exemplary MEA polynucleotides encode polypeptides substantially identical to SEQ ID NO:14. MEA polypeptides have at least one MEA activity described herein.

FIE and MEA polynucleotides are defined by their ability to hybridize under defined conditions to the exemplified nucleic acids or PCR products derived from them. A FIE or MEA polynucleotides are typically at least about 30-40 nucleotides to about 3,000, usually less than about 5,000 nucleotides in length. The nucleic acids contain coding sequence of from about 100 to about 2000 nucleotides, often from about 500 to about 1700 nucleotides in length.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the terms polycomb nucleic acid, FIE nucleic acid, and MEA nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "polycomb nucleic acid, FIE nucleic acid, and MEA nucleic acid". In addition, the term specifically includes those sequences substantially identical (determined as described below) with a FIE or MEA polynucleotide sequence disclosed here and that encode polypeptides that are either mutants of wild type FIE or MEA polypeptides or retain the biological activity of the FIE or MEA polypeptide (e.g., resulting from conservative substitutions of amino acids in the FIE or MEA polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. Accordingly, polycomb sequences of the invention include nucleic acid sequences that have substantial identity to SEQ ID NO:1, or encodes SEQ ID NO:14 SEQ ID NO:17.

Polycomb polypeptide sequences of the invention include polypeptide sequences having substantial identify to SEQ ID NO:2, or SEQ ID NO:14. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means sequence identity of at least 40%. Percent identity can be determined by comparison to a reference sequence using the programs described herein; preferably BLAST using standard parameters, as described below. This definition also refers to the complement of a test sequence, when the test sequence has substantial identity to a reference sequence. Preferred percent identity of polypeptides can be any integer from 40% to 100%. More preferred embodiments include at least 50%, 55%, 60%, 65%, 70%, 75%, 80%, 85%, 90%, 95%, or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information's website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength. (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 55° C., 60° C. and sometimes 65° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising polycomb nucleic acids such as FIE or MEA nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION OF THE INVENTION

The present invention provides methods for modulating plant development and provides plants and other compositions with modulated development. The invention also provides compositions useful for generating such plants. The invention is based, in part, on the discovery that modulation of expression or activity of polycomb genes such as FIE or MEA in a plant results in plants with modulated development.

The FIE and MEA polycomb proteins are required for proper temporal and spatial patterns of plant development. As demonstrated below, interference with either FIE or MEA activity modulates various phenotypes. Moreover, MEA and FIE physically interact. In fie mutant seedlings, shoots and floral-like organs appear in novel, and botanically inappropriate, positions along the hypocotyl and root. Thus, the present invention provides for methods of modulating the initiation of shoot and reproductive organs in a plant. The shoot apical meristem of *Arabidopsis* fie mutant seedlings prematurely flower, and elevated transcription of floral-promoting genes occur in the embryo and seedling. Thus, FIE plays an essential role during embryo and seedling development to restrict shoot and organ formation to the shoot apical meristem and to repress the transition of the shoot apical meristem from the vegetative to the reproductive state. In addition, the timing of reproductive development (e.g., time to flower) can be modulated by modulating FIE activity. For example, reducing the expression of FIE in a plant results in accelerated time to flowering. Alternatively, time of reproductive development can be delayed by increasing expression (including ectopic expression) of FIE compared to wild type levels. Similarly, the above-listed activities can be modulated by modulating the activity of MEA or other polycomb group gene products in a plant The LFY transcription factor has been shown to be an important positive regulator of downstream meristem identity and floral homeotic genes, including AP1, AG, and AP3 (G. Parcy, et al., *Nature* 395:561-566 (1998); M. A. Busch, et al., *Science* 285:585-587 (1999)). Thus, ectopic expression of LFY in fie mutant embryos and seedlings contributes to the activation of downstream floral gene expression and promotes early flowering.

The plant polycomb genetic systems can be analogized to polycomb gene products in *Drosophila* and mammals. In *Drosophila* and mammals, WD motif polycomb proteins play an essential role during embryogenesis by assembling polycomb complexes that repress homeotic gene transcription (J. Ng, et al., *Mol. Cell Biol.* 20:3069-3078 (2000)). Without the action of these polycomb complexes, proper spatial polarity is not maintained, and the identity of larval and adult body segments is not correctly specified.

In *Drosophila*, the ESC WD-motif polycomb protein is thought to be recruited to specific sites on the chromatin by a zinc finger transcription factor, where in turn, it recruits SET-domain polycomb proteins, and possibly other proteins, that maintain target gene silencing (F. Tie, et al., *Development* 128:275-266 (2001)). The relationship between WD motif and SET domain polycomb proteins has been shown to be a direct physical interaction (T. Jenuwein, et al., *Cell and Mol. Life Sci.* 54:80-93 (1998); M. van Lohuizen, et al., *Mol. Cell Biol.* 18:3572-3579 (1998); R. G. Sewalt, et al., *Mol. Cell Biol.* 18:3586-3595 (1998)). Without intending to limit the scope of the invention, it is believed that FIE is associated with a complex that includes the FIS2 zinc finger protein and the MEA SET-domain polycomb protein, including in their role in endosperm repression. Evidence for their forming a complex includes experiments showing that FIE and MEA directly interact, and loss-of-function mutations in the FIS2, MEA and FIE genes result in similar mutant seed phenotypes (C. Spillane, et al., *Curr Biol* 10:1535-1538 (2000), R. Yadegari, et al., *Plant Cell* 12:2367-2381 (2000); M. Luo, et al., *Proc. Natl. Acad. Sci. USA* 96:296-301 (1999)). However, in contrast to what is observed for fie seedlings, homozygous mea and fis2 mutant seedlings do not display early flowering phenotypes (A. M. Chaudhury, et al., *Proc. Natl. Acad. Sci. USA* 94:4223-4228 (1997); T. Kiyosue, et al., *Proc. Natl. Acad. Sci. USA* 96:4186-4191 (1999); J.-P. Vielle-Calzada, et al., *Genes and Devel.* 13:2971-2982 (1999)), strongly suggesting that FIE associates with other molecular partners to control flowering time.

FIE is a single-copy gene in the *Arabidopsis* genome (N. Ohad et al., *Plant Cell* 11, 407 (1999)). In contrast, potential molecular partners for FIE (e.g., zinc finger transcription factors and SET-domain polycomb proteins) are encoded by gene families. The WD-motif polycomb protein may be a common component involved in the assembly of most, if not all, polycomb complexes. Thus, FIE may associate with distinct partners and assemble polycomb complexes that control other aspects of plant development beyond endosperm development and flowering.

Without intending to limit the scope of the invention, according to one hypothesis, to repress flowering, FIE interacts with CURLY LEAF (CLF), a SET-domain polycomb protein, as clf mutant plants display early flowering and ectopic AG and AP3 gene expression (J. Goodrich, et al., *Nature* 386:44-51 (1997)). FIE may also function in a protein complex with EMBRYONIC FLOWER 2 (EMF2) that has been reported to be a zinc finger protein homologous to FIS2. This hypothesis is supported by the fact that emf2 mutant seedlings bear a striking resemblance to fie seedlings. That is, emf2 seedlings are very early flowering, do not generate normal rosette leaves, and produce several sessile cauline-like leaves followed by multiple floral buds with sepals and sterile stamens and carpels (C.-H. Yang, et al., *Developmental Biol* 169:421-435 (1995); L. Chen, et al., *Plant Cell* 9:2011-2024 (1997)). Similar to fie seedlings, AP1 and AG promoters were shown to be activated in emf2 mutant seedlings. Thus, FIE, might form complexes with distinct zinc finger transcription factors (i.e., EMF2 and FIS2) and SET-domain polycomb proteins (i.e., CLY and MEA) to repress flowering and endosperm development, respectively. Seems like we can list these gene products in our list of polycomb gene products A genetic model has been proposed whereby the transition to flowering is the default state that is negatively regulated by floral repressors (D. Weigel, et al., *Nature* 377: 495-500 (1995); Z. R. Sung, A. Belachew, et al., *Science* 258:1645-1647 (1992); J. M. Martinez-Zapater, et al., in *Arabidopsis* E. M. Meyerowitz, C. Somerville, Eds. (Cold Spring Harbor Laboratory Press, Cold Spring Harbor, 1994) pp. 403-433; G. W. Haughn, et al., *Can. J Bot.* 73:959-981 (1995); M. Koornneef, et al., *Annu. Rev. Plant Physiol. Plant Mol. Biol.* 49:345-370 (1998)). Because mutations in the EMF genes result in little vegetative development, and are epistatic to early- and most late-flowering mutants, it has been proposed that the EMF genes may represent important floral repressors. Results from this study suggest that FIE-mediated polycomb protein complexes, that might include the EMF2 polypeptide, constitute a floral repression mechanism. Without intending to limit the scope of the invention, it is believed that flowering initiates when the activity of FIE mediated complexes has decreased in response to signals reflecting the developmental state of the plant (i.e., autonomous and gibberellin pathways) as well as the environment (i.e., vernalization and photoperiod pathways) (T. Araki, *Curr Opinion in Plant Biology* 4:63-68 (2001)).

Isolation of Polycomb Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of polycomb nucleic acids such as FIE or MEA may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the polycomb group gene transcript is prepared from the mRNA. Alternatively, cDNA may be prepared from mRNA extracted from other tissues in which polycomb group genes or homologs are expressed.

The cDNA or genomic library can then be screened using a probe based upon the sequences of cloned polycomb group genes disclosed here. Probes may be used to hybridize with genomic DNA or cDNA sequences to isolate homologous genes in the same or different plant species. Alternatively, antibodies raised against polycomb group polypeptides can be used to screen an mRNA expression library.

Alternatively, the nucleic acids of interest can be amplified from nucleic acid samples using amplification techniques: For instance, polymerase chain reaction (PCR) technology can be used to amplify the sequences of polycomb group genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), *Academic Press,* San Diego (1990).

Appropriate primers and probes for identifying polycomb group sequences from plant tissues are generated from comparisons of the sequences provided here with other related genes. For instance, FIE or MEA can be compared to the other polycomb genes. Using these techniques, one of skill can identify conserved regions in the nucleic acids disclosed here to prepare the appropriate primer and probe sequences. Primers that specifically hybridize to conserved regions in polycomb group genes can be used to amplify sequences from widely divergent plant species. Standard nucleic acid hybridization techniques using the conditions disclosed above can then be used to identify full-length cDNA or genomic clones.

Gene orthologs can be identified by PCR or hybridization techniques known in the art. In addition, methods for identifying orthologs are described in, e.g., U.S. patent application Ser. No. 09/512,882, filed Feb. 25, 2000.

A polypeptide of the invention optionally can possess additional amino acid residues at the amino-terminus or the carboxy-terminus. For example, 6×His-tag or FLAG residues may be linked to a polypeptide at the amino-terminus. See, e.g., U.S. Pat. Nos. 4,851,341 and 5,001,912. As another example, a reporter polypeptide such as green fluorescent protein (GFP) may be fused to the carboxy-terminus of the polypeptide. See, for example, U.S. Pat. No. 5,491,084.

Control of Polycomb Group Gene Activity or Gene Expression

Modulation of polycomb group (e.g. FIE or MEA) activity can cause changes in developmental programs. Developmental programs include, for example:

Embryogenesis;

Seed development;

initiation of organ growth and development, such as leave, roots, shoots, flowers;

initiation of tissue growth and development;

control of size, shape, identity or placement of organs;

control of size, shape, identity or placement of tissues;

control of size, shape, identity or placement of cells;

timing of initiation, growth, expansion, maturity, or death of organs, tissues, and cells; and coordination of any of these processes.

Generally, the timing, location, and extent developmental programs ensue can be regulated by modulation of polycomb group gene product activity. For example, polycomb group gene product activity can regulate when a plant makes the phase change from vegetative to reproductive growth. Here, altering FIE activity has been shown experimentally to either accelerate or delay flowering as compared wild type flowering time. See the Example section below for more details. Changing FIE activity can also control where developmental programs are triggered as illustrated by ectopic shoot formation that is triggered by FIE activity. The degree which a developmental program proceeds is another aspect that FIE activity regulate. For instance, FIE activity can permit continued, and thus ectopic, expression in the seedling of seed protein genes, which are typically only expressed during embryogenesis or turned off in late embryogenesis. Similarly, modulation of polycomb group gene products in general, including modulation of MEA activity, also modulates the above-described developmental phenotypes.

Generally, developmental programs which FIE activity can modulate include the transition from embryonic programs to vegetative growth, transition from vegetative growth to reproductive growth, root, shoot, leaf, and flower development.

In addition, FIE, as a member of a chromatin remodeling complex, is capable of modulating the transcription of a number of genes that are critical to developmental programs. Without intending to limit the scope of the invention, the FIE polypeptide is believed to be a member of the polycomb group, a protein complex that binds to chromatin and represses transcription via the complex's histone deacetylase activity. In this way, the FIE activity can regulate the expression of a genes that encode proteins involved in various developmental programs.

Specific examples of developmental changes and genes that can be modulated by polycomb group gene product activity (e.g., FIE or MEA activity) are listed in Table 3.

TABLE 3

| Phenotype | Polycomb group gene product activity (Up or Down Regulated) | Examples of tissues or cells where Polycomb group gene product activity is to be modulated to produce the desired phenotype | Developmental program genes modulated by a Polycomb group gene product |
|---|---|---|---|
| Cupped Cotyledons | Down | Cotyledon | AG is typically up regulation |
| Increased vegetative tissue | Up | Shoot apical meristem (SAM) | |
| Delayed flowering Time | Up | SAM | LFY, AP1, AP3, PI, AG (Down) |
| Early flowering Time | Down | SAM | LFY, AP1, AP3, PI, AG (Up) |
| Petal position | Down | SAM | |
| Reduced or missing petiole (either cotyledon or leaves) | Down | Petiole, Cotyledon, Leaves | |
| Reduced or missing seedling root | Down | Root | |
| Ectopic expression of embryonic genes in vegetative tissues or seedling. | Down | Embryo or seedling | CRUCIFERIN |
| Reduced or missing hypocotyl | Down | | |
| Ectopic shoot formation | Down | Hypocotyl, root, leaves, stems | |
| Disorganized roots (seedling) | Down | | |

To generate a plant where polycomb group gene product (e.g., FIE or MEA) activity is modulated, as described above, and capable of producing viable seed, polycomb group gene product activity must be sufficient in the desired cells, tissues, or organs. Generally, polycomb group gene product activity is sufficient when the polycomb group gene product activity in a transgenic plant is the same or similar to wild type plants in the desired tissues to produce a viable seed. Typically, when polycomb group gene product activity in the central cell and/or endosperm is the same or similar to wild type plants in the central cell and/or endosperm, viable seed will be produced. Other cells, tissues or organs where polycomb group gene product activity may be desired to produce viable seed include, without limitation, reproductive organs, female gametophyte, megaspore, ovule, or embryo.

Generally, the polycomb group gene product activity will be the same or similar to wild type levels in at least one of the above-listed tissues or organs when viable seed is produced. Other means for determining the level of activity include measuring the mRNA levels by Northern or in situ hybridization experiments; or measuring protein levels by gel electrophoresis or fusing a marker protein, such as GFP to a polycomb group gene product. In addition, protein levels or mRNA levels of target genes which are regulated by a polycomb group gene product activity can also be compared to wild type levels to determine if polycomb group gene product activity is sufficient to produce viable seed.

Furthermore, substantial inhibition of polycomb group gene product (e.g., FIE or MEA) activity in the central cells and/or endosperm can be used for production of fruit with small and/or degraded seed (referred to here as "seedless fruit") after fertilization. In many plants, particularly dicots, the endosperm is not persistent and eventually is degraded. Thus, in plants of the invention in which polycomb group gene product activity is inhibited, embryo-less seed do not persist and seedless fruit are produced.

Alternatively, plants of the invention can be used to prevent pre-harvest sprouting in seeds, especially those derived from cereals. In these plants, the endosperm persists and is the major component of the mature seed. Premature growth of embryos in stored grain causes release of degradative enzymes which digest starch and other components of the endosperm. Plants of the present invention are useful in addressing this problem because the seeds lack an embryo and thus will not germinate.

Inhibition of Polycomb Group Gene Activity or Expression

One of skill will recognize that a number of methods can be used to modulate polycomb group gene product (e.g., FIE or MEA) activity or gene expression. polycomb group gene product activity can be modulated in the plant cell at the gene, transcriptional, posttranscriptional, translational, or posttranslational, levels. Techniques for modulating polycomb group gene product activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering a polycomb group gene product gene in vivo (see, generally, Grewal and Klar, *Genetics* 146: 1221-1238 (1997)

and Xu et al., *Genes Dev.* 10:2411-2422 (1996)). Homologous recombination has been demonstrated in plants (Puchta et al., *Experientia* 50:277-284 (1994), Swoboda et al., *EMBO J.* 13:484-489 (1994); Offringa et al., *Proc. Natl. Acad. Sci. USA* 90: 7346-7350 (1993); and Kempin et al. *Nature* 389:802-803. (1997)).

In applying homologous recombination technology to the genes of the invention, mutations in selected portions of polycomb group gene product gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91:4303-4307 (1994); and Vaulont et al. *Transgenic Res.* 4:247-255 (1995) are conveniently used to increase the efficiency of selecting for altered polycomb group gene product gene expression in transgenic plants. The mutated gene will interact with the target wild-type gene in such a way that homologous recombination and targeted replacement of the wild-type gene will occur in transgenic plant cells, resulting in suppression of polycomb group gene product activity.

Alternatively, oligonucleotides composed of a contiguous stretch of RNA and DNA residues in a duplex conformation with double hairpin caps on the ends can be used. The RNA/DNA sequence is designed to align with the sequence of the target polycomb group gene product gene and to contain the desired nucleotide change. Introduction of the chimeric oligonucleotide on an extrachromosomal T-DNA plasmid results in efficient and specific polycomb group gene product gene conversion directed by chimeric molecules in a small number of transformed plant cells. This method is described in Cole-Strauss et al. *Science* 273:1386-1389 (1996) and Yoon et al. *Proc. Natl. Acad. Sci. USA* 93:2071-2076 (1996).

Gene expression can be inactivated using recombinant DNA techniques by transforming plant cells with constructs comprising transposons or T-DNA sequences. polycomb group gene product mutants prepared by these methods are identified according to standard techniques. For instance, mutants can be detected by PCR or by detecting the presence or absence of polycomb group gene product mRNA, e.g., by Northern blots. Mutants can also be selected by assaying for development of endosperm in the absence of fertilization.

The isolated nucleic acid sequences prepared as described herein, can also be used in a number of techniques to control endogenous polycomb group gene expression at various levels. Subsequences from the sequences disclosed here can be used to control, transcription, RNA accumulation, translation, and the like.

Additional methods to inhibit gene expression in plants include, for instance, antisense technology. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105:125-149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181-238; Heiser et al. *Plant Sci.* (Shannon) 127:61-69 (1997)) and by preventing the accumulation of mRNA which encodes the protein of interest, (see, Baulcombe *Plant Mol. Bio.* 32:79-88 (1996); Prins and Goldbach *Arch. Virol.* 141:2259-2276 (1996); Metzlaff et al. *Cell* 88:845-854 (1997), Sheehy et al., *Proc. Nat. Acad. Sci. USA,* 85:8805-8809 (1988), and Hiatt et al., U.S. Pat. No. 4,801,340).

The nucleic acid segment to be introduced generally will be substantially identical to at least a portion of the endogenous polycomb group gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 7000 nucleotides is especially preferred.

A number of gene regions can be targeted to suppress polycomb group gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to polycomb group gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed or in vegetative, floral, or root tissues. In one embodiment, transgenic plants are selected for polycomb group gene activity, e.g. FIE or MEA activity, that is reduced but not eliminated.

Oligonucleotide-based triple-helix formation can be used to disrupt polycomb group gene expression. Triplex DNA can inhibit DNA transcription and replication, generate site-specific mutations, cleave DNA, and induce homologous recombination (see, e.g., Havre and Glazer *J. Virology* 67:7324-7331 (1993); Scanlon et al. *FASEB J* 9:1288-1296 (1995); Giovannangeli et al. *Biochemistry* 35:10539-10548 (1996); Chan and Glazer *J. Mol. Medicine (Berlin)* 75:267-282 (1997)). Triple helix DNAs can be used to target the same sequences identified for antisense regulation.

Catalytic RNA molecules or ribozymes can also be used to inhibit expression of polycomb group genes such as FIE or MEA. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucemene transient streak virus, velvet tobacco mottle virus, solanum nodiflorum mottle virus and subterranean clover mottle virus. The design and use of target RNA-specific ribozymes is described in Zhao and Pick *Nature* 365:448-451 (1993); Eastham and Ahlering *J. Urology* 156:1186-1188 (1996); Sokol and Murray *Transgenic Res.* 5:363-371 (1996); Sun et al. *Mol. Biotechnology* 7:241-251 (1997); and Haseloff et al. *Nature,* 334:585-591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22:1067-1085 (1993); Flavell *Proc. Natl. Acad. Sci. USA* 91:3490-3496 (1994); Stam et al. *Annals Bot.* 79:3-12 (1997); Napoli et al., *The Plant Cell* 2:279-289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

In a preferred embodiment, expression of a nucleic acid of interest can be suppressed by the simultaneous expression of both sense and antisense constructs (Waterhouse et al., *Proc. Natl. Acad. Sci. USA* 95:13959-13964 (1998). See also Tabara et al. *Science* 282:430-431 (1998).

Alternatively, polycomb group gene activity may be modulated by eliminating the proteins that are required for polycomb group gene cell-specific gene expression. Thus, expression of regulatory proteins and/or the sequences that control polycomb group gene expression can be modulated using the methods described here.

Another method is use of engineered tRNA suppression of polycomb group gene mRNA translation. This method involves the use of suppressor tRNAs to transactivate target genes containing premature stop codons (see, Betzner et al. *Plant J.*11:587-595 (1997);

and Choisne et al. *Plant J* 11:597-604 (1997). A plant line containing a constitutively expressed polycomb group gene that contains an amber stop codon is first created. Multiple lines of plants, each containing tRNA suppressor gene constructs under the direction of cell-type specific promoters are also generated. The tRNA gene construct is then crossed into the polycomb group gene line to activate polycomb group gene activity in a targeted manner. These tRNA suppressor lines could also be used to target the expression of any type of gene to the same cell or tissue types.

Polycomb group proteins such as FIE or MEA may form homogeneous or heterologous complexes in vivo. Thus, production of dominant-negative forms of polycomb polypeptides that are defective in their abilities to bind to other proteins in the complex is a convenient means to inhibit endogenous polycomb protein activity. This approach involves transformation of plants with constructs encoding mutant polycomb group polypeptides that form defective complexes and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831-845 (1996).

Fusions of polycomb genes such as FIE or MEA with histone acetylase (HAT) can also be used to effect a dominant negative phenotype and to modulate polycomb protein activity in a cell. As described in the examples below, FIE and MEA activity can also be reduced by countering molecular actions taken by active FIE or MEA proteins. Without intending to limit the scope of the invention, when expressed in a cell, the FIE/HAT or MEA/HAT fusion is incorporated into polycomb complexes targeted to the chromosome, thereby replacing or countering the endogenous histone deacetylase in the cell. Thus the complex activates, rather than represses transcription. A FIE/HAT or MEA/HAT fusion polypeptide contains at least two polypeptide segments: a first polypeptide segment that exhibits HAT enzymatic activity, and a second polypeptide segment that exhibits its FIE or MEA activity respectively. Information regarding HAT fusions such as FIE/HAT and MEA/HAT fusions can be found in U.S. Provisional Patent Application No. 60/300, 135, filed Jun. 22, 2001 and in U.S. patent application Ser. No. 10/176,884, filed Jun. 21, 2002 and issued as U.S. Pat. No. 6,906,244, each of which is incorporated in its entirety for all purposes.

A polypeptide segment that exhibits HAT enzymatic activity is a suitable first polypeptide segment of a chimeric polycomb polypeptide. Whether a first polypeptide segment exhibits HAT enzymatic activity can be determined by testing either the polypeptide segment or the chimeric FIE or MEA polypeptide in an assay that measures the transfer of an acetyl functional group from an acetyl donor such as acetyl CoA to a histone polypeptide or polypeptide segment. See, e.g., Brownell, J. and Allis, C. D. (1995) *Proc. Natl. Acad. Sci.* 92, 6364-6368. This assay can be used to screen candidate polypeptide segments for HAT enzymatic activity, and to test chimeric polypeptides for HAT enzymatic activity.

In some embodiments, a first polypeptide segment has an amino acid sequence that corresponds to the amino acid sequence of one of the following polypeptides: yeast Esa1

Gcn5, Sas3, yTAFII130, ELP3, HAT1 or Hpa2; *Drosophila* dGcn5, dTAFII230 or MOF; Tetrahymena p55; or human hGcn5, p300/CPB, PCAF, Tip60, hTAFII250, TFIII90/110/220, SRC-1 or ACTR. In other embodiments, a first polypeptide segment can have an amino acid sequence with individual substitutions, insertions or deletions relative to one of the above-mentioned polypeptides. Any polypeptide segment having HAT enzymatic activity is suitable as a first polypeptide segment, irrespective of the number or character of amino acid insertions, deletions, or substitutions. Thus, in some embodiments, the amino acid sequence of a first polypeptide segment corresponds to less than the full-length sequence (e.g. a HAT functional domain) of one of the above-mentioned polypeptides.

Other suitable candidates for first polypeptide segments can be identified by homologous polypeptide sequence analysis. HAT amino acid sequence families are known to be conserved. For example, plant histone acetyltransferase genes can be identified by BLAST or PSI-BLAST analysis of nonredundant protein databases using known plant, yeast and/or animal histone acetyltransferase amino acid sequences. Homologous polypeptide sequence analysis involves the identification of conserved regions in a template polypeptide, also referred to herein as a subject polypeptide. Conserved regions can be identified by locating a region within the primary amino acid sequence of a template polypeptide that is a repeated sequence, forms some secondary structure such as helices, beta sheets, etc., establishes positively or negatively charged domains and represents a protein motif or domain. See, e.g., the Pfam web site describing consensus sequences for a variety of protein motifs and domains at the websites for sanger.ac.uk/Pfam and genome.wustl.edu/Pfam at. For a description of the information included at the Pfam database, see Sonnhammer et al., Nucl Acids Res 26(1): 320-322 (Jan. 1, 1998); and Sonnhammer E L, Eddy S R, Durbin R (1997) Pfam: A Comprehensive Database of Protein Families Based on Seed Alignments, Proteins 28:405-420; Bateman et al., Nucl. Acids Res. 27(1):260-262 (Jan. 1, 1999); and Sonnhammer et al., Proteins 28(3):405-20 (July 1997). From the Pfam database, consensus sequences of protein motifs and domains can be aligned with the template polypeptide sequence to determine conserved region(s).

Conserved regions can also be determined by aligning sequences of the same or related polypeptides from closely related plant species. Closely related plant species preferably are from the same family. Alternatively, alignment are performed using sequences from plant species that are all monocots or are all dicots. In some embodiments, alignment of sequences from two different plant species is adequate. For example, sequences from canola and *Arabidopsis* can be used to identify one or more conserved regions. Such related polypeptides from different plant species need not exhibit an extremely high sequence identity to aid in determining conserved regions. For examples, polypeptides that exhibit about 35% sequence identity can be useful to identify a conserved region. Typically, conserved regions of related proteins exhibit at least 50% sequence identity; or at least about 60%; or at least 70%, at least 80%, or at least 90% sequence identity. In some embodiments, a conserved region of target and template polypeptides exhibit at least 92, 94, 96, 98, or 99% sequence identity. Sequence identity can be either at the amino acid or nucleotide level.

Exemplary nucleotide and/or amino acid sequences of HAT genes and/or polypeptides are shown in SEQ ID NOS:8 and 9 as well as SEQ ID NOS:11-13. Yet other first polypeptide segments can be synthesized on the basis of consensus HAT functional domains. See, e.g., FIG. 1.

Segments of Polycomb gene product/HAT polypeptide fusions (e.g., FIE/HAT or MEA/HAT fusions) are joined to one another by covalent bonds, typically peptide bonds. The segments can be joined directly, without any intervening amino acids between two segments. Alternatively, one segment can be joined indirectly to an adjacent segment by amino acid residues that are situated between the two adjacent segments and are themselves covalently joined to the adjacent segments. In some embodiments, there are one, two, three, four, five, six, seven, eight, nine or ten intervening amino acid residues. In other embodiments, there are fifteen, twenty, thirty, forty or fifty intervening residues. In some embodiments, an intervening segment can be a hinge domain. Typically, if there is an intervening segment, at least one of the amino acids in the intervening segment is a glycine. At least one glycine is preferred in order to promote structural flexibility of the spacer, and permit free rotation of the first polypeptide segment relative to the second polypeptide segment. An illustrative embodiment of an intervening segment is one having fifteen glycine residues positioned between the first polypeptide segment and the second polypeptide segment and covalently linked to each by a peptide bond.

An intervening peptide segment can be situated between the segments of a FIE/HAT or MEA/HAT fusion polypeptide of the invention in order to facilitate interaction between the histone in a nucleosome and the HAT of the fusion polypeptide. Structural modeling can be used to predict whether an intervening peptide segment is useful in a chimeric HAT polypeptide. Structural modeling can be performed using software such as Rasmol 2.6, available from the UC Berkeley website http://mc2.CChem.Berkeley.EDU/Rasmol/v2.6/. For example, the theoretical distance between the first polypeptide segment of a chimeric polypeptide and the surface of a nucleosome is modeled, based on the crystal structure of a nucleosome (histones H2A, H2B, H3 and H4, and a 147 nucleotide DNA), the crystal structure of the DNA binding domain of a TATA binding protein and the crystal structure of a Tetrahymena histone acetyltransferase GCN5 homologue, including the coenzyme Acetyl-CoA and the 11-mer N-terminal tail of histone H3. The TATA binding protein is modeled as it is situated on the DNA of the nucleosome. The HAT is modeled while adjacent to the tail of histone H3. Next, the distance from the closest surface of HAT to the nucleosome surface is calculated. Based on this example, an intervening peptide segment of at least 28 Å in length facilitates interaction between the HAT and histone yet maintains nucleosome interaction and histone modification. Twenty eight Å is approximately the same length as a peptide containing 15 amino acids. Structural flexibility of the intervening peptide segment can be maximized by using at least one glycine residue.

The HAT polypeptide segment of a fusion polypeptide can be the N-terminal segment of a fusion polypeptide of the invention. In such embodiments, the C-terminus of the HAT polypeptide segment can be covalently linked to the N-terminus of a second polypeptide segment, which is a polycomb group gene product such as FIE or MEA, or can be covalently linked to the N-terminus of an intervening peptide segment, which can be schematically indicated at 1st-2nd or 1st-1-2nd, where. "1st" indicates the HAT polypeptide segment, "2nd" indicates the polycomb polypeptide segment and "i" indicates an optional intervening peptide segment.

In other embodiments, the first polypeptide segment can be the C-terminal segment of a fusion polypeptide of the invention. In such embodiments, the C-terminus of the second polypeptide segment is covalently linked to the N-terminus of the first polypeptide segment, or can be covalently linked to the N-terminus of an intervening peptide segment, which can be schematically indicated as 2nd-1st or 2nd-1-i-1st.

Yet another strategy to affect the ability of apolycomb protein to interact with itself or with other proteins involves the use of antibodies specific to a polycomb group protein. In this method cell-specific expression of polycomb group protein specific-Abs, such as FIE-specific or MEA-specific Abs, is used inactivate functional domains through antibody: antigen recognition (see, Hupp et al. Cell 83:237-245 (1995)).

After plants with, for example, reduced or no FIE activity, or alternatively, reduced or no MEA activity, are identified, a recombinant construct capable of expressing low levels of FIE or MEA activity in embryos can be introduced using the methods discussed below. In this fashion, the level of FIE or MEA activity can be regulated to produce preferred plant phenotypes. For example, a relatively weak promoter such as the ubiquitin promoter (see, e.g., Garbarino et al. Plant Physiol. 109(4): 1371-8 (1995); Christensen et al Transgenic Res. 5(3):213-8 (1996); and Holtorf et al. Plant. Mol. Biol. 29(4):637-46 (1995)) is useful to produce plants with reduced levels of FIE or MEA activity or expression. Such plants are useful for producing, for instance, plants that produce seed with enhanced endosperm or with other modulated development.

Enhancement of Plant Polycomb Gene Activity and/or Expression

Isolated sequences prepared as described herein can also be used to introduce expression of a particular polycomb group nucleic acid to enhance or increase endogenous gene expression. Without intending to limit the invention, it is believed that FIE and MEA act in a complex to repress transcription of genes by targeting cellular components, such as histone deacetylase to the chromosome where the components repress transcriptionenhanced expression can therefore be used to control plant morphology by controlling expression of genes under FIE's control in desired tissues or cells. Enhanced expression can also be used, for instance, to increase vegetative growth by delaying flowering. Where overexpression of a gene is desired, the desired gene from a different species may be used to decrease potential sense suppression effects.

One of skill will recognize that the polypeptides encoded by the polycomb group genes of the invention have different domains that perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of flowering plant species are well known and described in the technical and scientific literature. See, for example, Weising et al. Ann. Rev. Genet. 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumafaciens, and other transcription initiation regions from various plant genes known to those of skill. Such genes include for example, ACT11 from Arabidopsis (Huang et al. Plant Mol. Biol. 33:125-139 (1996)), Cat3 from Arabidopsis (GenBank No. U43147, Zhong et al., Mol. Gen. Genet. 251:196-203 (1996)), the gene encoding stearoyl-acyl carrier protein desaturase from Brassica napus (Genbank No. X74782, Solocombe et al. Plant Physiol. 104:1167-1176 (1994)), GPc1 from maize (GenBank No. X15596, Martinez et al. J. Mol. Biol. 208: 551-565 (1989)), and Gpc2 from maize (GenBank No. U45855, Manjunath et al., Plant Mol. Biol. 33:97-112 (1997)).

Alternatively, the plant promoter may direct expression of polycomb group nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include polycomb gene promoters described herein, including SEQ ID NO:7 (described, e.g., in Yadegari et al., Plant Cell 12:2367-2381 (2000), which directs expression in the endosperm during early seed development and in both the endosperm and embryo during later stages. Another suitable promoter is from the ovule-specific BEL1 gene described in Reiser et al. Cell 83:735-742 (1995) (GenBank No. U39944). Other suitable seed specific promoters are derived from the following genes: MAC1 from maize (Sheridan et al. Genetics 142:1009-1020 (1996), Cat3 from maize (GenBank No. L05934, Abler et al. Plant Mol. Biol. 22:10131-1038 (1993), the gene encoding oleosin 18 kD from maize (GenBank No. J05212, Lee et al. Plant Mol. Biol. 26:1981-

1987 (1994)), vivparous-1 from *Arabidopsis* (Genbank No. U93215), the gene encoding oleosin from *Arabidopsis* (Genbank No. Z17657), Atmyc1 from *Arabidopsis* (Urao et al. *Plant Mol. Biol.* 32:571-576 (1996), the 2s seed storage protein gene family from *Arabidopsis* (Conceicao et al. *Plant* 5:493-505 (1994)) the gene encoding oleosin 20 kD from *Brassica napus* (GenBank No. M63985), napA from *Brassica napus* (GenBank No. J02798, Josefsson et al. *JBL* 26:12196-1301 (1987), the napin gene family from *Brassica napus* (Sjodahl et al. *Planta* 197:264-271 (1995), the gene encoding the 2S storage protein from *Brassica napus* (Dasgupta et al. *Gene* 133:301-302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266-268 (1995)).

In addition, the native or modified promoter sequences from the polycomb group genes disclosed here can be used to drive expression of the polycomb polynucleotides of the invention or heterologous sequences. For example, modified FIE promoter sequences, such as SEQ ID NO:4, SEQ ID NO:5, or SEQ ID NO:6, which have specific expression in the central cells and endosperm, are useful for generating plants that produce FIE at the developmentally appropriate stage to allow for viable seed and plants. Modifications of the FIE promoter, include, for example, deletion or modification of at least one nucleotide in nucleotides −128 to +10 of the FIE promoter (e.g., SEQ ID NO:3). All nucleotide positions above are with reference to the start of translation (i.e., ATG).

As described below, when such promoters are operably linked to a FIE polynucleotide and introduced into a fie mutant plant, the resulting plants remain viable, but lack FIE in most tissues. Of course, those of skill in the art will recognize that such expression patterns can also be generated, for instance, by introducing antisense FIE constructs under tissue-specific or inducible promoters into plants with an intact native FIE gene, thereby resulting in plants with reduced FIE activity when and where the promoters drive expression of the antisense construct.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control FIE gene expression, Northern blot analysis can be used to screen for desired plants. In addition, the presence of modulated development in one or more plant tissue can be detected. Also, plants can be screened, for instance, for the altered timing of embryonic, vegetative or reproductive (e.g., floral) developmental. These procedures will depend, in part on the particular plant species being used, but will be carried out according to methods well known to those of skill.

The following Examples are offered by way of illustration, not limitation.

EXAMPLES

Example 1

This example demonstrates that FIE controls developmental stages after seed development.

A transgene that specifically provides FIE protein for seed viability, but does not appear to function at other stages of the plant life cycle was used to examine FIE function after developmental stages after seed development. To understand FIE polycomb function, *Arabidopsis* lines bearing a transgene, pFIE::FIE-GFP was generated. The introduced DNA sequence included 1,639 base pairs of FIE 5'-flanking sequences and a modified FIE 5'-untranslated region (jointly referred to as pFIE or SEQ ID NO:4), as well as sequences that encode the full-length FIE protein (FIE), a linker sequence encoding six glycine amino acids (SEQ ID NO:20), followed by sequences encoding a modified green fluorescent protein (GFP) (Y. Niwa, et al., *Plant J.* 18:455-463 (1999)). To contruct a FIE-GFP fusion protein, the FIE cDNA was amplified with primers FIE-Sal (5'-ATGTC-GACGAGAGTCAGACAGAGAGAGAG-3'; SEQ ID NO:21) and FIE-NcoI (5'-CACCATGGCTCCGCCACCTC-CGCCACCCTTGGT AATCACGTCCCAGCG-3'; SEQ ID NO:22), digested with Sal I and Nco I, and inserted into the CaMV35S-sGFPS65T-Nos vector to obtain the CaMV35S::FIE-sGFPS65T-Nos plasmid. The GFP gene used in these experiments lacks subcellular localization sequences. To have transcription of the FIE-GFP fusion gene under the control of a FIE promoter, 1,639 base pairs of FIE 5'-flanking sequences were amplified with primers FIE-Sph (5'-TTCCTATAAGAGGCATGcGAGGAAGG-GAGCAAGTACACA-3'; SEQ ID NO:23) and FIE-SalRV (5'-TCTGACTCTCGTCGACTAATCTAAGCT-CACAAGTCTCTCA-3'; SEQ ID NO:24), digested with Sal I and Sph, and inserted into the CaMV35S::FIE-sGFPS65T-Nos plasmid to create the CaMV35S::pFIE::FIE-sGFPS65T-Nos plasmid. This plasmid was digested with Pst I and Hind III to liberate the pFIE::FIE-GFP transgene that was then inserted into pBI101.1 (R. A. Jefferson, et at., *EMBO J* 6:3901-3907 (1987)), replacing the β-glucuronidase reporter, to create plasmid pBI(pFIE::FIE-GFP) that was introduced into *Agrobacterium* GV3101. *Arabidopsis* plants were transformed as described previously (N. Ohad, et at., *Plant Cell* 11:407-415 (1999)). Expression of pFIE::FIE-GFP was highly restricted compared to previously reported constructs (Yadegari, et at. *Plant Cell* 12:2367-2381 (2000)) and this may be due to the fact that the process of creating a Sal I site in the FIE cDNA changed nucleotides −38 to −36 (as measured from the start codon) in the 5'-untranslated region from GTG to CGA.

Expression of the transgene, observed in multiple independently transformed lines, was highly restricted when compared to the pattern of FIE RNA accumulation (C. Spillane, et al., *Curr Biol* 10:1535-1538 (2000)) and related FIE::GFP transgene expression (R. Yadegari, et al., *Plant Cell* 12:2367-2381 (2000)). GFP fluorescence was detected in the central cell nucleus prior to fertilization and in the primary endosperm nucleus after fertilization. By the 8-cell endosperm stage, GFP fluorescence was no longer detected, nor was GFP fluorescence detected at any other stage of plant development. Because the GFP protein lacks subcellular localization sequences (see, e.g., Y. Niwa, et al., *Plant J.* 18:455-463 (1999); Yadegari, et al., supra), appearance of GFP fluorescence primarily in nuclei reflects nuclear localization signals present on the FIE moiety (N. Ohad, et al., supra) and suggests that a significant fraction of the FIE-GFP fusion protein is intact.

Inheritance of a mutant maternal fie-1 null allele results in seed abortion (N. Ohad, et al., supra). Thus, siliques from control self-pollinated fie-1/FIE plants contain 50% non viable seeds and when germinated the seedlings segregated 1:1 for FIE/FIE: fie-1/FIE genotypes. In contrast, self-pollinated heterozygous fie-1/FIE plants that are homozygous for the pFIE::FIE-GFP transgene displayed siliques with no seed abortion.

The genotype of plants was determined using PCR-based procedures. To specifically amplify endogenous FIE gene sequences we used primers 579dXba (5'-CATTACTGC-CATTGGTGTATCTCTTATTATCTA-3'; SEQ ID NO:25) and 48S4 (5'-CACTGTTGACGTCAATGACTCGG-3'; SEQ ID NO:26). Because the 579dXBa primer is located in the first intron of the FIE gene, it does not amplify any sequences associated with the pFIE::FIE-GFP transgene. The fie-1 and wild type FIE alleles were distinguished by digesting the amplified products with Xba I restriction endonuclease followed by agarose gel electrophoresis. The PGR amplified product from the wild type FIE allele is digested, whereas the fie-1 allele is not. To specifically amplify pFIE::FIE-GFP transgene sequences, a primer in the FIE cDNA region, FIE-RTf(5'-CTGTAATCAGGCAAA-CAGCC-3'; SEQ ID NO:27), and a primer in the GFP cDNA region, GFP274r (5'-GCATGOCGGACTTGAAGA-3'; SEQ ID NO:28) was used. PCR reactions were performed as described previously (Yadegari, et at., supra). In addition, we identified seedlings on agar plates with the pFIE::FIE-GFP transgene by the fact that the T-DNA vector has a neomycin phosphotransferase gene that renders seedlings resistant to 50 μg/ml kanamycin. While the data below was developed using the promoter represented by SEQ ID NO:4, similar results have been found using SEQ ID NO:5 as the promoter.

When germinated, we observed seedlings, all homozygous for the pFIE::FIE-GFP transgene, with mendelian 1:2:1 segregation (20:28:12, $\chi^2$=2.6, P=0.35) of FIE/FIE: fie-1/FIE: fie-1/fie-1 genotypes. Thus, expression of the pFIE::FIE-GFP transgene in the central cell and early endosperm rescues embryo and seed abortion associated with inheritance of a maternal mutant fie-1 allele. This shows that the FIE-GFP fusion protein is active, and suggests that embryo and seed abortion may be due primarily to a defect in endosperm development.

Plants homozygous for the pFIE::FIE-GFP transgene that were either homozygous for the wild type FIE allele, or heterozygous fie-1/FIE, developed normally. That is, after germination, these seedlings produced two petiolated cotyledons followed by a rosette (i.e., nodes closely compressed) of petiolated leaves. The inflorescence phase was initiated by internode elongation and the production of sessile (i.e., non-petiolated) cauline leaves and secondary inflorescences. Finally, in the late inflorescence phase, nodes were produced bearing solitary flowers comprised of whorls of sepals, petals, stamens and carpels arranged in a crucifer phyllotaxis. Thus, in the presence of a wild-type FIE allele, the pFIE::FIE-GFP transgene caused no detectable alteration in plant development.

All seedlings tested that were homozygous for the fie-1 allele and the pFIE::FIE-GFP transgene did not develop normally. Mutant seedlings were smaller and did not produce a normal rosette. In some cases, highly disorganized structures emerged from the shoot apical meristem. Seedlings often produced sessile leaves with trichomes that resembled cauline leaves. We also observed white petal-like organs lacking trichomes. In some cases, floral buds emerged surrounded by sessile cauline leaves with branched trichomes. Within the floral buds, outer whorl sepals could be distinguished by the appearance of unbranched trichomes on their abaxial surfaces and by their highly elongated cells. Inner whorl organs whose distinctive shapes resembled immature stamens and carpels were also observed. Finally, floral organs within flower buds often displayed proper crucifer phyllotaxy. The mutant phenotypes described above were observed in multiple independently isolated transgenic lines, as well as in seedlings homozygous for the null fie-1 allele and for a pFIE::FIE transgene that produces FIE protein without a GFP moiety. Thus, the mutant phenotypes were not due to unexpected effects caused by GFP. Taken together, these results show that the transition from vegetative to inflorescence development has prematurely occurred in the shoot apical meristem of seedlings homozygous for the null fie-1 allele and the pFIE::FIE-GFP transgene. This suggests that the function of the wild type FIE gene is to repress the transition to flowering in the shoot apical meristem.

Production of shoots and floral-like organs was not limited to the shoot apical meristem in seedlings homozygous for the fie-1 allele and the pFIE::FIE-GFP transgene. Shoots frequently emerged from the hypocotyl and roots of intact seedlings. Carpel-shaped cylindrical organs with stigmatic papillae at their tips were detected. In addition, carpelloid organs tipped with stigmatic papillae and with ovule-like primordia on their edges were observed. In some cases, shoots with organs arranged in a floral crucifer phyllotaxy were observed. When roots were cultured in hormone-free media, many additional organs were produced with stimatic papillae and ovule-like primordia. These results show that ectopic shoot and floral-like organ production occurs in seedlings homozygous for the fie-1 allele and the pFIE::FIE-GFP transgene. These results suggest that the function of the wild type FIE allele is to repress the formation of shoots and floral organs outside of the shoot apical meristem region.

The mutant phenotypes described above were observed in transgenic pFIE::FIE-GFP or pFIE::FIE seedlings that were homozygous for the null fie-1 allele, and were never observed when a wild-type FIE allele was present. Thus, the pFIE::FIE-GFP and pFIE::FIE transgenic alleles are recessive to the wild type FIE allele. This fact, along with the highly restricted pattern of pFIE::FIE-GFP gene expression, suggest that loss of FIE activity is responsible for early flowering and ectopic shoot formation in seedlings that are homozygous for the null fie-1 allele and have a pFIE::FIE-GFP transgene. From this we reasoned that increasing the level of FIE protein with an additional transgene would result in plants that develop more normally. To test this hypothesis, a transgene, CaMVp::FIE-GFP, was constructed where transcription of FIE-GFP is under the control of the constitutive Cauliflower Mosaic Virus (CaMV) promoter (S. G. Rogers, et al., *Meth Enzymol* 153:253-277 (1987)). The CaMVp::FIE-GFP transgene was introduced into wild type *Arabidopsis* by *Agrobacterium*-mediated transformation. By genetic crosses, we generated plants that were homozygous for fie-1, pFIE::FIE-GFP, and CaMVp::FIE-GFP. These plants did not display any of the mutant phenotypes found in the fie plants including the pFIE::FIE-GFP transgene. Rather, they produced rosette leaves, followed by inflorescences and fertile flowers. Similar results were observed when a CaMVp::FIE transgene, lacking the GFP moiety, was introduced into a homozygous fie-1 and pFIE::FIE-GFP background. Taken together, these data verify that early flowering at the shoot apical meristem, and ectopic shoot and floral organ formation in the hypocotyl and root, is due to a critical lack of FIE activity in seedlings homozygous for fie-1 and the pFIE::FIE-GFP transgene.

Example 2

This example demonstrates that FIE repressed expression of floral meristem identity genes.

To understand the molecular basis for the early flowering phenotypes, the expression of meristem and floral organ identity genes in mutant and control seedlings was measured. LEAFY (LFY) and APETAL1 (AP1) encode transcription factors that promote floral meristem identity in *Arabidopsis* and, with the aid of other factors, activate transcription of downstream floral meristem and organ identity genes such as AGAMOUS (AG), APETALA3 (AP3), and PISTILLATA (PI) (G. Parcy, et al., *Nature* 395:561-566 (1998)). LFY RNA was present at a low level, and AP1 RNA was not detected, in wild type 7-day and 14-day seedlings. The same result was observed in 7- and 14-day seedlings with the pFIE::FIE-GFP transgene. However, in seedlings that were homozygous fie-1 with a pFIE::FIE-GFP transgene, LFY RNA concentration was significantly elevated in 7-day seedlings, and AP1 RNA concentration was increased in both 7-day and 14-day seedlings. No effect on the flowering time genes, CONSTANS (CO) (J. Putterill, et al., *Cell and Mol. Life Sci.* 80:847-857 (1995)) or FLOWERING LOCUS T (FT) (Y. Kobayashi, et al., *Science* 286:1960-1962 (1999); I. Kardailsky, et al., *Science* 286:1962-1965 (1999)) were observed. Because ectopic expression of either LFY or AP1 is sufficient to convert the normally indeterminate shoot apex to a floral meristem that forms a terminal flower (D. Weigel, et al., *Nature* 377:495-500. (1995); M. A. Mandel, et al., *Nature* 377:522-524 (1995)), it is likely that aspects of the fie early flowering phenotype are due to their ectopic expression. Floral organ identity gene expression was also affected by the level of FIE activity. Whereas AG and PI RNAs were not detected in control wild type or pFIE::FIE-GFP seedlings, both RNAs accumulated in homozygous fie-1, pFIE::FIE-GFP seedlings. Taken together, these results suggest that FIE-mediated polycomb complexes, either directly or indirectly, repress expression of both floral meristem identity genes and floral organ identity genes during seedling development.

To investigate the spatial regulation of gene transcription by FIE-mediated polycomb complexes, we determined the activity of LFY, AG, and AP3 promoters ligated to the β-GLUCURONIDASE (GUS) reporter gene (M. Luo et al., *Proc. Natl. Acad. Sci. USA* 96, 296 (1999)) in transgenic seedlings. LFY::GUS transcription was restricted to the wild type seedling shoot apical meristem, whereas there was no detectable transcription of the AG::GUS or AP3::GUS transgenes in wild type seedlings. In contrast, homozygous fie-1 seedlings with the pFIE::FIE-GFP transgene showed elevated LFY::GUS, AG::GUS, and AP3::GUS transcription in the shoot apical meristem, cotyledon, and hypocotyl regions. These results show that FIE-mediated polycomb complexes, either directly or indirectly, repress transcription of floral meristem identity and floral organ identity genes in the aerial seedling.

When does repression of flowering and floral-promoting gene transcription begin? Might floral repression be a process that occurs early in plant development during embryogenesis? To test this hypothesis, embryo RNA was isolated from self-pollinated plants heterozygous for fie-1/FIE and homozygous for the pFIE::FIE-GFP transgene. Twenty-five percent of these embryos are homozygous for fie-1 and the pFIE::FIE-GFP transgene. Control wild type embryo RNA was also isolated. Semi-quantitative RT-PCR analysis indicated that the level of LFY, AG and PI RNA was elevated in the population that included homozygous fie-1, pFIE::FIE-GFP embryos. In this experiment, we could not detect AP1 embryo RNA in either embryo population. Finally, expression of control genes, PK and APG, that flank the AG gene in the *Arabidopsis* genome, was the same in both embryo populations. These results suggest that FIE-mediated polycomb complexes function during embryogenesis to repress the expression of certain floral meristem and organ identity genes.

To quantify RNA levels, total RNA from seedlings was isolated as describe previously (T. Kinoshita, et al., *Plant Cell* 11:1945 (1999)) at the indicated day after germination, or from stage 1 to stage 12 (J. L. Bowman, *Plant Cell* 1:37 (1989)) floral buds (FB). For reverse transcriptase reactions, 0.2 µg RNA was converted to cDNA as described previously (T. Kinoshita, et al., supra). Amplification of cDNA by PCR involved incubation at 94 C for 2 minutes, followed by 30 cycles at 94 C for 30 seconds, 55 C for 30 seconds, and 72 C for 10 seconds. The following gene specific primers were used: AP1 (AP1500f 5'-GATGATATAAGAACATCGAA-CATTTGCCA-3' (SEQ ID NO:29) and AP1991r 5'-GAT-GATATAAGAACATCGAACATTTGCCA-3' (SEQ ID NO:30)), LFY (LFY4042f 5'-GCTAAAGACCGTGGC-GAA-3' (SEQ ID NO:31) and LFY5371r 5'-GCATCCAC-CACGTCCAGA-3' (SEQ ID NO:32)), AG AG5523f 5'-GT-TGATTTGCATAACGATAACCAGA-3' (SEQ ID NO:33) and AG6116r 5'-TTCACTGATACAACATTCATGGGAT-3' (SEQ ID NO:34)), PI (PI1500f 5'-CACGCCATTGAA-CATGGCCT-3' (SEQ ID NO:35) and PI2020r 5'-TCGAT-GATCAATCGATGACCAA-3' (SEQ ID NO:36)), and actin (ACT.conf 5'-GATTTGGCATCACACTTTCTACAATG-3' (SEQ ID NO:37) and ACT.conr 5'-GTTCCACCACTGAG-CACAATG-3' (SEQ ID NO:38)).

Analysis of floral promoter activity. β-glucuronidase enzyme activity was measured by staining with 1 mM X-Gluc (5-bromo-4-chloro-3-indolyl-β-D-glucuronic acid), 0.1% Triton X-100, in 50 mM sodium phosphate buffer (pH 7.0) overnight at 37 C as described previously (R. A. Jefferson, et al., *EMBO J* 6, 3901 (1987)). Arrow points to GUS stained shoot apical meristem region in the LFY::GUS seedling. fie-1 FIE-GFP, seedlings that are homozygous for the mutant fie-1 allele with at least one copy of the pFIE::FIE-GFP and indicated reporter transgene. Scale bars represent 1 mm. The following transgenic lines were used: CS6297 obtained from the *Arabidopsis* Biological Resource Center (LFY::GUS) (D. Weigel, et al., *Cell* 69:843 (1992)), KB9 (AG::GUS) (M. A. Busch, et al, *Science* 285, 585 (1999)), 890-7 (AP3::GUS) (T. Jack, et al. Meyerowitz, *Cell* 76, 703 (1994)).

Using previously described procedures (T. Kinoshita, et al, *Plant Cell* 11: 1945 (1999)), total RNA was isolated from walking stick stage embryos dissected from either self-pollinated wild-type siliques or from self-pollinated siliques that were heterozygous fie-1/FIE and homozygous for the pFIE::FIE-GFP transgene. Twenty-five percent of the embryos used for RNA isolation were predicted to be homozygous for fie-1 and for the pFIE::FIE-GFP transgene. For reverse transcriptase reactions, 0.2 µg RNA was converted to cDNA using gene specific primers. As controls, we measured the expression of two genes that flank the AG gene in the *Arabidopsis* genome: PK (protein kinase-like protein; CAB78897.1) and APG (proline rich protein; CAB78899.1).

PK and APG sequences were amplified using primers PKf (5'-CTTCACCACATGGGTCACA-3'; SEQ ID NO:39) and PKr2 (5'-CTAAACCGGAAGGAATGGA-3'; SEQ ID NO:40), and APGf (5'-CTTGTGTCTCTGGTTGATCA-3'; SEQ ID NO:41) and APGr2 (5'-CTCTGTGTTTGCTTG-GAGGA-3'; SEQ ID NO:42), respectively.

Example 3

This example demonstrates that expression of additional quantities of FIE results in delayed flowering.

Plants homozygous for the wild type endogenous FIE allele that also bear a pFIE::FIE transgene displayed late flowering. The delayed-flowering phenotype was associated with increased number of vegetative leaves produced (M. Koornneef, et al., *Annu. Rev. of Plant Physiol. Plant Mol. Biol.* 49:345 (1998)). Wild type (i.e., Columbia-0 ecotype or Landsberg erecta ecotype) produce 8 to 10 vegetative leaves before initiating flowering when grown under long-day (i.e., 16 hour light per day) conditions. In contrast, pFIE::FIE transgenic plants produced 15 to 25 leaves before initiating flowering when grown under the same conditions.

Example 4

This example demonstrates that FIE regulates the transition from embryonic to vegetative development in plants.

Expression of a seed storage protein gene, CRUCIFERIN (i.e., 12S seed storage protein gene) was dramatically elevated in 7-day and 14-day seedlings that were homozygous fie-1 with a pFIE::FIE-GFP transgene. No CRUCIFERIN expression was detected in control wild type and wild type with the pFIE::FIE-GFP transgene. This shows that the wild type FIE polycomb protein represses seed protein gene expression. This suggests that FIE regulates the transition from embryonic to vegetative development in *Arabidopsis*.

In light of this finding, it is possible that FIE represses expression of LEC1 (LEAFY COTYLEDON1) which, in turn, is a positive regulator of seed protein gene expression (L. Lotan et al., *Cell* 93:1195 (1998)). Consistent with this hypothesis is the observation that mutations in a Mi2-like gene, PKL (PICKLE) induces LEC1 and seed protein gene expression (J. Ogas, S. Kaufmann, J. Henderson, C. Somerville, *Proc. Natl. Acad. Sci. USA* 96:13839 (1999)).

Example 5

This example demonstrates that FIE controls root structure.

*Arabidopsis* root structure and cell files are very precisely controlled (B. Scheres, *Annu. Rev. Plant Physiol. Plant Mol. Biol.* 50:505 (1999)). Seedlings that were homozygous fie-1 with a pFIE::FIE-GFP transgene displayed disrupted root structure and cell file organization. Thus, FIE is required for proper root development.

Example 6

This example demonstrates the development of a new endosperm-specific promoter.

To obtain information about the spatial regulation of FIE gene expression, we transformed *Arabidopsis* plants with chimeric genes with FIE 5'-flanking sequences ligated to a GREEN FLUORESCENT PROTEIN (GFP) reporter gene (I. Korf, Y. Fan, S. Strome, *Development* 125.2469 (1998);

J. van der Vlag, A. P. Otte, *Nat. Genet.* 23:474 (1999)). For convenience, position "0" is arbitrarily designated as the start of translation (i.e., ATG codon). As previously reported (R. Yadegari et al., *Plant Cell* 12:2367 (2000)), the expression of a transgene with A FIE promoter extending from −1310 to +10 (i.e., includes the entire FIE 5'-untranslated sequence (−198 to 0) occurs in the central cell of the female gametophyte, in early endosperm development, and mid- and late-embryo and endosperm development.

When sequences from −128 to +9 are deleted, transgene expression is not detected in the embryo. Rather, expression is only detected in the central cell and endosperm. Thus, the −1274 to −128 promoter is an endosperm-specific promoter. All positions are measured compared to the adenosine of the start codon (ATG), which is designated as "+1" with the preceding base pair designated "−1". This promoter (SEQ ID NO:6) is useful for targeting gene expression to the endosperm.

Example 7

This example demonstrates the identification of polypeptides having histone acetyltransferase activity.

Polypeptides are tested for histone acetyltransferase activity using assays previously described Brownell, J. and Allis, C. *PNAS* 92, 6364-6368 (1995) and Brownell, J. E. et al. *Cell* 84,843-851 (1996). Coding sequences of candidate polypeptides are cloned into an appropriate expression vector, the expression vector is introduced into a bacterial host strain, expression of the gene is induced and protein extract is prepared. The extracts are incubated with calf thymus histones and [$^3$H]-acetyl-Coenzyme A. Radioactivity transferred to the histone substrate in an extract-dependent manner is quantified by liquid scintillation counting. Candidate polypeptides that transfer radioactivity to the histone substrate compared to positive controls (extracts from hosts expressing known HAT polypeptides) and negative controls (extract alone, histones without extract and comparable vector-only) have HAT activity. Alternatively, plant HAT activity is tested by determining whether expression of an *Arabidopsis* HAT cDNA is sufficient to rescue a yeast HAT mutant.

Example 8

This example demonstrates the identification of polypeptides having histone deacetylase activity.

Polypeptides are tested for histone deacetylase activity using assays previously described by van der Vlag, J. and Otte A. P. in *Nature Genetics* 25, 474-478 (1999). Coding sequences of candidate polypeptides are cloned into an appropriate expression vector, the expression vector is introduced into a bacterial host strain, expression of the gene is induced and protein extract is prepared. The extracts are incubated with [$^3$H]-acetylated histones or histone segments for 3-6 hours at 37° C. under shaking conditions in a buffer containing 20 mM Tris.-HCl, pH 7.4, ad 50 mM NaCl. The reaction is stopped by adding 7.7 mM HCl/1.2M acetic acid, and extracted with ethyl acetate. After centrifugation, the ethyl acetate fraction is counted in a liquid scintillation counter. Candidate polypeptides that remove radioactivity from the histone substrate compared to positive controls (extracts from hosts expressing known HDAC polypeptides) and negative controls (extract alone, histones without extract, vector-only, and parallel trichostatin A-containing reactions) have HDAC activity. Alternatively, plant HDAc activity is tested by determining whether expression of an *Arabidopsis* HDAc cDNA is sufficient to rescue a yeast HDAc mutant.

Example 9

This example demonstrates the chimeric HAT nucleic acid constructs.

The chimeric HAT gene construct pFIE-15G-ESA1 was constructed using standard molecular biology techniques. The construct contains the coding sequence for the *Arabidopsis* FIE polypeptide and the coding sequence for an *Arabidopsis* HAT polypeptide joined in frame by a DNA fragment encoding fifteen glycine residues. The FIE coding sequence was obtained from plasmid pFIE3.6. The *Arabidopsis* FIE polypeptide is a homolog of the *Drosophila* polycomb protein extra sex combs (esc) (Ohad et al., *Plant Cell* 11:407-415 (1999)). The *Arabidopsis* HAT polypeptide AtESA1 is a homolog of the yeast ESA1 polypeptide. pFIE-15G-ESA1 contains 5 binding sites for the DNA binding domain of the Gal4 transcription factor (UAS$_{GAL4}$) located 5' to a CaMV35S minimal promoter. The pFIE-15G-ESA1 construct includes an active fragment of the *Arabidopsis* ESA1 promoter. The CaMV35S minimal promoter is located 5' to the FIE coding sequence. A DNA fragment encoding fifteen glycine residues is present, in frame, at the 3' end of the UAS-FIE DNA sequence, followed, in frame, by a DNA fragment encoding an *Arabidopsis* homologue of ESA1.

The coding sequence of AtESA1 was fused to the 3'-end of the FIE coding sequence by fusion PCR (Levin HL, 1995 MCB 15:3310-3317). Two intermediate PCR products were generated for this purpose. The first intermediate product contained the FIE coding sequence with a 15-glycine spacer added to its carboxy-terminus. This product was generated using two synthetic oligonucleotides and a pFIE3.6 DNA template. Similarly, the second intermediate PCR product contained the AtESA1 coding sequence with a 15 glycine spacer added to its amino-terminus. This product was generated using two synthetic oligonucleotides and a pAtESA1 cDNA template. The two intermediate products were then fused to each other in a final round of PCR using a set of synthetic primers that introduced a BglII site at the 5' end of the fusion and a XhoI site at the 3' end of the fusion. The resultant PCR product contained a chimeric sequence encoding a fusion peptide in which the amino-terminus of the FIE coding sequence is linked by a 15-glycine spacer to the carboxy-terminus of the AtESA1 coding sequence. This final PCR product was digested with BglII and XhoI and cloned into the Ti-plasmid vector pCRS304-5UAS which was previously digested with BamHI and XhoI. The resulting plasmid was named pCRS304-5UAS-FIE-15G-ESA1. The transgene was designated FIE-15G-ESA1. The amino acid sequence of the chimeric polypeptide encoded by the transgene is shown in SEQ ID NO:8 and the nucleotide sequence of the transgene is shown in SEQ ID NO:9.

Thus, pCRS304-5UAS-FIE-15G-ESA1 encodes a chimeric polypeptide having an *Arabidopsis thaliana* FIE polypeptide and an *Arabidopsis thaliana* HAT polypeptide, joined by an intervening peptide spacer of 15 glycine residues. The plasmid contains 5 copies of the Gal4 upstream activator sequence (UAS$_{GAL4}$) located 5' and operably linked to the CaMV35S minimal promoter. This in turn is located 5' and operably linked to the FIE-15G-ESA1 coding sequence. The binding of a transcription factor that possesses a Gal4 DNA binding domain to the Gal4 UAS is necessary for transcriptional activation.

Example 10

This example demonstrates the chimeric HAT Nucleic Acid construct pMEA-15G-ESA1

The chimeric HAT gene construct pMEA-15G-ESA1 was constructed using standard molecular biology techniques. The construct contains the coding sequence for the *Arabidopsis* MEA polypeptide and the coding sequence for an *Arabidopsis* HAT polypeptide joined in frame by a DNA fragment encoding fifteen glycine residues. The MEA coding sequence was obtained from plasmid pCB1(MEA-cDNA) (Kiyosue, T., et al. (1999) *Proc. Natl. Acad. Sci. USA* 96:4186-4191). The *Arabidopsis* MEA polypeptide is a homolog of the *Drosophila* polycomb protein Enhancer of zeste (E(z)) (see Grossniklaus, U., et al. (1998) *Science* 280: 446-450.; Kiyosue, T., et al. (1999) *Proc. Natl. Acad. Sci. USA* 96:4186-4191). The *Arabidopsis* HAT polypeptide AtESA1 is a homolog of the yeast ESA1 polypeptide (Ceres clone ID: 266771). pMEA-15G-ESA1 plasmid contains 5 binding sites for the DNA binding domain of the Gal4 transcription factor ($UAS_{GAL4}$) located 5' to a CaMV35S minimal promoter. The CaMV35S minimal promoter is located 5' to the MEA coding sequence. A DNA fragment encoding fifteen glycine residues is present, in frame, at the 3' end of the UAS-MEA DNA sequence, followed, in frame, by a DNA fragment encoding an *Arabidopsis* homologue of ESA1.

The AtESA1 coding sequence was fused to the 3'-end of the MEA coding sequence by standard cloning techniques. Two intermediate PCR products were generated for this purpose. The first intermediate product contained the MEA coding sequence, flanked on either side by a BamHI restriction site. The BamHI sites were generated by incorporation into the PCR primer sequences. The first intermediate PCR product was digested with BamHI restriction enzyme and was cloned into the T-DNA expression vector pCRS304-5USAL at its unique BamHI site. The resultant plasmid was named pCRS304-5USAL-MEA-no 3'UTR.

The second intermediate PCR product contained a coding sequence for AtESA1 having a 15-glycine spacer (SEQ ID NO:43) fused to its amino terminus. The second intermediate PCR product was generated using two synthetic oligonucleotides and the pAtESA1-cDNA template (Ceres clone ID: 266771). The second PCR product was flanked by a unique SmaI site at its 5' end and by a unique XhoI site at its 3' end. These cloning sites were generated by incorporation into the PCR primer sequences. The second PCR product was digested with SmaI and XhoI, and was cloned into the plasmid pCRS304-5USAL-MEA-no 3'UTR between the unique restriction sites SmaI and XhoI. The resultant plasmid was named pCRS304-5USAL-MEA-ESA1. The transgene was designated MEA-15G-ESA1. The amino acid sequence of the chimeric polypeptide encoded by the transgene is shown in SEQ ID NO:15 and the nucleotide sequence of the transgene is shown in SEQ ID NO:16.

Thus, pCRS304-5UAS-MEA-15G-ESA1 encodes a chimeric polypeptide having an *Arabidopsis thaliana* MEA polypeptide and an *Arabidopsis thaliana* HAT polypeptide, joined by an intervening peptide spacer of 15 glycine residues (SEQ ID NO:43). The plasmid contains 5 copies of the Gal4 upstream activator sequence ($UAS_{GAL4}$) located 5' and operably linked to the CaMV35S minimal promoter. This in turn is located 5' and operably linked to the MEA-15G-ESA1 coding sequence. The binding of a transcription factor that possesses a Gal4 DNA binding domain to the Gal4 UAS is necessary for transcriptional activation.

Example 11

This example demonstrates transgenic plants comprising chimeric HAT nucleic acid constructs.

The pCRS304-5UAS-FIE-15G-ESA1 plasmid and the pCRS304-5UAS-MEA-15G-ESA1 were independently introduced into *Arabidopsis* WS by *Agrobacterium tumefaciens* mediated transformation using the floral infiltration technique essentially as described in Bechtold, N. et al., *C.R. Acad. Sci. Paris,* 316:1194-1199 (1993). Several transformed plants, designated FE #1, FE #2, and ME #1, were selected for further study. The FIE-15G-ESA1 gene and the MEA-5 G-ESA1 gene were then transcriptionally activated in specific target cells and tissues by crossing with two-component enhancer trap lines expressing a chimeric Gal4-VP16 activator protein (Haseloffet al.). In each activator line there is also a $UAS_{GAL4}$-GFP (green fluorescent protein) reporter gene.

Example 12

This example demonstrates two-component activation lines.

The two-component system for activating target gene expression was first utilized in *drosophila* and subsequently adopted for use in plants (see Bennett et al. (1998) U.S. Pat. No. 5,801,027; Liu et al. (1999) U.S. Pat. No. 5,968,793); Bennett et al. (2000) U.S. Pat. No. 6,127,606; Haseloff and Hodge (2001) U.S. Pat. No. 6,255,558). The two-component system typically consists of two independent transcription units: an activator gene and a target gene. The activator gene encodes a transcriptional activator, a DNA binding protein gene such as Gal4-VP16, operably linked to a plant or animal promoter. The target gene has a protein coding sequence, such as a cDNA, operably linked to a promoter that has multiple copies of an upstream activator sequence element ($UAS_{GAL4}$) to which the transcriptional activator protein can bind. A target gene can be activated genetically by crossing a target gene-containing plant with an activation gene-containing plant (i.e., from an "activator line"). Alternatively, a target gene in a cell, tissue, or whole organism can be activated by transforming with an activation gene containing vector.

An extensive collection of *Arabidopsis* two-component activation lines has been produced and described by Dr. Jim Haseloff et al. (see the website for plantsci.cam.ac.uk/Haseloff/IndexCatalogue.html), and individual lines are available from the *Arabidopsis* Biological Resource Center (see the website for *Arabidopsis*.org/abrc/haseloff.htm. The activator lines were produced using a T-DNA based enhancer trap strategy. In this system the Gal4-VP 16 gene containing a CaMV35S minimal promoter can be transcriptionally activated when T-DNA is inserted proximal to an endogenous enhancer element. Enhancer activity is revealed by the trans-activation of a UAS.sub.GAL4-GFP reporter gene. Each activation line in the Haseloff collection contains one or more random T-DNA insertions in the *Arabidopsis* genome resulting in cell, tissue, or organ specific expression of a UAS.sub.GAL4-GFP reporter gene. The amino acid sequence of the GAL4.sub.UAS-VP16 activator protein is shown in Table 8.

Six publicly available *Arabidopsis* two-component activation lines are described in Table 4 including J2592, J0661, Q2500, M0164, J2301 and J2921.

TABLE 4

| Haseloff activation line reference number and ABRC seed stock number | Ovule and seed development | Root | Other | GFP Intensity |
|---|---|---|---|---|
| J2592 (CS9180) | Prefertilization ovule: ovule, funiculus and placenta. Developing seed: developing embryo and mature embryo. | Root cap, root epidermal cells. | Seedling: shoot and root epidermis, root cortex and root cap; hypocotyl, petiole epidermis, expanded cotyledon and leaf vasculature; stem epidermis and rosette leaf vasculature. Flower: sepal, petal and ovary vasculature; epidermis of mature sepal, petal, filament and ovary; stigma. | Medium |
| M0164 (CS9307) | Mature embryo. | Root: weak patchy expression in vasculature of primary root. | Seedling: strong in shoot apex, rosette leaf and petiole vasculature. Weak in cotyledon vasculature. Silique: older siliques only. | High |
| Q2500 (CS9135) | Ovule: prefertilization ovule. Seed: chalazal end of developing seed, seed coat and young embryo. | Root: vasculature. | Seedling: vasculature of hypocotyl, expanded cotyledons and first leaves. Flower: petal vasculature, placenta. | High |
| J0661 (CS9141) | Developing seed: funiculus, embryo. | Root: root vasculature. | Seedling: vasculature including root, hypocotyl, expanded cotyledons, rosette leaf vasculature, petiole. Cauline leaf vasculature. Flower: floral organ vasculature including pedicel, sepal, petal, filament and pistil. | Medium |
| J2921 (CS9194) | | Root: weak patchy expression in root; weak in root hair; strong in root vasculature and root tip; strong in junctions where lateral roots form. | Flower: broad expression in epidermis of immature buds; GFP decreases and becomes restricted to the ovary as the flower matures; weak expression in sepal and petal vasculature. | Medium |
| J2301 (CS9173) | Seed: seedcoat; GFP increases as silique matures; GFP detectable at suspensor end of embryo. | Root: very strong in root tip; weak in root cortex; root epidermis. | Seedling: weak throughout seedling vasculature; strong in leaf trichomes; also detected in atrichoblasts. Flower: base of sepal and petal, ovary epidermis, style. | Medium |

Each activation line displays a characteristic pattern of GFP accumulation in seedlings, vegetative organs and reproductive organs. GFP images are publicly available at http://www/plantsci.cam.ac.uk./Haseloff/GAL4 and were independently confirmed. For example, in line J2592 GFP expression was detectable in young seedlings in the shoot and root epidermis, root cortex and root cap but not in the root apical meristem. GFP was also observed in seedling hypocotyl, petiole epidermis, expanded cotyledon, flower axillary buds, flower axilary bud epidermis, and leaf vasculature. Low intensity GFP was detectable in the stem epidermis as well as in rosette and leaf vasculature. GFP was observed in J2592 flowers including the vasculature of the sepal, petal and ovary and in the epidermis of the mature sepal, petal, filament, ovary and in stigmatic papillae. The intensity of GFP decreases as the flowers mature. A low level of GFP was detected in the pedicel. GFP was observed in pre- and post-fertilization ovules and in the funiculus and placenta. In fertilized seed GFP was detectable in developing seeds and in mature embryos. GFP expression patterns were observed to vary in some progeny of J2592.

In line M0164 seedlings GFP expression was observed in the vasculature of the primary root. No expression was detectable in the root cap. Relatively intense GFP expression was observed in the shoot apex and in leaf and petiole vasculature. Low intensity GFP expression was observed in the cotyledon vasculature. In developing seed GFP was detectable in embryos. GFP expression was also observed in seeds, in mature, brown, siliques and mature embryos. GFP expression was not detectable in the seed coat or endosperm.

Example 13

This example demonstrates FIE-15G-ESA1 activated plants.

The FIE-15G-ESA1 transgene was transcriptionally activated by crossing FE #1 and FE #2 plants with the GAL4-VP16 two-component activation lines described in Table 3. Reciprocal crosses were carried out using FE #1 and FE #2 plants with each 2-component activation line. The seed produced in such a cross are referred to as $F_1$ seed. Thus, a first generation seed or plant produced by crossing FE #1 as the mother with J2592 as the pollen donor is referred to as $F_1$ (FE #1×J2592). A second generation seed or plant produced by self pollination of $F_1$ (FE #1×J2592) is referred to as $F_2$ (FE #1×J2592). $F_1$ seed produced by crossing FE #1 and FE #2 with the activation lines described above were collected from mature siliques or seed pods and dried using standard Arabidopsis procedures. These siliques typically contained mature seed, abnormal seed and aborted ovules.

To analyze the effect of FIE-15G-ESA1 expression on Arabidopsis development F1 seed and seed from control plants were germinated on agar plates containing 1× Murashige and Skoog (MS) salts and 1 percent sucrose using standard Arabidopsis procedures. Germinated seedlings were scored 8 days after plating for germination efficiency, the presence or absence of the activator gene (inferred from GFP reporter gene activity) and seedling phenotypes. After phenotyping, F1 seedlings were transferred to soil at the four rosette leaf stage and then grown under standard Arabidopsis greenhouse conditions. Flowering plants were tested by PCR for the presence of the FIE-15G-ESA1 target gene and scored again for GFP expression.

When line J2592 was used as the activation line, 86 percent of the $F_1$ seeds germinated normally. $F_1$ seedlings and plants exhibited both vegetative and reproductive effects of FIE-15G-ESA1 activity. For example, cotyledons were observed to be incomplete, cupped, or missing in 30 percent of all seedlings analyzed. In some instances, extra cotyledons were observed. Hypocotyl development was perturbed in twelve percent of all $F_1$ seedlings analyzed. Finally, twenty-four percent of $F_1$ seedlings displayed stunted or missing petioles. Developmental abnormalities resulted in the loss of some seedlings from the study. These phenotypes were not observed in seedlings produced by selfing J2592, FE #1, or FE #2. Nor were these phenotypes observed in seedlings produced by crossing these parents with a wild type plant. The results indicate that activation of FIE-15G-ESA1 by J2592 is responsible for these diverse traits.

When activation line M0164 was used to activate FIE-15G-ESA1, ninety-seven percent of the $F_1$ (M0164×FE #1) seed germinated successfully. Forty percent of $F_1$ seedlings analyzed showed vegetative defects including cotyledons that were incomplete, cupped, or missing. In some instances, extra cotyledons were observed. Thus, the F1 seedling phenotypes induced using FIE-15G-ESA1 were not restricted to the J2592 activation line.

Reproductive phenotypes for $F_1$ plants containing activator and FIE-15G-ESA1 target genes were analyzed as described in Ohad, N., et al. (1999) *The Plant Cell* 11:407-415; and in Fischer, R. L., et al., (2001) U.S. Pat. No. 6,229,064. In brief, developing siliques were sampled along the primary inflorescence proximal to distal relative to the rosette leaves. Within each silique, the seed were classified according to the color and the status of endosperm and embryo development. Since $F_1$ seed are the product of genetic crossing, each silique that is produced by an $F_1$ plant should contain a population of $F_2$ seed that segregate for the activator and target genes and any resulting phenotype. Thus, each silique contains a population of wild type seed that provide a developmental reference for staging seed development and phenotyping. Seed phenotypes were recorded at two stages of seed development: (i) when the majority of seed in a silique were at the mature seed stage of embryo development, and (ii) at the torpedo to walking stick stage of embryo development. At maturity, seeds were collected and stored under standard conditions.

Effect of FIE-15G-ESA1 gene activity on seed development: $F_2$ seeds were produced by $F_1$ plants through self-pollination. $F_2$ (FE #1×J2592) and $F_2$ (FE #2×J2592) seed development was characterized using a Zeiss dissecting microscope and a Zeiss Axioskope microscope as described by Ohad, N., et al., (1999) *The Plant Cell* 11:407-415 using standard Arabidopsis procedures.

Activation of FIE-15G-ESA1 by J2592 altered embryo and seed development as shown in Table 5. Self-pollinated $F_1$ (FE #1×J2592) plants produced two classes of seed, (i) those exhibiting normal embryo and seed development, and (ii) those exhibiting abnormal seed and embryo development. Abnormal seed were found to contain an embryo whose development was arrested at the transition between heart and torpedo stages of development. By contrast, endosperm production was not arrested in abnormal seed but was greater than or equal to that observed in normal seed. Thus, FIE-15G-ESA1 was observed to alter the balance between endosperm and embryo development within the seed. Most abnormal seed abort and degenerate into shrunken seed. The percent abnormal to normal seed ranged from 25-62 percent (see Table 5). Similar results were obtained when the reciprocal cross (i.e., J2592×FE #1) was performed. FIE-15G-ESA1 also was observed to alter seed development when J0661 was crossed with FE #1. By contrast, no abnormal seed were detected in $F_1$ plants produced by crossing Q2500, J2301 or J2921 with FE #1. In fact, more than 98 percent of seed from self-pollinated FE #1, FE #2 and J2592 parental lines had no visually observable abnormalities. Thus, the effect of FIE-15G-ESA1 activity on seed development appears to be promoter dependent.

TABLE 5

Segregation of seed phenotypes in developing siliques

| F1(FE#1 × J2592) Plant #29 | | | F1(FE#1 × J2592) Plant #31 | | |
|---|---|---|---|---|---|
| | Normal seeds | Shrunken aborted seeds | | Normal seeds | Shrunken aborted seeds |
| Total | 225 | 683 | Total | 264 | 760 |
| Percent | 25.6 | 74.4 | | 25.8 | 74.2 |

| F1(FE#1 × J2592) Plant #35 | | |
|---|---|---|
| | Normal seeds | Shruken aborted seeds |
| Total | 264 | 760 |
| Percent | 25.8 | 74.2 |

| F1(FE#1 × J2592) Plant #35 | | | F1(FE#1 × J2592) Plant #26 | | |
|---|---|---|---|---|---|
| | Normal seeds | Shrunken aborted seeds | | Normal seeds | Shrunken aborted seeds |
| Total | 361 | 136 | Total | 379 | 151 |
| Percent | | 37.7 | Percent | | 39.8 |
| STD* | | 3.8 | STD | | 4.1 |

| F1(FE#1 × J2592) Plant #29 | | | F1(FE#1 × J2592) Plant #37 | | |
|---|---|---|---|---|---|
| | Normal seeds | Shrunken aborted seeds | | Normal seeds | Shrunken aborted seeds |
| Total | 355 | 115 | Total | 369 | 125 |
| Percent | | 32.40 | Percent | | 33.9 |
| STD | | 3.40 | STD | | 2.7 |

| F1(FE#1 × J2592) Plant #31 | | | F1(FE#1 × J2592) Plant #32 | | |
|---|---|---|---|---|---|
| | Normal seeds | Shrunken aborted seeds | | Normal seeds | Shrunken aborted seeds |
| Total | 364 | 111 | Total | 308 | 192 |
| Percent | | 30.5 | Percent | | 62.3 |
| STD | | 2.1 | STD | | 5.2 |

*STD = standard deviation

Example 14

This example demonstrates MEA-15G-ESA1 activated plants

The MEA-15G-ESA1 transgene was transcriptionally activated by crossing ME #1 with J2592, J0661 and Q2500 (see Table 5). Reciprocal crosses between ME #1 and each activation line also were made. $F_1$ seeds were collected at maturity and stored under standard conditions. To analyze the effect of MEA-15G-ESA1 expression on *Arabidopsis* development $F_1$ seed and seed from control plants were germinated on agar plates containing 1×MS salts and 1 percent sucrose. Subsequently, plants were phenotyped as described in Example 13. Mature plants were tested for the presence of MEA-15G-ESA1 by PCR.

When J2592 or Q2500 were crossed with ME #1 (pCRS304-5UAS-MEA-15 G-ESA1 transformed plant #1) the $F_1$ seedlings displayed vegetative effects of MEA-15 G-ESA1 activity similar to those observed in seed produced by (FE #1×J2592) and (FE #1×-15G-ESA1). For example, the cotyledons of F1 seedlings were observed to be incomplete, cupped, or missing. Hypocotyl development also was perturbed. These phenotypes were not observed in seedlings produced by the self pollination of J2592, Q2500 or ME #1. Thus, activation of MEA-15G-ESA1 by J2592 and Q2500 is responsible for these vegetative developmental effects.

TABLE 6

Segregation of seed phenotypes in developing siliques

| Cross ID | Line ID | # Green seed | # White seed | # Aborted ovules | Total seeds |
|---|---|---|---|---|---|
| F1(ME #1 × J2592) | Plant #1 | | | | |
| | AVG | 17.4 | 6 | 14.4 | 37.8 |
| | % | 46.0 | 15.9 | 38.1 | 100 |
| F1(ME #1 × J2592) | Plant #2 | | | | |
| | AVG | 17.2 | 6.3 | 15.9 | 39.4 |
| | % | 43.7 | 16.0 | 40.4 | 100 |

TABLE 6-continued

Segregation of seed phenotypes in developing siliques

| Cross ID | Line ID | | # Green seed | # White seed | # Aborted ovules | |
|---|---|---|---|---|---|---|
| F1(ME #1 × J2592) | Plant #3 | | | | | |
| | | AVG | 23 | 0 | 15 | 38 |
| | | % | 60.5 | 0.0 | 39.5 | 100 |
| F1(ME #1 × J2592) | Plant #22 | | | | | |
| | | AVG | 18.5 | 5.9 | 14.8 | 39.2 |
| | | % | 47.2 | 15.1 | 37.8 | 100 |
| F1(ME #1 × J2592) | Plant #24 | | | | | |
| | | AVG | 24.6 | 0 | 15.5 | 40.1 |
| | | % | 61.3 | 0.0 | 38.7 | 100 |
| Control (GFP negative) | Plant #26 | | | | | |
| | | AVG | 43.2 | 0 | 0.2 | 43.4 |
| | | % | 99.5 | 0.0 | 0.5 | 100 |
| | | | | | | Total est. |
| F1(J2592 × ME #1) | Plant #14 | | | | | |
| | | AVG | 24.2 | 0.1 | 14.8 | 39.1 |
| | | % | 61.9 | 0.3 | 37.9 | 100 |
| F1(J2592 × ME #1) | Plant #26 | | | | | |
| | | AVG | 15 | 6.2 | 16 | 37.2 |
| | | % | 40.3 | 16.7 | 43.0 | 100 |
| F1(J2592 × ME #1) | Plant #34 | | | | | |
| | | AVG | 15.9 | 6.7 | 15.2 | 37.8 |
| | | % | 42.1 | 17.7 | 40.2 | 100 |
| F1(ME #1 × J0661) | Plant #32 | | | | | |
| | | AVG | 15.9 | 0 | 12.4 | 28.3 |
| | | % | 56.2 | 0.0 | 43.8 | |
| F1(J0661 × ME #1) | Plant #19 | | | | | |
| | | AVG | 17.8 | 0 | 17.5 | 35.3 |
| | | % | 50.4 | 0.0 | 49.6 | |
| F1(J0661 × ME #1) | Plant #27 | | | | | |
| | | AVG | 18.6 | 0 | 15.4 | 34 |
| | | % | 54.7 | 0.0 | 45.3 | |
| F1(J0661 × ME #1) | Plant #28 | | | | | |
| | | AVG | 18.2 | 0.1 | 16.8 | 35.1 |
| | | % | 51.9 | 0.3 | 47.9 | |

Example 15

This example demonstrates fertilization independent seed development.

To determine the frequency of post-fertilization seed abortion, siliques harvested at two weeks and at four weeks after self-pollination were dissected, and wild-type and aborted seeds were counted. To test for fertilization-independent development, flower buds from plants that had not yet begun to shed pollen (i.e., stage 12 plants) (see Smyth, D. R., et al., *Plant Cell,* 2: 755-761 (1990)) were opened, immature anthers were removed, and the flower bud was covered with a plastic bag. In some experiments, the silique was measured, dissected, and the number of seed-like structures and degenerated ovules were counted after seven days. In some experiments, the silique was harvested and ovules and seed-like structures were phenotyped after 15 days.

When immature $F_1$(J2592×FE #1) flowers were emasculated and allowed to develop, seed-like structures were observed that were filled with endosperm but contained no embryo. This occurred in roughly 40 percent of the siliques analyzed. Thus, activation of FIE-15G-ESA1 by J2592 also can induce fertilization independent endosperm and seed development.

Example 16

The example demonstrates profiling gene expression.

This example demonstrates the use of chimeric HAT polypeptides for identifying genes that are coordinately repressed or coordinately activated in specific tissues and at specific times during development. Gene activity during fruit and seed development was compared between wild type *Arabidopsis*, fie mutant *Arabidopsis*, and $F_1$ (J2592×FE #1) plants using microarray expression analysis.

Developing fruit and seed from wildtype, fie mutant, and $F_1$ plants were collected. Total RNA was extracted from fruit 0-5 mm in length, 5-10 mm in length, and fruit greater than 10 mm in length from each plant. RNA was extracted using Triazol essentially as described by the supplier (Invitrogen, Carlsbad, Calif.). Poly(A+) mRNA is isolated using standard procedures and 2 ug from each sample is used to generate labeled probes for hybridization to microarray slides containing *Arabidopsis* cDNA sequences. The *Arabidopsis* microarray contains nucleic acid features representing 10,000 different *Arabidopsis* genes. Hybridization experiments to detect differentially regulated genes were set up in pairs. For example, RNA from 0-5, 5-10 and greater than 10 mm wild type fruit and seed was compared to RNA from 0-5, 5-10 and greater than 10 mm $F_1$ (J2592×FE #1) fruit and seed. Expression results are analyzed using standard software and procedures. DNA sequences of genes whose expression is increased or decreased in FIE-15G-ESA1-activated progeny was compared to control plants is used to identify common cis-acting elements.

Sample preparation: Seeds of *Arabidopsis thaliana* plants were sterilized in 95% bleach for 1 minute and with 70% ethanol for 45 seconds and subsequently washed 5 times in sterile distilled deionized water and then plated on MS agar plates and left at 4° C. for 4 days to be vernalized. Plates were placed in growth chamber with 16 hr light/8 hr. dark, 23° C., 14,500-15,900 LUX, and 70% relative humidity for germination and growth. Seedlings could be PCR-genotyped for the presence of the transgene and analyzed using dissecting microscopy for GFP expression before they were individually transplanted into soil. Immature floral buds and mature flowers were harvested with forceps and flash frozen in liquid nitrogen and stored at −80° C. until use. Total RNA was extracted using Qiagen Kit and dissolved in RNA-free water.

Slide preparation: Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot will have a corresponding ratio of fluorescence that represents the level of disparity between the respective mRNA species in the two sample pools. Thousands of polynucleotides can be spotted on one slide, and each experiment analyzes the expression pattern of thousands of mRNA species.

The microarray utilizes a chemically coated microscope slide, referred herein as a "chip" with numerous polynucleotide samples arrayed at a high density. The coating with chemicals such as Poly-L-lysine allows for spotting DNA at high density by providing a hydrophobic surface, reducing the spreading of spots of DNA solution arrayed on the slides. Glass microscope slides (Gold Seal #3010 manufactured by Gold Seal Products, Portsmouth, N.H., USA) were coated with a 0.1% W/V solution of Poly-L-lysine (Sigma, St. Louis, Mo.) using the following protocol:

Slides were placed in slide racks (Shandon Lipshaw #121). The racks were then put in chambers (Shandon Lipshaw #121). Cleaning solution was prepared by dissolving 70g NaOH in 280 mL ddH2O. 420 mL 95% ethanol was added. The total volume was 700 mL (=2×350 mL); it was stirred until completely mixed. If the solution remained cloudy, ddH$_2$O was added until clear. The cleaning solution was poured into chambers with slide racks; the chambers were covered with glass lids. The solution was mixed on an orbital shaker for 2 hr. The racks were quickly transferred to fresh chambers filled with ddH$_2$O. They were rinsed vigorously by plunging racks up and down. Rinses were repeated 4× with fresh ddH$_2$O each time, to remove all traces of NaOH-ethanol. Poly-L-lysine solution was prepared by adding 70 mL poly-L-lysine stock solution to 70 mL tissue culture PBS in 560 mL double-distilled deionized water using plastic graduated cylinder and beaker. Slides were transferred to polylysine solution and shaken on an orbital shaker for 1 hr. The rack was transferred to a fresh chambers filled with ddH$_2$O. It was plunged up and down 5× to rinse. The slides were centrifuged on microtiter plate carriers (paper towels were placed below the rack to absorb liquid) for 5 min. @ 500 rpm. The slide racks were transferred to empty chambers with covers. Slide racks were dried in a 45C oven for 10 min. The slides were stored in a closed plastic slide box in the dark. Normally, the surface of lysine coated slides was not very hydrophobic immediately after this process, but became increasingly hydrophobic with storage. A hydrophobic surface helped ensure that spots didn't run together while printing at high densities. After they aged for 10 days to a month the slides were ready to use. However, coated slides that have been sitting around for long periods of time were usually too old to be used. This was because they developed opaque patches, visible when held to the light, and these resulted in high background hybridization from the fluorescent probe.

Alternatively, precoated glass slides were purchased from TeleChem International, Inc. (Sunnyvale, Calif., 94089; catalog number SMM-25, Superamine substrates).

PCR amplification of cDNA clones: Polynucleotides were amplified from *Arabidopsis* cDNA clones using one insert specific primer and one common primer that hybridized to the cloning site. The resulting 100 ul PCR reactions were purified with Qiaquick 96 PCR purification columns (Qiagen, Valencia, Calif., USA) and eluted in 30 uL of 5 mM Tris. 8.5 uL of the elution were mixed with 1.5 uL of 20×SSC to give a final spotting solution of DNA in 3×SSC. The concentrations of DNA generated from each clone varied between 10-100 ng/ul, but were usually about 50 ng/ul.

Arraying PCR products on slides: Purified PCR products were spotted onto the poly-L-Lysine coated glass slides using an arrangement of quill-tip pins (ChipMaker 3 spotting pins; Telechem International, Inc., Sunnyvale, Calif., USA) and a robotic arrayer (PixSys 3500, Cartesian Technologies, Irvine, Calif., USA). Approximately 0.5 nl of a prepared PCR product was spotted at each location to produce spots with approximately 100 um diameters. Spot center-to-center spacing was from 180 um to 210 um depending on the array. Printing was conducted in a chamber with relative humidity set at 50%. Slides containing maize sequences were purchased from Agilent Technology (Palo Alto, Calif. 94304).

Slide processing: After arraying, slides were processed through a series of steps prior to hybridization: rehydration, UV cross-linking, blocking and denaturation. Slides were rehydrated by placing them over a beaker of warm (55C) water (DNA face down), for 2-3 sec, to distribute the DNA more evenly within the spots, and then snap dried on a hot plate (DNA side, face up). The DNA was then cross-linked to the slides by UV irradiation (60-65 mJ; 2400 Stratalinker, Stratagene, La Jolla, Calif., USA). The blocking step was performed to modify remaining free lysine groups, and hence minimize their ability to bind labeled probe DNA. To achieve this the arrays were placed in a slide rack. An empty slide chamber was left ready on an orbital shaker. The rack was bent slightly inwards in the middle, to ensure the slides would not run into each other while shaking. The blocking solution was prepared as follows:

Three 350-ml glass chambers (with metal tops) were set to one side, and a large round Pyrex dish with dH$_2$O was placed ready in the microwave. At this time, 15 ml sodium borate was prepared in a 50 ml conical tube. 6 g succinic anhydride was dissolved in approx. 325-350 mL 1-methyl-2-pyrrolidinone. Rapid addition of reagent was important. Immediately after the last flake of the succinic anhydride dissolved, the 15-mL sodium borate was added. Immediately after the sodium borate solution mixed in, the solution was poured into an empty slide chamber. The slide rack was plunged rapidly and evenly in the solution. It was vigorously shaken up and down for a few seconds, making sure slides never left the solution. It was mixed on an orbital shaker for 15-20 min. Meanwhile, the water in the Pyrex dish (enough to cover slide rack) was heated to boiling. Following this, the slide rack was gently plunged into the 95C water (just stopped boiling) for 2 min. Then the slide rack was plunged in 5× in 95% ethanol. The slides and rack were centrifuged for 5 min. @ 500 rpm. The slides were loaded quickly and evenly onto the carriers to avoid streaking. The arrays were used immediately or were stored in a slide box.

Hybridization: The hybridization process began with the isolation of mRNA from the two tissues (see "Isolation of total RNA" and "Isolation of mRNA," below) followed by their conversion to single stranded cDNA (see "Generation of probes for hybridization", below). The cDNA from each tissue was independently labeled with a different fluorescent dye and then both samples were pooled together. This final differentially labeled cDNA pool was then placed on a processed microarray and allowed to hybridize (see "Hybridization and wash conditions", below).

Isolation of mRNA: mRNA was isolated using the Qiagen Oligotex mRNA Spin-Column protocol (Qiagen, Valencia, Calif.). Briefly, 500 µl OBB buffer (20 mM Tris-Cl, pH 7.5, 1 M NaCl, 2 mM EDTA, 0.2% SDS) was added to 500 µl of total RNA (0.5-0.75 mg) and mixed thoroughly. The sample was first incubated at 70° C. for 3 min, then at room temperature for 10 minutes and finally centrifuged for 2 min at 14,000-18,000×g. The pellet was resuspended in 400 µl OW2 buffer (10 mM Tris-Cl, pH 7.5, 150 mM NaCl, 1 mM EDTA) by vortexing, the resulting solution placed on a small spin column in a 1.5 ml RNase-free microcentrifuge tube and centrifuged for 1 min at 14,000-18,000×g. The spin column was transferred to a new 1.5 ml RNase-free microcentrifuge tube and washed with 400 µl of OW2 buffer. To release the isolated mRNA from the resin, the spin column was again transferred to a new RNase-free 1.5 ml microcentrifuge tube, 20-100 µl 70° C. OEB buffer (5 mM Tris-Cl, pH 7.5) added and the resin resuspended in the resulting solution via pipeting. The mRNA solution was collected after centrifuging for 1 min at 14,000-18,000×g.

Alternatively, mRNA was isolated using the Stratagene Poly(A) Quick mRNA Isolation Kit (Startagene, La Jolla, Calif.). Here, up to 0.5 mg of total RNA (maximum volume of 1 ml) was incubated at 65° C. for 5 minutes, snap cooled on ice and 0.1× volumes of 10× sample buffer (10 mM Tris-HCl (pH 7.5), 1 mM EDTA (pH 8.0) 5 M NaCl) added. The RNA sample was applied to a prepared push column and passed through the column at a rate of ~1 drop every 2 sec. The solution collected was reapplied to the column and collected as above. 200 µl of high salt buffer (10 mM Tris-HCl (pH 7.5), 1 mM EDTA, 0.5 NaCl) was applied to the column and passed through the column at a rate of ~1 drop every 2 sec. This step was repeated and followed by three low salt buffer (10 mM Tris-HCl (pH 7.5), 1 mM EDTA, 0.1 M NaCl) washes preformed in a similar manner. mRNA was eluted by applying to the column with four separate 200 µl aliquots of elution buffer (10 mM Tris-HCl (pH 7.5), 1 mM EDTA) preheated to 65° C. Here, the elution buffer was passed through the column at a rate of 1 drop/sec. The resulting mRNA solution was precipitated by adding 0.1× volumes of 10× sample buffer, 2,5 volumes of ice-cold 100% ethanol, incubating overnight at −20° C. and centrifuging at 14,000-18,000×g for 20-30 min at 4° C. The pellet was washed with 70% ethanol and air dried for 10 min. at room temperature before resuspension in RNase-free deionized water.

Preparation of Yeast control mRNA: Plasmid DNA was isolated from the following yeast clones using Qiagen filtered maxiprep kits (Qiagen, Valencia, Calif.): YAL022c (Fun26), YAL031c(Fun21), YBR032w, YDL131w, YDL182w, YDL194w, YDL196w, YDR050c and YDR116c. Plasmid DNA was linearized with either BsrBI (YAL022c(Fun26), YAL031c(Fun21), YDL131w, YDL182w, YDL194w, YDL196w, YDR050c) or AflIII (YBR032w, YDR116c) and isolated.

The following solution was incubated at 37° C. for 2 hours: 17 µl of isolated yeast insert DNA (1 µg), 20 µl 5× buffer, 10 µl 100 mM DTT, 2.5 µl (100 U) RNasin, 20 µl 2.5 mM (ea.) rNTPs, 2.7 µl (40U) SP6 polymerase and 27.8 µl RNase-free deionized water. 2 µl (2 U) Ampli DNase I was added and the incubation continued for another 15 min. 10 µl 5M $NH_4OAC$ and 100 µl phenol:chloroform:isoamyl alcohol (25:24:1) were added, the solution was vortexed and then centrifuged to separate the phases. To precipitate the RNA, 250 µl ethanol was added and the solution incubated at −20° C. for at least one hour. The sample was then centrifuged for 20 min at 4° C. at 14,000-18,000×g, the pellet washed with 500 µl of 70% ethanol, air dried at room temperature for 10 min and resuspended in 100 µl of RNase-free deionized water. The precipitation procedure was then repeated.

Alternatively, after the two-hour incubation, the solution was extracted with phenol/chloroform once before adding 0.1 volume 3M sodium acetate and 2.5 volumes of 100% ethanol. The solution was centrifuged at 15,000 rpm, 4° C. for 20 minutes and the pellet resuspended in RNase-free deionized water. The DNase I treatment was carried out at 37° C. for 30 minutes using 2 U of Ampli DNase I in the following reaction condition: 50 mM Tris-HCl (pH 7.5), 10 mM $MgCl_2$. The DNase I reaction was then stopped with the addition of $NH_4OAC$ and phenol:chloroform:isoamyl alcohol (25:24:1), and RNA isolated as described above.

0.15-2.5 ng of the in vitro transcript RNA from each yeast clone were added to each plant mRNA sample prior to labeling to serve as positive (internal) probe controls.

Generation of labeled probes for hybridization from first-strand cDNA: Hybridization probes were generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo(dT)$_{18}$ primer d(TTTTTTTTTTTTTTTTTTV) (SEQ ID NO:44) was mixed with Poly A+mRNA (1.5-2 µg mRNA isolated using the Qiagen Oligotex mRNA Spin-Column protocol or-the Stratagene Poly(A) Quik mRNA Isolation protocol (Stratagene, La Jolla, Calif., USA) in a total volume of 25 µl. The sample was incubated in a thermocycler at 70° C. for 5 min, cooled to 48° C. and 10 µl of 5× cDNA Synthesis Buffer (kit supplied), 5 µl 10× dNTP mix (dATP, dCTP, dGTP, dTTP and aminoallyl-dUTP; kit supplied), 7.5 µl deionized water and 2.5 µl MMLV Reverse Transcriptase (500 U) added. The reaction was then incubated at 48° C. for 30 minutes, followed by 1 hr incubation at 42° C. At the end of the incubation the reaction was heated to 70° C. for 10 min, cooled to 37° C. and 0.5 μl (5 U) RNase H added, before incubating for 15 min at 37° C. The solution was vortexed for 1 min after the addition of 0.5 μl 0.5 M EDTA and 5 μl of QuickClean Resin (kit supplied) then centrifuged at 14,000-18,000×g for 1 min. After removing the supernatant to a 0.45 μm spin filter (kit supplied), the sample was again centrifuged at 14,000-18,000×g for 1 min, and 5.5 μl 3 M sodium acetate and 137.5 μl of 100% ethanol added to the sample before incubating at −20° C. for at least 1 hr. The sample was then centrifuged at 14,000-18,000×g at 4° C. for 20 min, the resulting pellet washed with 500 μl 70% ethanol, air-dried at room temperature for 10 min and resuspended in 10 μl of 2× fluorescent labeling buffer (kit provided). 10 μl each of the fluorescent dyes Cy3 and Cy5 (Amersham Pharmacia, Piscataway, N.J., USA); prepared according to Atlas™ kit directions of Clontech) were added and the sample incubated in the dark at room temperature for 30 min. to 1 hr. The fluorescently labeled first strand cDNA was precipitated by adding 2 μl 3M sodium acetate and 50 μl 100% ethanol, incubated at −20° C. for at least 2 hrs, centrifuged at 14,000-18,000×g for 20 min, washed with 70% ethanol, air-dried for 10 min and dissolved in 100 μl of water.

Alternatively, 3-4 μg mRNA, 2.5 (~8.9 ng of in vitro translated mRNA) μl yeast control and 3 μg oligo dTV (TTTTTTTTTTTTTTTTTTT(A/C/G); SEQ ID NO:44) were mixed in a total volume of 24.7 μl. The sample was incubated in a thermocycler at 70° C. for 10 min. before chilling on ice. To this, 8 μl of 5× first strand buffer (SuperScript II RNase H—Reverse Transcriptase kit from Invitrogen, Carlsbad, Calif. 92008; cat no. 18064022), 0.8 μl of aa-dUTP/dNTP mix (50×; 25 mM dATP, 25 mM dGTP, 25 mM dCTP, 15 mM dTTP, 10 mM aminoallyl-dUTP), 4 μl of 0.1 M DTT and 2.5 μl (500 units) of Superscript R.T.II enzyme (Stratagene) were added. The sample was incubated at 42° C. for 2 hours before a mixture of 10° C. of 1M NaOH and 10° C. of 0.5 M EDTA was added. After a 15 minute incubation at 65° C., 25 μl of 1 M Tris pH 7.4 was added. This was mixed with 450 μl of water in a Microcon 30 column before centrifugation at 11,000×g for 12 min. The column was washed twice with 450 μl (centrifugation at 11,000 g, 12 min.) before eluting the sample by inverting the Microcon column and centrifuging at 11,000×g for 20 seconds. Sample was dehydrated by centrifugation under vacuum and stored at −20° C.

Each reaction pellet was dissolved in 9 μl of 0.1 M carbonate buffer (0.1M sodium carbonate and sodium bicarbonate, pH=8.5-9) and 4.5 μl of this placed in two microfuge tubes. 4.5 μl of each dye (in DMSO) were added and the mixture incubated in the dark for 1 hour. 4.5 μl of 4 M hydroxylamine was added and again incubated in the dark for 15 minutes.

Regardless of the method used for probe generation, the probe was purified using a Qiagen PCR cleanup kit (Qiagen, Valencia, Calif., USA), and eluted with 100 ul EB (kit provided). The sample was loaded on a Microcon YM-30 (Millipore, Bedford, Mass., USA) spin column and concentrated to 4-5 ul in volume. Probes for the maize microarrays were generated using the Fluorescent Linear Amplification Kit (cat. No. G2556A) from Agilent Technologies (Palo Alto, Calif.).

Hybridization Conditions: Labeled probe was heated at 95° C. for 3 min and chilled on ice. Then 25 μl of the hybridization buffer which was warmed at 42C was added to the probe, mixing by pipetting, to give a final concentration of: 50% formamide, 4×SSC, 0.03% SDS, 5× Denhardt's solution, and 0.1 μg/ml single-stranded salmon sperm DNA. The probe was kept at 42C. Prior to the hybridization, the probe was heated for 1 min., added to the array, and then covered with a glass cover slip. Slides were placed in hybridization chambers (Telechem International, Sunnyvale, Calif.) and incubated at 42° C. overnight.

Washing conditions: Slides first were washed in 1×SSC+ 0.03% SDS solution at room temperature for 5 minutes. Slides then were washed in 0.2×SSC at room temperature for 5 minutes. Slides finally were washed in 0.05×SSC at room temperature for 5 minutes. Slides then were spun at 800×g for 2 min. to dry. They were then scanned.

Scanning of slides: Chips were scanned using a ScanArray 3000 or 5000 (General Scanning, Watertown, Mass., USA). The chips were scanned at 543 and 633 nm, at 10 μm resolution to measure the intensity of the two fluorescent dyes incorporated into the samples hybridized to the chips.

Data extraction and analysis: The images generated by scanning slides consisted of two 16-bit TIFF images representing the fluorescent emissions of the two samples at each arrayed spot. These images were then quantified and processed for expression analysis using the data extraction software Imagene™ (Biodiscovery, Los Angeles, Calif., USA). Imagene output was subsequently analyzed using the analysis program Genespring™ (Silicon Genetics, San Carlos, Calif., USA). In Genespring, the data was imported using median pixel intensity measurements derived from Imagene output. Background subtraction, ratio calculation and normalization were all conducted in Genespring. Normalization was achieved by breaking the data in to 32 groups, each of which represented one of the 32 pin printing regions on the microarray. Groups consist of 360 to 550 spots. Each group was independently normalized by setting the median of ratios to one and multiplying ratios by the appropriate factor.

Example 17

This example demonstrates analysis of FIE-15G-ESA1 activated plants.

The FIE-15G-ESA1 transgene is transcriptionally activated by crossing FE #1 and FE#2 plants as females to enhancer trap HAP1-VP16 lines that display cell and tissue specific GFP accumulation in vegetative and reproductive organs. FE plants are crossed with four different activation lines. A different enhancer is present in each of the lines and confers expression of the GAL4-VP16 transcription activator, as well as the GFP, in a different set of tissues. The amino acid sequence of the HAP1 portion of the HAP1-VP16 transcription activator is that of the human HAP1 gene. The activity of each enhancer-trap line is inferred from the GFP fluorescence.

At maturity, F₁ seeds are collected and stored under standard conditions. A reciprocal cross is also made, in which FE#1 and FE#2 are used as males.

F₁ seeds are germinated and allowed to self-pollinate. After pollination, some of the embryos and seeds developing on F₁ plants are examined under a microscope. Mature seed are also analyzed as described in Example 11. Seedlings are scored for GFP expression and tested for the presence of FIE-15G-ESA1 by PCR. Phenotypic traits are analyzed as described in Example 13.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

SEQ ID NO:1

FIE coding sequence including the 5' and 3' UTRs. The start and stop codons are in bold.

AAAGGTGAGTTGTGTGTTGTGTCAGGTCCAAAATAAAAGTTTGTCGTGAG
GTCAAAATCTACGGTTACAGTAATTTTAATAACCTGTGAATCTGTGTCTA
ATCGAAAATTACAAAACACCAGTTGTTGTTGCATGAGAGACTTGTGAGCT
TAGATTAGTGTGCGAGAGTCAGACAGAGAGAGATTTCGAATATCGAAT
GTCGAAGATAACCTTAGGGAACGAGTCAATAGTTGGGTCTTTGACTCCAT
CGAATAAGAAATCGTACAAAGTGACGAATAGGATTCAGGAAGGGAAGAAA
CCTTTGTATGCTGTTGTTTTCAACTTCCTTGATGCTCGTTTCTTCGATGT
CTTCGTTACCGCTGGTGGAAATCGGATTACTCTGTACAATTGTCTCGGAG
ATGGTGCCATATCAGCATTGCAATCCTATGCTGATGAAGATAAGGAAGAG
TCGTTTTACACGGTAAGTTGGGCGTGTGGCGTTAATGGGAACCCATATGT
TGCGGCTGGAGGAGTAAAAGGTATAATCCGAGTCATTGACGTCAACAGTG
AAACGATTCATAAGAGTCTTGTGGGTCATGGAGATTCAGTGAACGAAATC
AGGACACAACCTTTAAAACCTCAACTTGTGATTACTGCTAGCAAGGATGA
ATCTGTTCGTTTGTGGAATGTTGAAACTGGGATATGTATTTTGATATTTG
CTGGAGCTGGAGGTCATCGCTATGAAGTTCTAAGTGTGGATTTTCATCCG
TCTGATATTTACCGCTTTGCTAGTTGTGGTATGGACACCACTATTAAAAT
ATGGTCAATGAAAGAGTTTTGGACGTACGTCGAGAAGTCATTCACATGGA
CTGATGATCCATCAAAATTCCCCACAAAATTTGTCCAATTCCCTGTATTT
ACAGCTTCCATTCATACAAATTATGTAGATTGTAACCGTTGGTTTGGTGA
TTTTATCCTCTCAAAGAGTGTGGACAACGAGATCCTGTTGTGGGAACCAC
AACTGAAAGAGAATTCTCCTGGCGAGGGAGCTTCAGATGTTCTATTAAGA
TACCCGGTTCCAATGTGTGATATTTGGTTTATCAAGTTTTCTTGTGACCT
CCATTTAAGTTCTGTTGCGATAGGTAATCAGGAAGGAAAGGTTTATGTCT

GGGATTTGAAAAGTTGCCCTCCTGTTTTGATTACAAAGTTATCACACAAT
CAATCAAAGTCTGTAATCAGGCAAACAGCCATGTCTGTCGATGGAAGCAC
GATTCTTGCTTGCTGCGAGGACGGGACTATATGGCGCTGGGACGTGATTA
CCAAGTAGCGGTCTGAGTCTTGTAGGAATTGATGAATTAGGAGTGCGAAG
AAATGAGATATCCATTCTTTTATTGTAATTCTGATCATGTTGCTACTCCC
TGAGACCTTGAGATGCTCTTTGTAGCCTTGTTAACGTCCACCCTTGTACC
ACAGTGTATACCCTTTCTGGAGATTTTGTCTTATTCTCTTAGTTCAATAC
ACAAGGCTGTATCCTGGAGCTTTATTGCAGGAACCACTCTCTTTCATAAG
CTTTCTAGTATTC

SEQ ID NO:2 (FIE amino acid sequence)

MSKITLGNESIVGSLTPSNKKSYKVTNRIQEGKKPLYAVVFNFLDARFFD
VFVTAGGNRITLYNCLGDGAISALQSYADEDKEESFYTVSWACGVNGNPY
VAAGGVKGIIRVIDVNSETIHKSLVGHGDSVNEIRTQPLKPQLVITASKD
ESVRLWNVETGICILIFAGAGGHRYEVLSVDFHPSDIYRFASCGMDTTIK
IWSMKEFWTYVEKSFTWTDDPSKFPTKFVQFPVFTASIHTNYVDCNRWFG
DFILSKSVDNEILLWEPQLKENSPGEGASDVLLRYPVPMCDIWFIKFSCD
LHLSSVAIGNQEGKVYVWDLKSCPPVLITKLSHNQSKSVIRQTAMSVDGS
TILACCEDGTIWRWDVITK

SEQ ID NO:3 FIE promoter

GAGGAAGCGAGCAAGTACACAACAACCACAAAAGCTTTCAATACTTGTTT
ACTCCTAGGGTTTAAAACTAGAGGTTCTATAGATCTCTAAATTTTTTTGA
ACAAATGTGTTTTCCACACGTGATATTCTACAATACCACTCGAAAATTAT
CCATAATTGCTTTAAACTATTTTTTTGTTTAAATTATATAATTTGTACCG
TTGTAAACTGATTATTTCAAATTATAATTAAAGCACTATAATTTCATATA
TTACATTCAACATATATTAAAATAAACTATAACCATGTATTTTTTTGTCT
TCCTTTCCTATAAACATTGATTGGACTCTATCGTAAATTTTGTCGTTATC
GCAAATTTTGTCGTTATCGATGAGTTTCTCAAAGTTTGGACCTTGATTAT
CTTGTTTGGAGATGTTCAAATCGTTATATCCAAATAGTGAACTTCTAATT
TTCTTTTTTGATAATGTGACTTATTTGGAAAAGTATTCCAAAGTATTCAA
ATAAACCCTTTAAAAATCCATTAAATACATTTTAAATAAGTAAAATGCTC
TCAACGAAGAGATATCATGGTAAATAACAACAGTGAGAGGATAAAATGTT
AAATCAATTTATTTACAACTTCAAATAGGCGGACATCAAACCTACTTAGC
ACACTTTCTATTTTCAAATTGGTTATGGTTTGTCTATTAGTTGTTGCATC
TATGTTTTTAATTCTTATATCGGTGATCTTGATTTTGTTTTGGTGTATC
TAAAATCTATTTTAGTTAAAGTGCAAGAAAATAAAATAAAAACTTAAGGT
AAGAGATGAAAGTAAGCTTTAAATAAAACAGAGCACTTCTATGGTCGATT
ATAGAGCCAAGTTCGTTCCTCCATTTTGGCTTAATGCAATATTACAAGTA
AATCTTATAAAACTTTCCATAAGTATCGTATTACCCATGGATACTATGAT

-continued

ATATAAACTCTCGGAGGTGTAGTCCAGAAGAAATGATCCATATTTGCATA

CAGTAAACTTGATGGAAAAAATATGTGGTACTGTTGGAATTGTAGCTATT

GAGTATCAAATTTGAGAAAAAGGTAAAAAAATATGTAAAATTTGGGTGGA

AGAAAAGAATTACATAAAATTGAGAAATGTATGTAATTGACAAAATAATG

TTTTCAAAACATAAAAACGTGATACCATTTAAATCCAAACCTTATATCAT

TTAACCATTTTTAGTAAAACTAATAGTAATGAATGGTCAATAATATAAGA

TTACATATTAAATAATTACTACTTTCAGAAAATTTCAATCAAATCTATAA

TATTCCTTTGAAAAAAAGAAAGACAAATAGGTAAACTTCGATCGTATCA

ATCAAAGAATATATTTATTTTTCATCGTAACGTTTAATTCTAAGTCCTAT

TAAAAAACGTTAAATTTGATTTTTCTTACCATTTTTTCTAAAAGGTGAG

TTGTGTGTTGTGTCAGGTCCAAAATAAAAGTTTGTCGTGAGGTCAAAATC

TACGGTTACAGTAATTTTAATAACCTGTGAATCTGTGTCTAATCGAAAAT

TACAAAACACCAGTTGTTGTTGCATGAGAGACTTGTGAGCTTAGATTAGT

GTGCGAGAGTCAGACAGAGAGAGATTTCGAATATCGA

SEQ ID NO: 4 FIE promoter with 3 bp change at −38 to −36 (GTG→CGA) 1.639 kb upstream of, but not including, the translation start site

GAGGAAGCGAGCAAGTACACAACAACCACAAAAGCTTTCAATACTTGTTT

ACTCCTAGGGTTTAAAACTAGAGGTTCTATAGATCTCTAAATTTTTTTGA

ACAAATGTGTTTTCCACACGTGATATTCTACAATACCACTCGAAAATTAT

CCATAATTGCTTTAAACTATTTTTTGTTTAAATTATATAATTTGTACCG

TTGTAAACTGATTATTTCAAATTATAATTAAAGCACTATAATTTCATATA

TTACATTCAACATATATTAAAATAAACTATAACCATGTATTTTTTTGTCT

TCCTTTCCTATAAACATTGATTGGACTCTATCGTAAATTTTGTCGTTATC

GCAAATTTTGTCGTTATCGATGAGTTTCTCAAAGTTTGGACCTTGATTAT

CTTGTTTGGAGATGTTCAAATCGTTATATCCAAATAGTGAACTTCTAATT

TTCTTTTTTGATAATGTGACTTATTTGGAAAAGTATTCCAAAGTATTCAA

ATAAACCCTTTAAAAATCCATTAAATACATTTTAAATAAGTAAAATGCTC

TCAACGAAGAGATATCATGGTAAATAACAACAGTGAGAGGATAAAATGTT

AAATCAATTTATTTACAACTTCAAATAGGCGGACATCAAACCTACTTAGC

ACACTTTCTATTTTCAAATTGGTTATGGTTTGTCTATTAGTTGTTGCATC

TAGTTTTTTAATTCTTATATCGGTGATCTTGATTTTGTTTGGTGTATCT

AAAATCTATTTTAGTTAAAGTGCAAGAAAATAAAATAAAAACTTAAGGTA

AGAGATGAAAGTAAGCTTTAAATAAAACAGAGCACTTCTATGGTCGATTA

TAGAGCCAAGTTCGTTCCTCCATTTTGGCTTAATGCAATATTACAAGTAA

ATCTTATAAAACTTTCCATAAGTATCGTATTACCCATGGATACTATGATA

TATAAACTCTCGGAGGTGTAGTCCAGAAGAAATGATCCATATTTGCATAC

AGTAAACTTGATGGAAAAAATATGTGGTACTGTTGGAATTGTAGCTATTG

AGTATCAAATTTGAGAAAAAGGTAAAAAAATATGTAAAATTTGGGTGGAA

-continued

GAAAAGAATTACATAAAATTGAGAAATGTATGTAATTGACAAAATAATGT

TTTCAAAACATAAAAACGTGATACCATTTAAATCCAAACCTTATATCATT

TAACCATTTTTAGTAAAACTAATAGTAATGAATGGTCAATAATATAAGAT

TACATATTAAATAATTACTACTTTCAGAAAATTTCAATCAAATCTATAAT

ATTCCTTTGAAAAAAAGAAAGACAAATAGGTAAACTTCGATCGTATCAA

TCAAAGAATATATTTATTTTTCATCGTAACGTTTAATTCTAAGTCCTATT

AAAAAACGTTAAATTTGATTTTTCTTACCATTTTTTTCTAAAAGGTGAGT

TGTGTGTTGTGTCAGGTCCAAAATAAAAGTTTGTCGTGAGGTCAAAATCT

ACGGTTACGAGTAATTTTAATAACCTGTGAATCTGTGTCTAATCGAAAAT

TACAAAACACCAGTTGTTGTTGCATGAGAGACTTGTGAGCTTAGATTAGT

CGACGAGAGTCAGACAGAGAGAGATTTCGAATATCGA

SEQ ID NO:5 FIE promoter 1.325 kb upstream of, but not including, the translation start. 3 bp change at −38 to −36 (GTG→CGA)

CATTGATTGGACTCTATCGTAAATTTTGTCGTTATCGCAAATTTTGTCGT

TATCGATGAGTTTCTCAAAGTTTGGACCTTGATTATCTTGTTTGGAGATG

TTCAAATCGTTATATCCAAATAGTGAACTTCTAATTTTCTTTTTTGATAA

TGTGACTTATTTGGAAAAGTATTCCAAAGTATTCAAATAAACCCTTTAAA

AATCCATTAAATACATTTTAAATAAGTAAAATGCTCTCAACGAAGAGATA

TCATGGTAAATAACAACAGTGAGAGGATAAAATGTTAAATCAATTTATTT

ACAACTTCAAATAGGCGGACATCAAACCTACTTAGCACACTTTCTATTTT

CAAATTGGTTATGGTTTGTCTATTAGTTGTTGCATCTATGTTTTTTAATT

CTTATATCGGTGATCTTGATTTTGTTTTGGTGTATCTAAAATCTATTTTA

GTTAAAGTGCAAGAAAATAAAATAAAAACTTAAGGTAAGAGATGAAAGTA

AGCTTTAAATAAAACAGAGCACTTCTATGGTCGATTATAGAGCCAAGTTC

GTTCCTCCATTTTGGCTTAATGCAATATTACAAGTAAATCTTATAAAACT

TTCCATAAGTATCGTATTACCCATGGATACTATGATATATAAACTCTCGG

AGGTGTAGTCCAGAAGAAATGATCCATATTTGCATACAGTAAACTTGATG

GAAAAAATATGTGGTACTGTTGGAATTGTAGCTATTGAGTATCAAATTTG

AGAAAAAGGTAAAAAAATATGTAAAATTTGGGTGGAAGAAAAGAATTACA

TAAAATTGAGAAATGTATGTAATTGACAAAATAATGTTTTCAAAACATAA

AAACGTGATACCATTTAAATCCAAACCTTATATCATTTAACCATTTTTAG

TAAAACTAATAGTAATGAATGGTCAATAATATAAGATTACATATTAAATA

ATTACTACTTTCAGAAAATTTCAATCAAATCTATAATATTCCTTTGAAAA

AAAGAAAGACAAATAGGTAAACTTCGATCGTATCAATCAAAGAATATAT

TTATTTTTCATCGTAACGTTTAATTCTAAGTCCTATTAAAAAACGTTAAA

TTTGATTTTTCTTACCATTTTTTTCTAAAAGGTGAGTTGTGTGTTGTGTC

AGGTCCAAAATAAAAGTTTGTCGTGAGGTCAAAATCTACGGTTACAGTAA

TTTTAATAACCTGTGAATCTGTGTCTAATCGAAAATTACAAAACACCAGT

-continued

TGTTGTTGCATGAGAGACTTGTGAGCTTAGATTAGTCGACGAGAGTCAGA

CAGAGAGAGAGATTTCGAATATCGA

SEQ ID NO:6 FIE promoter from −1274 to −128. Deletes 138 bp of 5' UTR from −128 to +9

ATCGATGAGTTTCTCAAAGTTTGGACCTTGATTATCTTGTTTGGAGATGT

TCAAATCGTTATATCCAAATAGTGAACTTCTAATTTTCTTTTTTGATAAT

GTGACTTATTTGGAAAAGTATTCCAAAGTATTCAAATAAACCCTTTAAAA

ATCCATTAAATACATTTTAAATAAGTAAAATGCTCTCAACGAAGAGATAT

CATGGTAAATAACAACAGTGAGAGGATAAAATGTTAAATCAATTTATTTA

CAACTTCAAATAGGCGGACATCAAACCTACTTAGCACACTTTCTATTTTC

AAATTGGTTATGGTTTGTCTATTAGTTGTTGCATCTATGTTTTTAATTC

TTATATCGGTGATCTTGATTTTGTTTTGGTGTATCTAAAATCTATTTTAG

TTAAAGTGCAAGAAAATAAAATAAAAACTTAAGGTAAGAGATGAAAGTAA

GCTTTAAATAAAACAGAGCACTTCTATGGTCGATTATAGAGCCAAGTTCG

TTCCTCCATTTTGGCTTAATGCAATATTACAAGTAAATCTTATAAAACTT

TCCATAAGTATCGTATTACCCATGGATACTATGATATATAAACTCTCGGA

GGTGTAGTCCAGAAGAAATGATCCATATTTGCATACAGTAAACTTGATGG

AAAAAATATGTGGTACTGTTGGAATTGTAGCTATTGAGTATCAAATTTGA

GAAAAAGGTAAAAAAATATGTAAAATTTGGGTGGAAGAAAAGAATTACAT

AAAATTGAGAAATGTATGTAATTGACAAAATAATGTTTTCAAAACATAAA

AACGTGATACCATTTAAATCCAAACCTTTATATCATTTAACCATTTTTAGT

AAAACTAATAGTAATGAATGGTCAATAATATAAGATTACATATTAAATAA

TTACTACTTTCAGAAAATTTCAATCAAATCTATAATATTCCTTTGAAAAA

AAAGAAAGACAAATAGGTAAACTTCGATCGTATCAATCAAAGAATATATT

TATTTTTCATCGTAACGTTTAATTCTAAGTCCTATTAAAAAACGTTAAAT

TTGATTTTTCTTACCATTTTTTTCTAAAAGGTGAGTTGTGTGTT

GTGTCAGGTC

SEQ ID NO:7 FIE promoter with −1274 upstream of start codon and +9.

ATCGATGAGTTTCTCAAAGTTTGGACCTTGATTATCTTGTTTGGAGATGT

TCAAATCGTTATATCCAAATAGTGAACTTCTAATTTTCTTTTTTGATAAT

GTGACTTATTTGGAAAAGTATTCCAAAGTATTCAAATAAACCCTTTAAAA

ATCCATTAAATACATTTTAAATAAGTAAAATGCTCTCAACGAAGAGATAT

CATGGTAAATAACAACAGTGAGAGGATAAAATGTTAAATCAATTTATTTA

CAACTTCAAATAGGCGGACATCAAACCTACTTAGCACACTTTCTATTTTC

AAATTGGTTATGGTTTGTCTATTAGTTGTTGCATCTATGTTTTTAATTC

TTATATCGGTGATCTTGATTTTGTTTTGGTGTATCTAAAATCTATTTTAG

TTAAAGTGCAAGAAAATAAAATAAAAACTTAAGGTAAGAGATGAAAGTAA

GCTTTAAATAAAACAGAGCACTTCTATGGTCGATTATAGAGCCAAGTTCG

-continued

TTCCTCCATTTTGGCTTAATGCAATATTACAAGTAAATCTTATAAAACTT

TCCATAAGTATCGTATTACCCATGGATACTATGATATATAAACTCTCGGA

GGTGTAGTCCAGAAGAAATGATCCATATTTGCATACAGTAAACTTGATGG

AAAAAATATGTGGTACTGTTGGAATTGTAGCTATTGAGTATCAAATTTGA

GAAAAAGGTAAAAAAATATGTAAAATTTGGGTGGAAGAAAAGAATTACAT

AAAATTGAGAAATGTATGTAATTGACAAAATAATGTTTTCAAAACATAAA

AACGTGATACCATTTAAATCCAAACCTTTATATCATTTAACCATTTTTAG

TAAAACTAATAGTAATGAATGGTCAATAATATAAGATTACATATTAAATA

ATTACTACTTTCAGAAAATTTCAATCAAATCTATAATATTCCTTTGAAAA

AAAAGAAAGACAAATAGGTAAACTTCGATCGTATCAATCAAAGAATATAT

TTATTTTTCATCGTAACGTTTAATTCTAAGTCCTATTAAAAAACGTTAAA

TTTGATTTTTCTTACCATTTTTTTCTAAAAGGTGAGTTGTGTGTTGTGTC

AGGTCCAAAATAAAAGTTTGTCGTGAGGTCAAAATCTACGGTTACAGTAA

TTTTAATAACCTGTGAATCTGTGTCTAATCGAAAATTACAAAACACCAGT

TGTTGTTGCATGAGAGACTTGTGAGCTTAGATTAGTGTGCGAGAGTCAGA

CAGAGAGAGAGATTTCGAATATCGAATGTCGAAG

SEQ ID NO:8

Amino Acid Sequence of FIE-15G-ESA1 Polypeptide

MSKITLGNESIVGSLTPSNKKSYKVTNRIQEGKKPLYAVVFNFLDARFFD

VFVTAGGNRITLYNCLGDGAISALQSYADE

DKEESFYTVSWACGVNGNPYVAAGGVKGIIRVIDVNSETIHKSLVGHDSV

NEIRTQPLKPQLVITASKDESVRLWNVET

GICILFAGAGGHRYEVLSVDFHPSDIYRFASCGMDTTIKIWSMKEFWTYV

EKSFTWTDDPSKFPTKFVQFPVFTASIHT

NYVDCNRWFGDFILSKSVDNEILLWEPQLEKNSPGEGASDVLLRYPVPMC

IDWFIKFSCDLHLSSVAIGNQEGKVYVWDL

KSCPPVLITKLSHNQSKSVIRQTAMSVDGSTILACCEDGTIWRWDVITKG

SPGGGGGGGGGGGGGGMRTHIEGHEELDA

SEQ ID NO:9

Nucleotide Sequence of FIE-15G-ESA1 cggagtactgtcctccgagcggagtactgtcctccgagcggagtactgtc
ctccgagcggagtactgtcctccgagcggagtactgtcctccgagcggag
actctagaacgattatttaggtgataagagtggacaatgatcgttgacac
gtggacggtccacaaattctagttttgcctataagtatcaaagctgaatg
tgtaagttggatccaacaccagttgttgttgcatgagagacttgtgagct
tagattagtgtgcgagagtcagacagagagagagatttcgaatatcgaat
gtcgaagataaccttagggaacgagtcaatagttgggtctttgactccat
cgaataagaaatcgtacaaagtgacgaataggattcaggaagggaagaaa
cctttgtatgctgttgttttcaacttccttgatcgtcgtttcttcgatgt
cttcgttaccgctggtggaaatcggattactctgtacaattgtctcggag
atggtgccatatcagcattgcaatcctatgctgatgaagataaggaagag
tcgttttacacggtaagttgggcgtgtggcgttaatgggaacccatatgt
tgcggctggaggagtaaaaggtataatccgagtcattgacgtcaacagtg
aaacgattcataagagtcttgtgggtcatggagattcagtgaacgaaatc
aggacacaacctttaaaacctcaacttgtgattactgctagcaaggatga
atctgttcgtttgtggaatgttgaaactgggatatgtattttgatatttg
ctggagctggaggtcatcgctatgaagttctaagtgtggattttcatccg
tctgatatttaccgctttgctagttgtggtatggacaccactattaaaat
atggtcaatgaaagattttggacgtacgtcgagaagtcattcacatggac
tgatgatccatcaaaattccccacaaaatttgtccaattcctgtattta
cagcttccattcatacaaattatgtagattgtaaccgttggtttggtgat
tttatcctctcaaagagtgtggacaacgagatcctgttgtgggaaccaca
actgaaagagaattctcctggcgagggagcttcagatgttctattaagat
acccggttccaatgtgtgatatttggtttatcaagttttcttgtgacctc
catttaagttctgttgcgataggtaatcaggaaggaaaggtttatgtctg
ggatttgaaaagttgccctcctgttttgattacaaagttatcacacaatc
aatcaaagtctgtaatcaggcaaacagccatgtctgtcgatggaagcacg
attcttgcttgctgcgaggacgggactatatggcgctgggacgtgattac
caagggatccccggaggtggaggtggaggtggaggtggaggtggaggtg
gaggtggaatgaggacacatatagagggtcatgaagagctggatgcagca agtttgcgtgaacatgaagagttcacgaaagtgaagaacatatcaacaat
tgagcttggaaaatatgagattgagacttggtacttctccccttttccgc
cagaatacaatgactgtgtgaagctctttttttgtgagttttgcctgaac
ttcatgaaacgcaaagagcagcttcaaaggcatatgagraagtgtgacct
gaagcacccacctggtgatgaaatttaccgaagtggtaccttgtcaatgt
ttgaggtagatggcaaaaagaacaaggtttatgcacagaatctctgctac
ctggcaaagttatttcttgaccacaaaactctttactacgatgttgattt
gtttctattctacgttctttgcgaatgtgatgaccgaggatgccacatgg
ttgggtacttttcaaaggagaagcattcggaagaagcatacaacttagct
tgcattctaaccctgccttcatatcaaagaaaaggctatggaaagttctt
aatagccttttcctatgaactgtcaaagaaagagggaaaagttgggacac
cggraaagacccttgtcggatctaggcttactaagctacagaggttattg
gactcgtgttctattagaaatcttgaaaaaacataactcgagggggggcc
cgctagagtcctgcttaatgagatatgcgagacgcctatgatcgcatga
tatttgctttcaattctgttgtgcacgttgtaaaaaacctgagcatgtgt
agctcagatccttaccgccggtttcggttcattctaatgaatatatcacc
cgttactatcgtatttttatgaataatattctccgttcaatttactgatt
gtaccctactacttatatgtacaatattaaaatgaaaacaatatattgtg
ctgaataggtttatagcgacatctatgatagagcgccacaataacaaaca
attgcgttttattattacaaatccaatttttaaaaaaagcggcagaaccgg
tcaaacctaaaagactgattacataaatcttattcaaatttcaaaggcc
ccaggggctagtatctacgacacaccgagcggcgaatctaataacgttca
ctgaagggaactccggttccccgccggcgcgcatgggtgagattccttga
agttgagtattggccgtccgctctaccgaaagttacgggcaccattcaac
ccggtccagcacggcggccgggtaaccgacttgctgccccgagaattatg
cagcatttttttggtgtatgtgggccccaaatgaagtgcaggtcaaacct
tgacagtgacgcaaatcgttgggcgggtccagggcgaattttgcgacaac
atgtcgaggctcagcag

SEQ ID NO:10

GAL4$_{UAS}$-VP16 transcription activator

```
aagctt ggatcc aaca atg aag ctc ctg tcc tcc atc gag cag gcc tgc gac atc tgc      40%
                    M   K   L   L   S   S   I   E   Q   A   C   D   I   C cgc ctc aag aag ctc aag tgc tcc aag gag aag ccg aag tgc gcc aag tct ctg aag aac  45%
 R   L   K   K   L   K   C   S   K   E   K   P   K   C   A   K   C   L   K   N aac tgg gag tgt cgc tac tct ccc aaa acc aag cgc tcc ccg ctg acc cgc gcc cac ctc  35%
 N   W   E   C   R   Y   S   P   K   T   K   R   S   P   L   T   R   A   H   L acc gaa gtg gag tcc cgc ctg gag cgc ctg gag cag ctc ttc ctc ctg atc ttc cct cga  37%
 T   E   V   E   S   R   L   E   R   L   E   Q   L   F   L   L   I   F   P   R
```

```
gag gac ctc gac atg atc ctg aaa atg gac tcc ctc cag gac atc aaa gcc ctg ctc acc    42%
 E   D   L   D   M   I   L   K   M   D   S   L   Q   D   I   K   A   L   L   T ggc ctc ttc gtc cag gac aac gtg aac aaa gac gcc gtc acc gac cgc ctg gcc tcc gtg    35%
 G   L   F   V   Q   D   N   V   N   K   D   A   V   T   D   R   L   A   S   V gag acc gac atg ccc ctc acc ctg cgc cag cac cgc atc agc gcg acc tcc tcc tcg gag    30%
 E   T   D   M   P   L   T   L   R   Q   H   R   I   S   A   T   S   S   S   E gag agc agc aac aag ggc cag cgc cag ttg acc gtc tcg acg gcc ccc ccg acc gac gtc    30%
 E   S   S   N   K   G   Q   R   Q   L   T   V   S   T   A   P   P   T   D   V agc ctg ggg gac gag ctc cac tta gac ggc gag gac gtg gcg atg gcg cat gcc gac gcg    30%
 S   L   G   D   E   L   H   L   D   G   E   D   V   A   M   A   H   A   D   A cta gac gat ttc gat ctg gac atg ttg ggg gac ggg gat tcc ccg ggg ccg gga ttt acc    40%
 L   D   D   F   D   L   D   M   L   G   D   G   D   S   P   G   P   G   F   T ccc cac gac tcc gcc ccc tac ggc gct ctg gat atg gcc gac ttc gag ttt gag cag atg    37%
 P   H   D   S   A   P   Y   G   A   L   D   M   A   D   F   E   F   E   Q   M ttt acc gat gcc ctt gga att gac gag tac ggt ggg tagatct
 F   T   D   A   L   G   I   D   E   Y   G   G   *
```

SEQ ID NO:11

>*Arabidopsis*: ESA1

MGSSANTETNGNAPPPSSNQKPPATNGVDGSHPPPPPLTPDQAIIESDPS

KKRKMGMLPLEVGTRVMCRWRDGKHHPPVKVIERRRIHNGGQNDYEYYVH

YTEFNRRLDEWTQLDQLDLDSVECAVDEKLEDKVTSLKMTRHQKRKIDET

HIEGHEELDAASLREHEEFTKVKNISTIELGKYEIETWYFSPFPPEYNDC

VKLFFCEFCLNFMKRKEQLQRHMXKCDLKHPPGDEIYRSGTLSMFEVDGK

KNKVYAQNLCYLAKLFLDHKTLYYDVDLFLFYVLCECDDRGCHMVGYFSK

EKHSEEAYNLACILTLPSYQRKGYGKFLIAFSYELSKKEGKVGTPXKTLV

GSRLTKLQRLLDSCSIRNLEKT

SEQ ID NO:12

>Protein sequence for HAC000003

MDSHSSHLNAANRSRSSQTPSPSHSASASVTSSLHKRKLAATTAANAAAS

EDHAPPSSSFPPSSFSADTRDGALTSNDELESISARGADTDSDPDESEDI

VVDDDEDEFAPEQDQDSSIRTFTAARLDSSSGVNGSSRNTKLKTESSTVK

LESSDGGKDGGSSVVGTGVSGTVGGSSISGLVPKDESVKVLAENFQTSGA

YIAREEALKREEQAGRLKFVCYSNDSIDEHMMCLIGLKNIFARQLPNMPK

EYIVRLLMDRKHKSVMVLRGNLVVGGITYRPYHSQKFGEIAFCAITADEQ

VKGYGTRLMNHLKQHARDVDGLTHFLTYADNNAVGYFVKQEIPQSFTSKS

SVSTLSYQGFTKEIYLEKDVWHGFIKDYDGGLLMECKIDPKLPYTDLSSM

IRQQRKAIDERIRELSNCQNVYPKIEFLKNEAGIPRKIIKVEEIRGLREA

GWTPDQWGHTRFKLFNGSADMVTNQKQLNALMRALLKTMQDHADAWPFKE

PVDSRDVPDYYDIIKDPIDLKVIAKRVESEQYYVTLDMFVADARRMFNNC

RTYNSPDTIYYKCATRLETHFHSKVQAGLQSGAKSQ

SEQ ID NO:13

>*Arabidopsis* HAT1

MSVKVKEEPVLVPNCDVENTELAVFNGNGESELENFGTCVDEITDRVNQL

EQKVVEVEHFYSTKDGAAQTNTSKSNSGGKKIAISQPNNSKGNSAGKEKS

KGKHVSSPDLMRQFATMFRQIAQHKWAWPFLEPVDVKGLGLHDYYKVIEK

PMDLGTIKKKMESSEYSNVREIYADVRLVFKNAMRYNEEKEDVYVMAESL

LEKFEEKWLLIMPKLVEEEKKQVDEEAEKHANKQLTMEAAQAEMARDLSN

ELYEIDLQLEKLRESVVQRCRKLSTQEKKGLSAALGRLSPEDLSKALKMV

SESENPSFPAGAPEVELDIDVQTDVTLWRLKVFVQEALKAANKSSGGTNAQ

NNNNTGTGEINKNNAKRRREISDAINKASIKRAKKA

SEQ ID NO:14
MEA
GI:3089625

```
  1 mekenheddg eglppelnqi keqiekerfl hikrkfelry ipsvathash hqsfdlnqpa
 61 aeddnggdnk sllsrmqnpl rhfsassdyn syedqgyvld edqdyaleed vplfldedvp
121 llpsvklpiv eklprsitwv ftkssqlmae sdsvigkrqi yylngealel sseedeedee
181 edeeeikkek cefsedvdrf iwtvgqdygl ddlvvrrala kylevdvsdi lerynelklk
241 ndgtageasd ltsktittaf qdfadrrhcr rcmifdchmh ekyepesrss edksslfede
301 drqpcsehcy lkvrsvtead hvmdndnsis nkivvsdpnn tmwtpvekdl ylkgieifgr
361 nscdvalnil rglktcleiy nymreqdqct msldlnkttq rhnqvtkkvs rkssrsvrkk
421 srlrkyaryp palkkttsge akfykhytpc tckskcgqqc pclthencce kycgcskdcn
481 nrfggcncai gqctnrqcpc faanrecdpd lcrscplscg dgtlgetpvq iqcknmqfll
541 qtnkkiligk sdvhgwgaft wdslkkneyl geytgelith deanergrie drigssylft
601 lndqleidar rkgnefkfln hsarpncyak lmivrgdqri glfaeraiee geelffdycy
661 gpehadwsrg reprktgask rskearpar
```

SEQ ID NO:15
Amino Acid Sequence of MEA-15G-ESA1 Polypeptide

MEKENHEDDGEGLPPELNQIKEQIEKERFLHIKRKFELRYIPSVATHASH
HQSFDLNQPAAEDDNGGDNKSLLSRMQNPLRHFSASSDYNSYEDQGYVLD
EDQDYALEEDVPLFLDEDVPLLPSVKLPIVEKLPRSITWVFTKSSQLMAE
SDSVIGKRQIYYLNGEALELSSEEDEEDEEEDEEEIKKEKCEFSEDVDRF
IWTVGQDYGLDDLVVRRALAKYLEVDVSDILERYNELKLKNDGTAGEASD
LTSKTITTAFQDFADRRHCRRCMIFDCHMHEKYEPESRSSEDKSSLFEDE
DRQPCSEHCYLKVRSVTEADHVMDNDNSISNKIVVSDPNNTMWTPVEKDL
YLKGIEIFGRNSCDVALNILRGLKTCLEIYNYMREQDQCTMSLDLNKTTQ
RHNQVTKKVSRKSSRSVRKKSRLRKYARYPPALKKTTSGEAKFYKHYTPC
TCKSKCGQQCPCLTHENCCEKYCGCSKDCNNRFGGCNCAIGQCTNRQCPC
FAANRECDPDLCRSCPLSCGDGTLGETPVQIQCKNMQFLLQTNKKILIGK
SDVHGWGAFTWDSLKKNEYLGEYTGELITHDEANERGRIEDRIGSSYLFT
LNDQLEIDARRKGNEFKFLNHSARPNCYAKLMIVRGDQRIGLFAERAIEE
GEELFFDYCYGPEHADWSRGREPRKTGASKRSKEARPARGSPGGGGGGGG
GGGGGGGMRTHIEGHEELDAASLREHEEFTKVKNISTIELGKYEIETWYF
SPFPPEYNDCVKLFFCEFCLNFMKRKEQLQRHMRKCDLKHPPGDEIYRSG
TLSMFEVKGKKNKVYAQNLCYLAKLFLDHKTLYYDVDLFLFYVLCECDDR
GCHMVGYFSKEKHSEEAYNLACILTLPSYQRKGYGKFLIAFSYELSKKEG
KVGTPXKTLVGSRLTKLQRLLDSCSIRNLEKT

SEQ ID NO:16
Nucleotide Sequence of MEA-15G-ESA1

```
atggagaaggaaaaccatgaggacgatggtgagggtttgccacccgaact
aaatcagataaaagagcaaatcgaaaggagagatttctgcatatcaaga
gaaaattcgagctgagatacattccaagtgtggctactcatgcttcacac
catcaatcgtttgacttaaaccagcccgctgcagaggatgataatggagg
agacaacaaatcacttttgtcgagaatgcaaaacccacttcgtcatttca
gtgcctcatctgattataattcttacgaagatcaaggttatgttcttgat
gaggatcaagattatgctcttgaagaagatgtaccattatttcttgatga
agatgtaccattattaccaagtgtcaagcttccaattgttgagaagctac
cacgatccattacatgggtcttcaccaaaagtagccagctgatggctgaa
agtgattctgtgattggtaagagacaaatctattatttgaatggtgaggc
actagaattgagcagtgaagaagatgaggaagatgaagaagaagatgagg
aagaaatcaagaaagaaaaatgcgaattttctgaagatgtagaccgattt
atatggacggttgggcaggactatggtttggatgatctggtcgtgcggcg
tgctctcgccaagtacctcgaagtggatgtttcggacatattggaaagat
acaatgaactcaagcttaagaatgatggaactgctggtgaggcttctgat
ttgacatccaagacaataactactgctttccaggattttgctgatagacg
tcattgccgtcgttgcatgatattcgattgtcatatgcatgagaagtatg
agcccgagtctagatccagcgaagacaaatctagtttgtttgaggatgaa
gatagacaaccatgcagtgagcattgttacctcaaggtcaggagtgtgac
agaagctgatcatgtgatggataatgataactctatatcaaacaagattg
tggtctcagatccaaacaacactatgtggacgcctgtagagaaggatctt
tacttgaaaggaattgagatatttgggagaaacagttgtgatgttgcatt
```

-continued

```
aaacatacttcgggggcttaagacgtgcctagagatttacaattacatgc
gcgaacaagatcaatgtactatgtcattagaccttaacaaaactacacaa
agacacaatcaggttaccaaaaaagtatctcgaaaaagtagtaggtcggt
ccgcaaaaaatcgagactccgaaaatatgctcgttatccgcctgctttaa
agaaaacaactagtggagaagctaagttttataagcactacacaccatgc
acttgcaagtcaaaatgtggacagcaatgccttgtttaactcacgaaaa
ttgctgcgagaaatattgcgggtgctcaaaggattgcaacaatcgctttg
gaggatgtaattgtgcaattggccaatgcacaaatcgacaatgtccttgt
tttgctgctaatcgtgaatgcgatccagatctttgtcggagttgtcctct
tagctgtggagatggcactcttggtgagacaccagtgcaaatccaatgca
agaacatgcaattcctccttcaaaccaataaaaagattctcattggaaag
tctgatgttcatggatggggtgcatttacatgggactctcttaaaaagaa
tgagtatctcggagaatatactggagaactgatcactcatgatgaagcta
atgagcgtgggagaatagaagatcggattggttcttcctacctcttacc
ttgaatgatcagctcgaaatcgatgctcgccgtaaaggaaacgagttcaa
atttctcaatcactcagcaagacctaactgctacgccaagttgatgattg
tgagaggagatcagaggattggtctatttgcggagagagcaatcgaagaa
ggtgaggagcttttcttcgactactgctatggaccagaacatgcggattg
gtcgcgtggtcgagaacctagaaagactggtgcttctaaaaggtctaagg
aagcccgtccagctcgtggatccccggaggtggaggtggaggtggaggt
ggaggtggaggtggaggtggaatgaggacacatatagagggtcatgaaga
gctggatgcagcaagtttgcgtgaacatgaagagttcacgaaagtgaaga
acatatcaacaattgagcttggaaaatatgagattgagacttggtacttc
tccccttttccgccagaatacaatgactgtgtgaagctcttttttttgtga
gttttgcctgaacttcatgaaacgcaaagagcagcttcaaaggcatatga
graagtgtgacctgaagcacccacctggtgatgaaatttaccgaagtggt
accttgtcaatgtttgaggtagatggcaaaaagaacaaggtttatgcaca
gaatctctgctacctggcaaagttatttcttgaccacaaaactctttact
```

-continued

```
acgatgttgatttgtttctattctacgttctttgcgaatgtgatgaccga
ggatgccacatggttgggtacttttcaaaggagaagcattcggaagaagc
atacaacttagcttgcattctaaccctgccttcatatcaaagaaaaggct
atggaaagttcttaatagccttttcctatgaactgtcaaagaaagaggga
aaagttgggacaccggraaagacccttgtcggatctaggcttactaagct
acagaggttattggactcgtgttctattagaaatcttgaaaaaacataa
```

SEQ ID NO:17

Nucleic acid sequence of Arabadopsis MEA gene
MEKENHEDDGEGLPPELNQIKEQIEKERFLHIKRKFELRYIPSVATHASH

HQSFDLNQPAAEDDNGGDNKSLLSRMQNPLRHFSASSDYNSYEDQGYVLD

EDQDYALEEDVPLFLDEDVPLLPSVKLPIVEKLPRSITWVFTKSSQLMAE

SDSVIGKRQIYYLNGEALELSSEEDEEDEEEEDEEEIKKEKCEFSEDVDR

FIWTVGQDYLDDLVVRRALAKYLEVDVSDILERYNELKLKNDGTAGEASD

LTSKTITTAFQDFADRRHCRRCMIFDCHMHEKYEPESRSSEDKSSLFEDE

DRQPCSEHCYLKVRSVTEADHVMDNDNSISNKIVVSDPNNTMWTPVEKDL

YLKGIEIFGRNSCDVALNILRGLKTCLEIYNYMREQDQCTMSLDLNKTTQ

RHNQVTKKVSRKSSRSVRKKSRLRKYARYPPALKKTTSGEAKFYKHYTPC

TCKSKCGQQCPCLTHENCCEKYCGCSKDCNNRFGGCNCAIGQCTNRQCPC

FAANRECDPDLCRSCPLSCGDGTLGETPVQIQCKNMQFLLQTNKKILIGK

SDVHGWGAFTWDSLKKNEYLGEYTGELITHDEANERGRIEDRIGSSYLFT

LNDQLEIDARRKGNEFKFLNHSARPNCYAKLMIVRGDQRIGLFAERAIEE

GEELFFDYCYGPEHADWSRGREPRKTGASKRSKEARPAR

---

What is claimed is:

1. An isolated nucleic acid molecule comprising SEQ ID NO:5.

2. The isolated nucleic acid molecule of claim 1, wherein the sequence comprises SEQ ID NO:4.

3. An isolated nucleic acid comprising a promoter operably linked to a heterologous polynucleotide, wherein the promoter comprises SEQ ID NO:5.

4. The nucleic acid of claim 3, wherein the promoter comprises SEQ ID NO:4.

5. A plant comprising an exogenous nucleic acid comprising a promoter operably linked to a heterologous polynucleotide, wherein the promoter comprises SEQ ID NO:5.

6. The plant of claim 5, wherein the promoter comprises SEQ ID NO:4.

7. A vector comprising a promoter operably linked to a heterologous polynucleotide, wherein the promoter comprises SEQ ID NO:5.

8. The vector of claim 7, wherein the promoter comprises SEQ ID NO:4.

* * * * *

SEQUENCE LISTING

<160> NUMBER OF SEQ ID NOS: 91

<210> SEQ ID NO 1
<211> LENGTH: 1563
<212> TYPE: DNA
<213> ORGANISM: Arabidopsis thaliana
<220> FEATURE:
<223> OTHER INFORMATION: FERTILIZATION INDEPENDENT ENDOSPERM (FIE)
      promoter sequence including the 5' and 3' UTRs
<220> FEATURE:
<221> NAME/KEY: CDS
<222> LOCATION: (199)..(1308)
<223> OTHER INFORMATION: FERTILIZATION INDEPENDENT ENDOSPERM (FIE)

-continued

```
<400> SEQUENCE: 1
aaaggtgagt tgtgtgttgt gtcaggtcca aaataaaagt ttgtcgtgag gtcaaaatct     60
acggttacag taattttaat aacctgtgaa tctgtgtcta atcgaaaatt acaaaacacc    120
agttgttgtt gcatgagaga cttgtgagct tagattagtg tgcgagagtc agacagagag    180
agagatttcg aatatcgaat gtcgaagata accttaggga acgagtcaat agttgggtct    240
ttgactccat cgaataagaa atcgtacaaa gtgacgaata ggattcagga agggaagaaa    300
cctttgtatg ctgttgtttt caacttcctt gatgctcgtt tcttcgatgt cttcgttacc    360
gctggtggaa atcggattac tctgtacaat tgtctcggag atggtgccat atcagcattg    420
caatcctatg ctgatgaaga taaggaagag tcgttttaca cggtaagttg ggcgtgtggc    480
gttaatggga acccatatgt tgcggctgga ggagtaaaag gtataatccg agtcattgac    540
gtcaacagtg aaacgattca taagagtctt gtgggtcatg agattcagt gaacgaaatc    600 aggacacaac ctttaaaacc tcaacttgtg attactgcta gcaaggatga atctgttcgt    660
ttgtggaatg ttgaaactgg gatatgtatt ttgatatttg ctggagctgg aggtcatcgc    720
tatgaagttc taagtgtgga ttttcatccg tctgatattt accgctttgc tagttgtggt    780
atggacacca ctattaaaat atggtcaatg aaagagtttt ggacgtacgt cgagaagtca    840
ttcacatgga ctgatgatcc atcaaaattc cccacaaaat ttgtccaatt ccctgtattt    900
acagcttcca ttcatacaaa ttatgtagat tgtaaccgtt ggtttggtga ttttatcctc    960
tcaaagagtg tggacaacga gatcctgttg tgggaaccac aactgaaaga gaattctcct   1020
ggcgagggag cttcagatgt tctattaaga tacccggttc caatgtgtga tatttggttt   1080
atcaagtttt cttgtgacct ccatttaagt tctgttgcga taggtaatca ggaaggaaag   1140
gtttatgtct gggatttgaa aagttgccct cctgttttga ttacaaagtt atcacacaat   1200
caatcaaagt ctgtaatcag gcaaacagcc atgtctgtcg atggaagcac gattcttgct   1260
tgctgcgagg acgggactat atggcgctgg gacgtgatta ccaagtagcg gtctgagtct   1320
tgtaggaatt gatgaattag gagtgcgaag aaatgagata tccattcttt tattgtaatt   1380
ctgatcatgt tgctactccc tgagaccttg agatgctctt tgtagcctgt ttaacgtcca   1440
cccttgtacc acagtgtata cccttttctgg agattttgtc ttattctctt agttcaatac   1500
acaaggctgt atcctggagc tttattgcag gaaccactct ctttcataag ctttctagta   1560
ttc                                                                 1563
```

<210> SEQ ID NO 2
<211> LENGTH: 369
<212> TYPE: PRT
<213> ORGANISM: Arabidopsis thaliana
<220> FEATURE:
<223> OTHER INFORMATION: FERTILIZATION INDEPENDENT ENDOSPERM (FIE)

<400> SEQUENCE: 2

```
Met Ser Lys Ile Thr Leu Gly Asn Glu Ser Ile Val Gly Ser Leu Thr
 1               5                  10                  15

Pro Ser Asn Lys Lys Ser Tyr Lys Val Thr Asn Arg Ile Gln Glu Gly
                20                  25                  30

Lys Lys Pro Leu Tyr Ala Val Val Phe Asn Phe Leu Asp Ala Arg Phe
            35                  40                  45

Phe Asp Val Phe Val Thr Ala Gly Gly Asn Arg Ile Thr Leu Tyr Asn
        50                  55                  60

Cys Leu Gly Asp Gly Ala Ile Ser Ala Leu Gln Ser Tyr Ala Asp Glu
```

-continued

```
                65                  70                  75                  80
Asp Lys Glu Glu Ser Phe Tyr Thr Val Ser Trp Ala Cys Gly Val Asn
                    85                  90                  95
Gly Asn Pro Tyr Val Ala Ala Gly Val Lys Gly Ile Ile Arg Val
                100                 105                 110
Ile Asp Val Asn Ser Glu Thr Ile His Lys Ser Leu Val Gly His Gly
            115                 120                 125
Asp Ser Val Asn Glu Ile Arg Thr Gln Pro Leu Lys Pro Gln Leu Val
        130                 135                 140
Ile Thr Ala Ser Lys Asp Glu Ser Val Arg Leu Trp Asn Val Glu Thr
145                 150                 155                 160
Gly Ile Cys Ile Leu Ile Phe Ala Gly Ala Gly Gly His Arg Tyr Glu
                165                 170                 175
Val Leu Ser Val Asp Phe His Pro Ser Asp Ile Tyr Arg Phe Ala Ser
                180                 185                 190
Cys Gly Met Asp Thr Thr Ile Lys Ile Trp Ser Met Lys Glu Phe Trp
                195                 200                 205
Thr Tyr Val Glu Lys Ser Phe Thr Trp Thr Asp Asp Pro Ser Lys Phe
210                 215                 220
Pro Thr Lys Phe Val Gln Phe Pro Val Phe Thr Ala Ser Ile His Thr
225                 230                 235                 240
Asn Tyr Val Asp Cys Asn Arg Trp Phe Gly Asp Phe Ile Leu Ser Lys
                245                 250                 255
Ser Val Asp Asn Glu Ile Leu Leu Trp Glu Pro Gln Leu Lys Glu Asn
                260                 265                 270
Ser Pro Gly Glu Gly Ala Ser Asp Val Leu Leu Arg Tyr Pro Val Pro
                275                 280                 285
Met Cys Asp Ile Trp Phe Ile Lys Phe Ser Cys Asp Leu His Leu Ser
                290                 295                 300
Ser Val Ala Ile Gly Asn Gln Glu Gly Lys Val Tyr Val Trp Asp Leu
305                 310                 315                 320
Lys Ser Cys Pro Pro Val Leu Ile Thr Lys Leu Ser His Asn Gln Ser
                325                 330                 335
Lys Ser Val Ile Arg Gln Thr Ala Met Ser Val Asp Gly Ser Thr Ile
                340                 345                 350
Leu Ala Cys Cys Glu Asp Gly Thr Ile Trp Arg Trp Asp Val Ile Thr
                355                 360                 365
Lys
```

<210> SEQ ID NO 3
<211> LENGTH: 1639
<212> TYPE: DNA
<213> ORGANISM: Arabidopsis thaliana
<220> FEATURE:
<223> OTHER INFORMATION: FERTILIZATION INDEPENDENT ENDOSPERM (FIE) promoter 1.1639 kb upstream of, but not including, the FIE translation start site

<400> SEQUENCE: 3

```
gaggaagcga gcaagtacac aacaaccaca aaagctttca atacttgttt actcctaggg    60
tttaaaacta gaggttctat agatctctaa attttttga acaaatgtgt tttccacacg   120
tgatattcta caataccact cgaaaattat ccataattgc tttaaactat ttttttgttt   180
aaattatata atttgtaccg ttgtaaactg attattcaa attataatta aagcactata   240
atttcatata ttacattcaa catatattaa aataaactat aaccatgtat ttttttgtct   300
```

```
tcctttccta taaacattga ttggactcta tcgtaaattt tgtcgttatc gcaaattttg      360
tcgttatcga tgagtttctc aaagtttgga ccttgattat cttgtttgga gatgttcaaa      420
tcgttatatc caaatagtga acttctaatt ttcttttttg ataatgtgac ttatttggaa      480
aagtattcca aagtattcaa ataaacccctt taaaaatcca ttaaatacat tttaaataag     540
taaaatgctc tcaacgaaga gatatcatgg taaataacaa cagtgagagg ataaaatgtt      600
aaatcaattt atttacaact tcaaataggc ggacatcaaa cctacttagc acactttcta      660
ttttcaaatt ggttatggtt tgtctattag ttgttgcatc tatgtttttt aattcttata      720
tcggtgatct tgattttgtt ttggtgtatc taaaatctat tttagttaaa gtgcaagaaa      780
ataaaataaa aacttaaggt aagagatgaa agtaagcttt aaataaaaca gagcacttct      840
atggtcgatt atagagccaa gttcgttcct ccattttggc ttaatgcaat attacaagta      900
aatcttataa aactttccat aagtatcgta ttacccatgg atactatgat atataaactc      960
tcggaggtgt agtccagaag aaatgatcca tatttgcata cagtaaactt gatggaaaaa     1020
atatgtggta ctgttggaat tgtagctatt gagtatcaaa tttgagaaaa aggtaaaaaa     1080
atatgtaaaa tttgggtgga agaaaagaat tacataaaat tgagaaatgt atgtaattga     1140
caaaataatg ttttcaaaac ataaaaacgt gataccattt aaatccaaac cttatatcat     1200 ttaaccatt tagtaaaac taatagtaat gaatggtcaa taatataaga ttacatatta      1260
aataattact actttcagaa aatttcaatc aaatctataa tattcctttg aaaaaaaaga     1320
aagacaaata ggtaaacttc gatcgtatca atcaaagaat atatttattt ttcatcgtaa     1380
cgtttaattc taagtcctat taaaaaacgt taaatttgat ttttcttacc atttttttct     1440
aaaaggtgag ttgtgtgttg tgtcaggtcc aaaataaaag tttgtcgtga ggtcaaaatc     1500
tacggttaca gtaattttaa taacctgtga atctgtgtct aatcgaaaat tacaaaacac     1560
cagttgttgt tgcatgagag acttgtgagc ttagattagt gtgcgagagt cagacagaga     1620
gagagatttc gaatatcga                                                  1639
```

<210> SEQ ID NO 4
<211> LENGTH: 1639
<212> TYPE: DNA
<213> ORGANISM: Artificial Sequence
<220> FEATURE:
<223> OTHER INFORMATION: Description of Artificial Sequence:modified
      FERTILIZATION INDEPENDENT ENDOSPERM (FIE) promoter
      with 3 bp change at -38 to -36 (GTG ->CGA) 1.639
      kb upstream of, but not including, the translation
      start site

<400> SEQUENCE: 4

```
gaggaagcga gcaagtacac aacaaccaca aaagctttca atacttgttt actcctaggg       60
tttaaaacta gaggttctat agatctctaa attttttga acaaatgtgt tttccacacg       120
tgatattcta caataccact cgaaaattat ccataattgc tttaaactat ttttttgttt      180
aaattatata atttgtaccg ttgtaaactg attatttcaa attataatta aagcactata      240
atttcatata ttacattcaa catatattaa aataaactat aaccatgtat ttttttgtct      300
tcctttccta taaacattga ttggactcta tcgtaaattt tgtcgttatc gcaaattttg      360
tcgttatcga tgagtttctc aaagtttgga ccttgattat cttgtttgga gatgttcaaa      420
tcgttatatc caaatagtga acttctaatt ttcttttttg ataatgtgac ttatttggaa      480
aagtattcca aagtattcaa ataaacccctt taaaaatcca ttaaatacat tttaaataag     540
```

-continued

```
taaaatgctc tcaacgaaga gatatcatgg taaataacaa cagtgagagg ataaaatgtt      600
aaatcaattt atttacaact tcaaataggc ggacatcaaa cctacttagc acactttcta      660
ttttcaaatt ggttatggtt tgtctattag ttgttgcatc tatgttttttt aattcttata      720 tcggtgatct tgattttgtt ttggtgtatc taaaatctat tttagttaaa gtgcaagaaa      780
ataaaataaa aacttaaggt aagagatgaa agtaagcttt aaataaaaca gagcacttct      840
atggtcgatt atagagccaa gttcgttcct ccatttttggc ttaatgcaat attacaagta      900
aatcttataa aactttccat aagtatcgta ttacccatgg atactatgat atataaactc      960
tcggaggtgt agtccagaag aaatgatcca tatttgcata cagtaaactt gatggaaaaa     1020
atatgtggta ctgttggaat tgtagctatt gagtatcaaa tttgagaaaa aggtaaaaaa     1080
atatgtaaaa tttgggtgga agaaaagaat tacataaaat tgagaaatgt atgtaattga     1140 caaataatg ttttcaaaac ataaaacgt gataccattt aaatccaaac cttatatcat       1200
ttaaccattt ttagtaaaac taatagtaat gaatggtcaa taatataaga ttacatatta     1260
aataattact actttcagaa aatttcaatc aaatctataa tattcctttg aaaaaaaga      1320 aagacaaata ggtaaacttc gatcgtatca atcaaagaat atatttattt ttcatcgtaa     1380
cgtttaattc taagtcctat taaaaaacgt taaatttgat ttttcttacc attttttttct   1440 aaaaggtgag ttgtgtgttg tgtcaggtcc aaaataaaag tttgtcgtga ggtcaaaatc    1500
tacggttaca gtaatttttaa taacctgtga atctgtgtct aatcgaaaat tacaaaacac    1560
cagttgttgt tgcatgagag acttgtgagc ttagattagt cgacgagagt cagacagaga     1620
gagagatttc gaatatcga                                                  1639
```

<210> SEQ ID NO 5
<211> LENGTH: 1325
<212> TYPE: DNA
<213> ORGANISM: Artificial Sequence
<220> FEATURE:
<223> OTHER INFORMATION: Description of Artificial Sequence:modified
      FERTILIZATION INDEPENDENT ENDOSPERM (FIE) promoter
      with 3 bp change at -38 to -36 (GTG ->CGA) 1.325
      kb upstream of, but not including, the translation
      start site

<400> SEQUENCE: 5

```
cattgattgg actctatcgt aaattttgtc gttatcgcaa attttgtcgt tatcgatgag       60
tttctcaaag tttggacctt gattatcttg tttggagatg ttcaaatcgt tatatccaaa      120
tagtgaactt ctaattttct ttttttgataa tgtgacttat ttggaaaagt attccaaagt     180
attcaaataa accctttaaa aatccattaa atacatttta aataagtaaa atgctctcaa      240
cgaagagata tcatggtaaa taacaacagt gagaggataa aatgttaaat caatttattt      300
acaacttcaa ataggcggac atcaaaccta cttagcacac tttctatttt caaattggtt      360
atggtttgtc tattagttgt tgcatctatg ttttttaatt cttatatcgg tgatcttgat      420
tttgttttgg tgtatctaaa atctatttta gttaaagtgc aagaaaataa aataaaaact     480
taaggtaaga gatgaaagta agctttaaat aaaacagagc acttctatgg tcgattatag     540
agccaagttc gttcctccat tttggcttaa tgcaatatta caagtaaatc ttataaaact      600
ttccataagt atcgtattac ccatggatac tatgatatat aaactctcgg aggtgtagtc      660
cagaagaaat gatccatatt tgcatacagt aaacttgatg gaaaaatat gtggtactgt       720 tggaattgta gctattgagt atcaaatttg agaaaaggt aaaaaaatat gtaaatttg       780 ggtggaagaa aagaattaca taaaattgag aaatgtatgt aattgacaaa ataatgtttt     840
```

```
caaaacataa aaacgtgata ccatttaaat ccaaaccttta tatcatttaa ccatttttag    900
taaaactaat agtaatgaat ggtcaataat ataagattac atattaaata attactactt    960
tcagaaaatt tcaatcaaat ctataatatt cctttgaaaa aaaagaaaga caaataggta   1020
aacttcgatc gtatcaatca agaatatat ttattttttca tcgtaacgtt taattctaag   1080
tcctattaaa aaacgttaaa tttgattttt cttaccattt ttttctaaaa ggtgagttgt   1140
gtgttgtgtc aggtccaaaa taaaagtttg tcgtgaggtc aaaatctacg gttacagtaa   1200
ttttaataac ctgtgaatct gtgtctaatc gaaaattaca aaacaccagt tgttgttgca   1260
tgagagactt gtgagcttag attagtcgac gagagtcaga cagagagaga gatttcgaat   1320
atcga                                                               1325
```

<210> SEQ ID NO 6
<211> LENGTH: 1104
<212> TYPE: DNA
<213> ORGANISM: Artificial Sequence
<220> FEATURE:
<223> OTHER INFORMATION: Description of Artificial Sequence:modified
      FERTILIZATION INDEPENDENT ENDOSPERM (FIE) promoter
      from -1274 to -128 with 138 bp deletion of 5' UTR
      from -128 to +9

<400> SEQUENCE: 6

```
atcgatgagt ttctcaaagt ttggaccttg attatcttgt ttggagatgt tcaaatcgtt     60
atatccaaat agtgaacttc taattttctt ttttgataat gtgacttatt tggaaaagta    120
ttccaaagta ttcaaataaa ccctttaaaa atccattaaa tacattttaa ataagtaaaa    180
tgctctcaac gaagagatat catggtaaat aacaacagtg agaggataaa atgttaaatc    240 aatttatttta caacttcaaa taggcggaca tcaaacctac ttagcacact ttctattttc    300
aaattggtta tggtttgtct attagttgtt gcatctatgt ttttttaattc ttatatcggt    360 gatcttgatt ttgttttggt gtatctaaaa tctattttag ttaaagtgca agaaaataaa    420
ataaaaactt aaggtaagag atgaaagtaa gctttaaata aaacagagca cttctatggt    480
cgattataga gccaagttcg ttcctccatt ttggcttaat gcaatattac aagtaaatct    540
tataaaactt tccataagta tcgtattacc catggatact atgatatata aactctcgga    600
ggtgtagtcc agaagaaatg atccatattt gcatacagta aacttgatgg aaaaaatatg    660
tggtactgtt ggaattgtag ctattgagta tcaaatttga gaaaaaggta aaaaaatatg    720
taaaatttgg gtggaagaaa agaattacat aaaattgaga aatgtatgta attgacaaaa    780
taatgttttc aaaacataaa aacgtgatac catttaaatc caaaccttat atcatttaac    840
catttttagt aaaactaata gtaatgaatg gtcaataata taagattaca tattaaataa    900
ttactacttt cagaaaattt caatcaaatc tataatattc ctttgaaaaa aagaaagac    960 aaataggtaa acttcgatcg tatcaatcaa agaatatatt tattttcat cgtaacgttt   1020 aattctaagt cctattaaaa aacgttaaat ttgattttc ttaccatttt tttctaaaag   1080
gtgagttgtg tgttgtgtca ggtc                                         1104
```

<210> SEQ ID NO 7
<211> LENGTH: 1283
<212> TYPE: DNA
<213> ORGANISM: Arabidopsis thaliana
<220> FEATURE:
<223> OTHER INFORMATION: FERTILIZATION INDEPENDENT ENDOSPERM (FIE)
      promoter with -1274 upstream of start codon and +9

```
<400> SEQUENCE: 7
atcgatgagt ttctcaaagt ttggaccttg attatcttgt ttggagatgt tcaaatcgtt      60
atatccaaat agtgaacttc taattttctt ttttgataat gtgacttatt tggaaaagta     120
ttccaaagta ttcaaataaa cccttttaaaa atccattaaa tacattttaa ataagtaaaa    180
tgctctcaac gaagagatat catggtaaat aacaacagtg agaggataaa atgttaaatc     240
aatttattta caacttcaaa taggcggaca tcaaacctac ttagcacact ttctattttc     300
aaattggtta tggtttgtct attagttgtt gcatctatgt tttttaattc ttatatcggt     360
gatcttgatt ttgttttggt gtatctaaaa tctattttag ttaaagtgca agaaaataaa     420
ataaaaactt aaggtaagag atgaaagtaa gctttaaata aaacagagca cttctatggt     480
cgattataga gccaagttcg ttcctccatt ttggcttaat gcaatattac aagtaaatct     540
tataaaactt tccataagta tcgtattacc catggatact atgatatata aactctcgga     600
ggtgtagtcc agaagaaatg atccatattt gcatacagta aacttgatgg aaaaaatatg     660
tggtactgtt ggaattgtag ctattgagta tcaaatttga gaaaaggta aaaaaatatg      720
taaaatttgg gtggaagaaa agaattacat aaaattgaga atgtatgta attgacaaaa      780
taatgttttc aaaacataaa aacgtgatac catttaaatc caaaccttat atcatttaac     840
cattttagt aaaactaata gtaatgaatg gtcaataata taagattaca tattaaataa      900
ttactacttt cagaaaattt caatcaaatc tataatattc ctttgaaaaa aagaaagac     960
aaataggtaa acttcgatcg tatcaatcaa agaatatatt tattttttcat cgtaacgttt    1020
aattctaagt cctattaaaa aacgttaaat ttgattttc ttaccattttt tttctaaaag    1080
gtgagttgtg tgttgtgtca ggtccaaaat aaaagtttgt cgtgaggtca aaatctacgg    1140
ttacagtaat tttaataacc tgtgaatctg tgtctaatcg aaaattacaa acaccagtt     1200
gttgttgcat gagagacttg tgagcttaga ttagtgtgcg agagtcagac agagagagag    1260
atttcgaata tcgaatgtcg aag                                            1283

<210> SEQ ID NO 8
<211> LENGTH: 400
<212> TYPE: PRT
<213> ORGANISM: Artificial Sequence
<220> FEATURE:
<223> OTHER INFORMATION: Description of Artificial Sequence:FIE-15G-ESA1

<400> SEQUENCE: 8

Met Ser Lys Ile Thr Leu Gly Asn Glu Ser Ile Val Gly Ser Leu Thr
  1               5                  10                  15

Pro Ser Asn Lys Lys Ser Tyr Lys Val Thr Asn Arg Ile Gln Glu Gly
                 20                  25                  30

Lys Lys Pro Leu Tyr Ala Val Val Phe Asn Phe Leu Asp Ala Arg Phe
             35                  40                  45

Phe Asp Val Phe Val Thr Ala Gly Gly Asn Arg Ile Thr Leu Tyr Asn
         50                  55                  60

Cys Leu Gly Asp Gly Ala Ile Ser Ala Leu Gln Ser Tyr Ala Asp Glu
 65                  70                  75                  80

Asp Lys Glu Glu Ser Phe Tyr Thr Val Ser Trp Ala Cys Gly Val Asn
                 85                  90                  95

Gly Asn Pro Tyr Val Ala Ala Gly Gly Val Lys Gly Ile Ile Arg Val
                100                 105                 110

Ile Asp Val Asn Ser Glu Thr Ile His Lys Ser Leu Val Gly His Gly
            115                 120                 125
```

-continued

```
Asp Ser Val Asn Glu Ile Arg Thr Gln Pro Leu Lys Pro Gln Leu Val
    130                 135                 140
Ile Thr Ala Ser Lys Asp Glu Ser Val Arg Leu Trp Asn Val Glu Thr
145                 150                 155                 160
Gly Ile Cys Ile Leu Ile Phe Ala Gly Ala Gly His Arg Tyr Glu
                165                 170                 175
Val Leu Ser Val Asp Phe His Pro Ser Asp Ile Tyr Arg Phe Ala Ser
            180                 185                 190
Cys Gly Met Asp Thr Thr Ile Lys Ile Trp Ser Met Lys Glu Phe Trp
        195                 200                 205
Thr Tyr Val Glu Lys Ser Phe Thr Trp Thr Asp Pro Ser Lys Phe
    210                 215                 220
Pro Thr Lys Phe Val Gln Phe Pro Val Phe Thr Ala Ser Ile His Thr
225                 230                 235                 240
Asn Tyr Val Asp Cys Asn Arg Trp Phe Gly Asp Phe Ile Leu Ser Lys
                245                 250                 255
Ser Val Asp Asn Glu Ile Leu Leu Trp Glu Pro Gln Leu Lys Glu Asn
            260                 265                 270
Ser Pro Gly Glu Gly Ala Ser Asp Val Leu Leu Arg Tyr Pro Val Pro
        275                 280                 285
Met Cys Asp Ile Trp Phe Ile Lys Phe Ser Cys Asp Leu His Leu Ser
    290                 295                 300
Ser Val Ala Ile Gly Asn Gln Glu Gly Lys Val Tyr Val Trp Asp Leu
305                 310                 315                 320
Lys Ser Cys Pro Pro Val Leu Ile Thr Lys Leu Ser His Asn Gln Ser
                325                 330                 335
Lys Ser Val Ile Arg Gln Thr Ala Met Ser Val Asp Gly Ser Thr Ile
            340                 345                 350
Leu Ala Cys Cys Glu Asp Gly Thr Ile Trp Arg Trp Asp Val Ile Thr
        355                 360                 365
Lys Gly Ser Pro Gly Gly Gly Gly Gly Gly Gly Gly Gly Gly Gly
    370                 375                 380
Gly Gly Gly Met Arg Thr His Ile Glu Gly His Glu Glu Leu Asp Ala
385                 390                 395                 400

<210> SEQ ID NO 9
<211> LENGTH: 2867
<212> TYPE: DNA
<213> ORGANISM: Artificial Sequence
<220> FEATURE:
<223> OTHER INFORMATION: Description of Artificial Sequence:FIE-15G-ESA1

<400> SEQUENCE: 9
cggagtactg tcctccgagc ggagtactgt cctccgagcg gagtactgtc ctccgagcgg      60
agtactgtcc tccgagcgga gtactgtcct ccgagcggag actctagaac gattatttag     120
gtgataagag tggacaatga tcgttgacac gtggacggtc cacaaattct agttttgcct     180
ataagtatca aagctgaatg tgtaagttgg atccaacacc agttgttgtt gcatgagaga     240
cttgtgagct tagattagtg tgcgagagtc agacagagag agagatttcg aatatcgaat     300
gtcgaagata accttaggga acgagtcaat agttgggtct ttgactccat cgaataagaa     360
atcgtacaaa gtgacgaata ggattcagga agggaagaaa cctttgtatg ctgttgtttt     420
caacttcctt gatgctcgtt tcttcgatgt cttcgttacc gctggtggaa atcggattac     480
tctgtacaat tgtctcggag atggtgccat atcagcattg caatcctatg ctgatgaaga     540
```

```
taaggaagag tcgttttaca cggtaagttg ggcgtgtggc gttaatggga acccatatgt    600
tgcggctgga ggagtaaaag gtataatccg agtcattgac gtcaacagtg aaacgattca    660
taagagtctt gtgggtcatg gagattcagt gaacgaaatc aggacacaac ctttaaaacc    720
tcaacttgtg attactgcta gcaaggatga atctgttcgt ttgtggaatg ttgaaactgg    780
gatatgtatt ttgatatttg ctggagctgg aggtcatcgc tatgaagttc taagtgtgga    840
ttttcatccg tctgatattt accgctttgc tagttgtggt atggacacca ctattaaaat    900
atggtcaatg aaagagtttt ggacgtacgt cgagaagtca ttcacatgga ctgatgatcc    960
atcaaaattc cccacaaaat tgtccaatt ccctgtattt acagcttcca ttcatacaaa   1020
ttatgtagat tgtaaccgtt ggtttggtga ttttatcctc tcaaagagtg tggacaacga   1080
gatcctgttg tgggaaccac aactgaaaga gaattctcct ggcgagggag cttcagatgt   1140
tctattaaga tacccggttc caatgtgtga tatttggttt atcaagtttt cttgtgacct   1200
ccatttaagt tctgttgcga taggtaatca ggaaggaaag gtttatgtct gggatttgaa   1260
aagttgccct cctgttttga ttacaaagtt atcacacaat caatcaaagt ctgtaatcag   1320
gcaaacagcc atgtctgtcg atggaagcac gattcttgct tgctgcgagg acgggactat   1380
atggcgctgg gacgtgatta ccaagggatc ccccggaggt ggaggtggag gtggaggtgg   1440
aggtggaggt ggaggtggaa tgaggacaca tatagagggt catgaagagc tggatgcagc   1500
aagtttgcgt gaacatgaag agttcacgaa agtgaagaac atatcaacaa ttgagcttgg   1560
aaaatatgag attgagactt ggtacttctc ccctttccg ccagaataca atgactgtgt   1620
gaagctcttt ttttgtgagt tttgcctgaa cttcatgaaa cgcaaagagc agcttcaaag   1680
gcatatgagr aagtgtgacc tgaagcaccc acctggtgat gaaatttacc gaagtggtac   1740
cttgtcaatg tttgaggtag atggcaaaaa gaacaaggtt tatgcacaga atctctgcta   1800
cctggcaaag ttatttcttg accacaaaac tctttactac gatgttgatt tgtttctatt   1860
ctacgttctt tgcgaatgtg atgaccgagg atgccacatg gttgggtact tttcaaagga   1920
gaagcattcg gaagaagcat acaacttagc ttgcattcta accctgcctt catatcaaag   1980
aaaaggctat ggaaagttct taatagcctt ttcctatgaa ctgtcaaaga agagggaaa    2040
agttgggaca ccggraaaga cccttgtcgg atctaggctt actaagctac agaggttatt   2100
ggactcgtgt tctattagaa atcttgaaaa acataactc gagggggggc ccgctagagt   2160
cctgctttaa tgagatatgc gagacgccta tgatcgcatg atatttgctt tcaattctgt   2220
tgtgcacgtt gtaaaaaacc tgagcatgtg tagctcagat ccttaccgcc ggtttcggtt   2280
cattctaatg aatatatcac ccgttactat cgtattttta tgaataatat tctccgttca   2340
atttactgat tgtaccctac tacttatatg tacaatatta aaatgaaaac aatatattgt   2400
gctgaatagg tttatagcga catctatgat agagcgccac aataacaaac aattgcgttt   2460
tattattaca aatccaattt taaaaaaagc ggcagaaccg gtcaaaccta aaagactgat   2520
tacataaatc ttattcaaat ttcaaaaggc cccagggct agtatctacg acacaccgag   2580
cggcgaacta ataacgttca ctgaagggaa ctccggttcc ccgccggcgc gcatgggtga   2640
gattccttga agttgagtat tggccgtccg ctctaccgaa agttacgggc accattcaac   2700
ccggtccagc acggcggccg ggtaaccgac ttgctgcccc gagaattatg cagcattttt   2760
ttggtgtatg tgggccccaa atgaagtgca ggtcaaacct tgacagtgac gcaaatcgtt   2820
gggcgggtcc agggcgaatt ttgcgacaac atgtcgaggc tcagcag            2867
```

<210> SEQ ID NO 10
<211> LENGTH: 701
<212> TYPE: DNA
<213> ORGANISM: Artificial Sequence
<220> FEATURE:
<223> OTHER INFORMATION: Description of Artificial Sequence:
      GAL4-UAS-VP16 transcription activator

<400> SEQUENCE: 10

```
aagcttggat ccaacaatga agctcctgtc ctccatcgag caggcctgcg acatctgccg      60
cctcaagaag ctcaagtgct ccaaggagaa gccgaagtgc gccaagtgtc tgaagaacaa     120
ctgggagtgt cgctactctc ccaaaaccaa gcgctccccg ctgacccgcg cccacctcac     180
cgaagtggag tcccgcctgg agcgcctgga gcagctcttc ctcctgatct ccctcgaga     240
ggacctcgac atgatcctga aaatggactc cctccaggac atcaaagccc tgctcaccgg     300
cctcttcgtc caggacaacg tgaacaaaga cgccgtcacc gaccgcctgg cctccgtgga     360
gaccgacatg cccctcaccc tgcgccagca ccgcatcagc gcgacctcct cctcggagga     420
gagcagcaac aagggccagc gccagttgac cgtctcgacg gcccccccga ccgacgtcag     480
cctgggggac gagctccact agacggcgga ggacgtggcg atggcgcatg ccgacgcgct     540
agacgatttc gatctggaca tgttggggga cggggattcc ccggggccgg gatttacccc     600
ccacgactcc gcccctacg cgcgctctgga tatggccgac ttcgagtttg agcagatgtt     660
taccgatgcc cttggaattg acgagtacgg tgggtagatc t                         701
```

<210> SEQ ID NO 11
<211> LENGTH: 371
<212> TYPE: PRT
<213> ORGANISM: Arabidopsis thaliana
<220> FEATURE:
<223> OTHER INFORMATION: ESA1 exemplary histone acetylase (HAT)
<220> FEATURE:
<221> NAME/KEY: MOD_RES
<222> LOCATION: (1)..(371)
<223> OTHER INFORMATION: Xaa = any amino acid

<400> SEQUENCE: 11

Met Gly Ser Ser Ala Asn Thr Glu Thr Asn Gly Asn Ala Pro Pro Pro
1               5                   10                  15

Ser Ser Asn Gln Lys Pro Pro Ala Thr Asn Gly Val Asp Gly Ser His
            20                  25                  30

Pro Pro Pro Pro Leu Thr Pro Asp Gln Ala Ile Ile Glu Ser Asp
        35                  40                  45

Pro Ser Lys Lys Arg Lys Met Gly Met Leu Pro Leu Glu Val Gly Thr
    50                  55                  60

Arg Val Met Cys Arg Trp Arg Asp Gly Lys His His Pro Val Lys Val
65                  70                  75                  80

Ile Glu Arg Arg Arg Ile His Asn Gly Gly Gln Asn Asp Tyr Glu Tyr
                85                  90                  95

Tyr Val His Tyr Thr Glu Phe Asn Arg Arg Leu Asp Glu Trp Thr Gln
            100                 105                 110

Leu Asp Gln Leu Asp Leu Asp Ser Val Glu Cys Ala Val Asp Glu Lys
        115                 120                 125

Leu Glu Asp Lys Val Thr Ser Leu Lys Met Thr Arg His Gln Lys Arg
    130                 135                 140

Lys Ile Asp Glu Thr His Ile Glu Gly His Glu Glu Leu Asp Ala Ala
145                 150                 155                 160

```
Ser Leu Arg Glu His Glu Phe Thr Lys Val Lys Asn Ile Ser Thr
                165                 170                 175

Ile Glu Leu Gly Lys Tyr Glu Ile Glu Thr Trp Tyr Phe Ser Pro Phe
            180                 185                 190

Pro Pro Glu Tyr Asn Asp Cys Val Lys Leu Phe Phe Cys Glu Phe Cys
        195                 200                 205

Leu Asn Phe Met Lys Arg Lys Glu Gln Leu Gln Arg His Met Xaa Lys
    210                 215                 220

Cys Asp Leu Lys His Pro Pro Gly Asp Glu Ile Tyr Arg Ser Gly Thr
225                 230                 235                 240

Leu Ser Met Phe Glu Val Asp Gly Lys Lys Asn Lys Val Tyr Ala Gln
                245                 250                 255

Asn Leu Cys Tyr Leu Ala Lys Leu Phe Leu Asp His Lys Thr Leu Tyr
            260                 265                 270

Tyr Asp Val Asp Leu Phe Leu Phe Tyr Val Leu Cys Glu Cys Asp Asp
        275                 280                 285

Arg Gly Cys His Met Val Gly Tyr Phe Ser Lys Glu Lys His Ser Glu
    290                 295                 300

Glu Ala Tyr Asn Leu Ala Cys Ile Leu Thr Leu Pro Ser Tyr Gln Arg
305                 310                 315                 320

Lys Gly Tyr Gly Lys Phe Leu Ile Ala Phe Ser Tyr Glu Leu Ser Lys
                325                 330                 335

Lys Glu Gly Lys Val Gly Thr Pro Xaa Lys Thr Leu Val Gly Ser Arg
            340                 345                 350

Leu Thr Lys Leu Gln Arg Leu Leu Asp Ser Cys Ser Ile Arg Asn Leu
        355                 360                 365

Glu Lys Thr
    370

<210> SEQ ID NO 12
<211> LENGTH: 586
<212> TYPE: PRT
<213> ORGANISM: Zea mays
<220> FEATURE:
<223> OTHER INFORMATION: HAC000003 exemplary histone acetylase (HAT)

<400> SEQUENCE: 12

Met Asp Ser His Ser Ser His Leu Asn Ala Ala Asn Arg Ser Arg Ser
  1               5                  10                  15

Ser Gln Thr Pro Ser Pro Ser His Ser Ala Ser Ala Ser Val Thr Ser
            20                  25                  30

Ser Leu His Lys Arg Lys Leu Ala Ala Thr Thr Ala Ala Asn Ala Ala
        35                  40                  45

Ala Ser Glu Asp His Ala Pro Pro Ser Ser Ser Phe Pro Pro Ser Ser
    50                  55                  60

Phe Ser Ala Asp Thr Arg Asp Gly Ala Leu Thr Ser Asn Asp Glu Leu
65                  70                  75                  80

Glu Ser Ile Ser Ala Arg Gly Ala Asp Thr Asp Ser Asp Pro Asp Glu
                85                  90                  95

Ser Glu Asp Ile Val Val Asp Asp Glu Asp Glu Phe Ala Pro Glu
            100                 105                 110

Gln Asp Gln Asp Ser Ser Ile Arg Thr Phe Thr Ala Ala Arg Leu Asp
        115                 120                 125

Ser Ser Ser Gly Val Asn Gly Ser Ser Arg Asn Thr Lys Leu Lys Thr
    130                 135                 140
```

-continued

```
Glu Ser Ser Thr Val Lys Leu Glu Ser Asp Gly Lys Asp Gly
145                 150                 155                 160

Gly Ser Ser Val Val Gly Thr Gly Val Ser Gly Thr Val Gly Gly Ser
            165                 170                 175

Ser Ile Ser Gly Leu Val Pro Lys Asp Glu Ser Val Lys Val Leu Ala
            180                 185                 190

Glu Asn Phe Gln Thr Ser Gly Ala Tyr Ile Ala Arg Glu Glu Ala Leu
        195                 200                 205

Lys Arg Glu Glu Gln Ala Gly Arg Leu Lys Phe Val Cys Tyr Ser Asn
    210                 215                 220

Asp Ser Ile Asp Glu His Met Met Cys Leu Ile Gly Leu Lys Asn Ile
225                 230                 235                 240

Phe Ala Arg Gln Leu Pro Asn Met Pro Lys Glu Tyr Ile Val Arg Leu
                245                 250                 255

Leu Met Asp Arg Lys His Lys Ser Val Met Val Leu Arg Gly Asn Leu
            260                 265                 270

Val Val Gly Gly Ile Thr Tyr Arg Pro Tyr His Ser Gln Lys Phe Gly
        275                 280                 285

Glu Ile Ala Phe Cys Ala Ile Thr Ala Asp Glu Gln Val Lys Gly Tyr
    290                 295                 300

Gly Thr Arg Leu Met Asn His Leu Lys Gln His Ala Arg Asp Val Asp
305                 310                 315                 320

Gly Leu Thr His Phe Leu Thr Tyr Ala Asp Asn Asn Ala Val Gly Tyr
                325                 330                 335

Phe Val Lys Gln Glu Ile Pro Gln Ser Phe Thr Ser Lys Ser Ser Val
            340                 345                 350

Ser Thr Leu Ser Tyr Gln Gly Phe Thr Lys Glu Ile Tyr Leu Glu Lys
        355                 360                 365

Asp Val Trp His Gly Phe Ile Lys Asp Tyr Asp Gly Gly Leu Leu Met
    370                 375                 380

Glu Cys Lys Ile Asp Pro Lys Leu Pro Tyr Thr Asp Leu Ser Ser Met
385                 390                 395                 400

Ile Arg Gln Gln Arg Lys Ala Ile Asp Glu Arg Ile Arg Glu Leu Ser
                405                 410                 415

Asn Cys Gln Asn Val Tyr Pro Lys Ile Glu Phe Leu Lys Asn Glu Ala
            420                 425                 430

Gly Ile Pro Arg Lys Ile Ile Lys Val Glu Glu Ile Arg Gly Leu Arg
        435                 440                 445

Glu Ala Gly Trp Thr Pro Asp Gln Trp Gly His Thr Arg Phe Lys Leu
    450                 455                 460

Phe Asn Gly Ser Ala Asp Met Val Thr Asn Gln Lys Gln Leu Asn Ala
465                 470                 475                 480

Leu Met Arg Ala Leu Leu Lys Thr Met Gln Asp His Ala Asp Ala Trp
                485                 490                 495

Pro Phe Lys Glu Pro Val Asp Ser Arg Asp Val Pro Asp Tyr Tyr Asp
            500                 505                 510

Ile Ile Lys Asp Pro Ile Asp Leu Lys Val Ile Ala Lys Arg Val Glu
        515                 520                 525

Ser Glu Gln Tyr Tyr Val Thr Leu Asp Met Phe Val Ala Asp Ala Arg
    530                 535                 540

Arg Met Phe Asn Asn Cys Arg Thr Tyr Asn Ser Pro Asp Thr Ile Tyr
545                 550                 555                 560

Tyr Lys Cys Ala Thr Arg Leu Glu Thr His Phe His Ser Lys Val Gln
```

```
                         565                 570                 575
Ala Gly Leu Gln Ser Gly Ala Lys Ser Gln
            580                 585

<210> SEQ ID NO 13
<211> LENGTH: 386
<212> TYPE: PRT
<213> ORGANISM: Arabidopsis thaliana
<220> FEATURE:
<223> OTHER INFORMATION: HAT1 exemplary histone acetylase (HAT)

<400> SEQUENCE: 13

Met Ser Val His Val Lys Glu Glu Pro Val Leu Val Pro Asn Cys Asp
 1               5                  10                  15

Val Glu Asn Thr Glu Leu Ala Val Phe Asn Gly Asn Gly Glu Ser Glu
            20                  25                  30

Leu Glu Asn Phe Gly Thr Cys Val Asp Glu Ile Thr Asp Arg Val Asn
        35                  40                  45

Gln Leu Glu Gln Lys Val Val Glu Val Glu His Phe Tyr Ser Thr Lys
    50                  55                  60

Asp Gly Ala Ala Gln Thr Asn Thr Ser Lys Ser Asn Ser Gly Gly Lys
65                  70                  75                  80

Lys Ile Ala Ile Ser Gln Pro Asn Asn Ser Lys Gly Asn Ser Ala Gly
                85                  90                  95

Lys Glu Lys Ser Lys Gly Lys His Val Ser Ser Pro Asp Leu Met Arg
            100                 105                 110

Gln Phe Ala Thr Met Phe Arg Gln Ile Ala Gln His Lys Trp Ala Trp
        115                 120                 125

Pro Phe Leu Glu Pro Val Asp Val Lys Gly Leu Gly Leu His Asp Tyr
    130                 135                 140

Tyr Lys Val Ile Glu Lys Pro Met Asp Leu Gly Thr Ile Lys Lys Lys
145                 150                 155                 160

Met Glu Ser Ser Glu Tyr Ser Asn Val Arg Glu Ile Tyr Ala Asp Val
                165                 170                 175

Arg Leu Val Phe Lys Asn Ala Met Arg Tyr Asn Glu Glu Lys Glu Asp
            180                 185                 190

Val Tyr Val Met Ala Glu Ser Leu Leu Glu Lys Phe Glu Glu Lys Trp
        195                 200                 205

Leu Leu Ile Met Pro Lys Leu Val Glu Glu Lys Lys Gln Val Asp
    210                 215                 220

Glu Glu Ala Glu Lys His Ala Asn Lys Gln Leu Thr Met Glu Ala Ala
225                 230                 235                 240

Gln Ala Glu Met Ala Arg Asp Leu Ser Asn Glu Leu Tyr Glu Ile Asp
                245                 250                 255

Leu Gln Leu Glu Lys Leu Arg Glu Ser Val Val Gln Arg Cys Arg Lys
            260                 265                 270

Leu Ser Thr Gln Glu Lys Lys Gly Leu Ser Ala Ala Leu Gly Arg Leu
        275                 280                 285

Ser Pro Glu Asp Leu Ser Lys Ala Leu Lys Met Val Ser Glu Ser Asn
    290                 295                 300

Pro Ser Phe Pro Ala Gly Ala Pro Glu Val Glu Leu Asp Ile Asp Val
305                 310                 315                 320

Gln Thr Asp Val Thr Leu Trp Arg Leu Lys Val Phe Val Gln Glu Ala
                325                 330                 335

Leu Lys Ala Ala Asn Lys Ser Ser Gly Gly Thr Asn Ala Gln Asn Asn
```

```
                    340                 345                 350
Asn Asn Thr Gly Thr Gly Glu Ile Asn Lys Asn Ala Lys Arg Arg
                355                 360                 365
Arg Glu Ile Ser Asp Ala Ile Asn Lys Ala Ser Ile Lys Arg Ala Lys
            370                 375                 380
Lys Ala
385

<210> SEQ ID NO 14
<211> LENGTH: 689
<212> TYPE: PRT
<213> ORGANISM: Arabidopsis thaliana
<220> FEATURE:
<223> OTHER INFORMATION: MEDEA (MEA)

<400> SEQUENCE: 14

Met Glu Lys Glu Asn His Glu Asp Asp Gly Glu Gly Leu Pro Pro Glu
  1               5                  10                  15
Leu Asn Gln Ile Lys Glu Gln Ile Glu Lys Glu Arg Phe Leu His Ile
                 20                  25                  30
Lys Arg Lys Phe Glu Leu Arg Tyr Ile Pro Ser Val Ala Thr His Ala
             35                  40                  45
Ser His His Gln Ser Phe Asp Leu Asn Gln Pro Ala Ala Glu Asp Asp
         50                  55                  60
Asn Gly Gly Asp Asn Lys Ser Leu Leu Ser Arg Met Gln Asn Pro Leu
 65                  70                  75                  80
Arg His Phe Ser Ala Ser Ser Asp Tyr Asn Ser Tyr Glu Asp Gln Gly
                 85                  90                  95
Tyr Val Leu Asp Glu Asp Gln Asp Tyr Ala Leu Glu Glu Asp Val Pro
            100                 105                 110
Leu Phe Leu Asp Glu Asp Val Pro Leu Leu Pro Ser Val Lys Leu Pro
        115                 120                 125
Ile Val Glu Lys Leu Pro Arg Ser Ile Thr Trp Val Phe Thr Lys Ser
    130                 135                 140
Ser Gln Leu Met Ala Glu Ser Asp Ser Val Ile Gly Lys Arg Gln Ile
145                 150                 155                 160
Tyr Tyr Leu Asn Gly Glu Ala Leu Glu Leu Ser Ser Glu Glu Asp Glu
                165                 170                 175
Glu Asp Glu Glu Glu Asp Glu Glu Ile Lys Lys Glu Lys Cys Glu
            180                 185                 190
Phe Ser Glu Asp Val Asp Arg Phe Ile Trp Thr Val Gly Gln Asp Tyr
        195                 200                 205
Gly Leu Asp Asp Leu Val Val Arg Arg Ala Leu Ala Lys Tyr Leu Glu
    210                 215                 220
Val Asp Val Ser Asp Ile Leu Glu Arg Tyr Asn Glu Leu Lys Leu Lys
225                 230                 235                 240
Asn Asp Gly Thr Ala Gly Glu Ala Ser Asp Leu Thr Ser Lys Thr Ile
                245                 250                 255
Thr Thr Ala Phe Gln Asp Phe Ala Asp Arg Arg His Cys Arg Arg Cys
            260                 265                 270
Met Ile Phe Asp Cys His Met His Glu Lys Tyr Glu Pro Glu Ser Arg
        275                 280                 285
Ser Ser Glu Asp Lys Ser Ser Leu Phe Glu Asp Glu Arg Gln Pro
    290                 295                 300
Cys Ser Glu His Cys Tyr Leu Lys Val Arg Ser Val Thr Glu Ala Asp
```

```
            305                 310                 315                 320

His Val Met Asp Asn Asp Asn Ser Ile Ser Asn Lys Ile Val Val Ser
                325                 330                 335

Asp Pro Asn Asn Thr Met Trp Thr Pro Val Glu Lys Asp Leu Tyr Leu
            340                 345                 350

Lys Gly Ile Glu Ile Phe Gly Arg Asn Ser Cys Asp Val Ala Leu Asn
            355                 360                 365

Ile Leu Arg Gly Leu Lys Thr Cys Leu Glu Ile Tyr Asn Tyr Met Arg
        370                 375                 380

Glu Gln Asp Gln Cys Thr Met Ser Leu Asp Leu Asn Lys Thr Thr Gln
385                 390                 395                 400

Arg His Asn Gln Val Thr Lys Val Ser Arg Lys Ser Ser Arg Ser
                405                 410                 415

Val Arg Lys Lys Ser Arg Leu Arg Lys Tyr Ala Arg Tyr Pro Pro Ala
            420                 425                 430

Leu Lys Lys Thr Thr Ser Gly Glu Ala Lys Phe Tyr Lys His Tyr Thr
            435                 440                 445

Pro Cys Thr Cys Lys Ser Lys Cys Gly Gln Gln Cys Pro Cys Leu Thr
        450                 455                 460

His Glu Asn Cys Cys Glu Lys Tyr Cys Gly Cys Ser Lys Asp Cys Asn
465                 470                 475                 480

Asn Arg Phe Gly Gly Cys Asn Cys Ala Ile Gly Gln Cys Thr Asn Arg
                485                 490                 495

Gln Cys Pro Cys Phe Ala Ala Asn Arg Glu Cys Asp Pro Asp Leu Cys
            500                 505                 510

Arg Ser Cys Pro Leu Ser Cys Gly Asp Gly Thr Leu Gly Glu Thr Pro
            515                 520                 525

Val Gln Ile Gln Cys Lys Asn Met Gln Phe Leu Leu Gln Thr Asn Lys
        530                 535                 540

Lys Ile Leu Ile Gly Lys Ser Asp Val His Gly Trp Gly Ala Phe Thr
545                 550                 555                 560

Trp Asp Ser Leu Lys Lys Asn Glu Tyr Leu Gly Glu Tyr Thr Gly Glu
                565                 570                 575

Leu Ile Thr His Asp Glu Ala Asn Glu Arg Gly Arg Ile Glu Asp Arg
            580                 585                 590

Ile Gly Ser Ser Tyr Leu Phe Thr Leu Asn Asp Gln Leu Glu Ile Asp
        595                 600                 605

Ala Arg Arg Lys Gly Asn Glu Phe Lys Phe Leu Asn His Ser Ala Arg
        610                 615                 620

Pro Asn Cys Tyr Ala Lys Leu Met Ile Val Arg Gly Asp Gln Arg Ile
625                 630                 635                 640

Gly Leu Phe Ala Glu Arg Ala Ile Glu Glu Gly Glu Glu Leu Phe Phe
                645                 650                 655

Asp Tyr Cys Tyr Gly Pro Glu His Ala Asp Trp Ser Arg Gly Arg Glu
            660                 665                 670

Pro Arg Lys Thr Gly Ala Ser Lys Arg Ser Lys Glu Ala Arg Pro Ala
            675                 680                 685

Arg

<210> SEQ ID NO 15
<211> LENGTH: 932
<212> TYPE: PRT
<213> ORGANISM: Artificial Sequence
<220> FEATURE:
```

-continued

```
<223> OTHER INFORMATION: Description of Artificial Sequence:MEA-15G-ESA1
      chimeric polypeptide encoded by transgene plasmid
      pCRS304-5UAS MEA-15G-ESA1
<220> FEATURE:
<221> NAME/KEY: MOD_RES
<222> LOCATION: (906)
<223> OTHER INFORMATION: Xaa = Gly or Glu

<400> SEQUENCE: 15

Met Glu Lys Glu Asn His Glu Asp Asp Gly Glu Gly Leu Pro Pro Glu
 1               5                  10                  15

Leu Asn Gln Ile Lys Glu Gln Ile Glu Lys Glu Arg Phe Leu His Ile
             20                  25                  30

Lys Arg Lys Phe Glu Leu Arg Tyr Ile Pro Ser Val Ala Thr His Ala
         35                  40                  45

Ser His His Gln Ser Phe Asp Leu Asn Gln Pro Ala Ala Glu Asp Asp
     50                  55                  60

Asn Gly Gly Asp Asn Lys Ser Leu Leu Ser Arg Met Gln Asn Pro Leu
 65                  70                  75                  80

Arg His Phe Ser Ala Ser Ser Asp Tyr Asn Ser Tyr Glu Asp Gln Gly
                 85                  90                  95

Tyr Val Leu Asp Glu Asp Gln Asp Tyr Ala Leu Glu Glu Asp Val Pro
            100                 105                 110

Leu Phe Leu Asp Glu Asp Val Pro Leu Leu Pro Ser Val Lys Leu Pro
        115                 120                 125

Ile Val Glu Lys Leu Pro Arg Ser Ile Thr Trp Val Phe Thr Lys Ser
130                 135                 140

Ser Gln Leu Met Ala Glu Ser Asp Ser Val Ile Gly Lys Arg Gln Ile
145                 150                 155                 160

Tyr Tyr Leu Asn Gly Glu Ala Leu Glu Leu Ser Ser Glu Glu Asp Glu
                165                 170                 175

Glu Asp Glu Glu Glu Asp Glu Glu Ile Lys Lys Glu Lys Cys Glu
            180                 185                 190

Phe Ser Glu Asp Val Asp Arg Phe Ile Trp Thr Val Gly Gln Asp Tyr
        195                 200                 205

Gly Leu Asp Asp Leu Val Val Arg Ala Leu Ala Lys Tyr Leu Glu
    210                 215                 220

Val Asp Val Ser Asp Ile Leu Glu Arg Tyr Asn Glu Leu Lys Leu Lys
225                 230                 235                 240

Asn Asp Gly Thr Ala Gly Glu Ala Ser Asp Leu Thr Ser Lys Thr Ile
                245                 250                 255

Thr Thr Ala Phe Gln Asp Phe Ala Asp Arg Arg His Cys Arg Arg Cys
            260                 265                 270

Met Ile Phe Asp Cys His Met His Glu Lys Tyr Glu Pro Glu Ser Arg
        275                 280                 285

Ser Ser Glu Asp Lys Ser Ser Leu Phe Glu Asp Glu Arg Gln Pro
    290                 295                 300

Cys Ser Glu His Cys Tyr Leu Lys Val Arg Ser Val Thr Glu Ala Asp
305                 310                 315                 320

His Val Met Asp Asn Asp Asn Ser Ile Ser Asn Lys Ile Val Val Ser
                325                 330                 335

Asp Pro Asn Asn Thr Met Trp Thr Pro Val Glu Lys Asp Leu Tyr Leu
            340                 345                 350

Lys Gly Ile Glu Ile Phe Gly Arg Asn Ser Cys Asp Val Ala Leu Asn
        355                 360                 365
```

```
Ile Leu Arg Gly Leu Lys Thr Cys Leu Glu Ile Tyr Asn Tyr Met Arg
370                 375                 380

Glu Gln Asp Gln Cys Thr Met Ser Leu Asp Leu Asn Lys Thr Thr Gln
385                 390                 395                 400

Arg His Asn Gln Val Thr Lys Lys Val Ser Arg Lys Ser Ser Arg Ser
            405                 410                 415

Val Arg Lys Lys Ser Arg Leu Arg Lys Tyr Ala Arg Tyr Pro Pro Ala
        420                 425                 430

Leu Lys Lys Thr Thr Ser Gly Glu Ala Lys Phe Tyr Lys His Tyr Thr
        435                 440                 445

Pro Cys Thr Cys Lys Ser Lys Cys Gly Gln Gln Cys Pro Cys Leu Thr
        450                 455                 460

His Glu Asn Cys Cys Glu Lys Tyr Cys Gly Cys Ser Lys Asp Cys Asn
465                 470                 475                 480

Asn Arg Phe Gly Gly Cys Asn Cys Ala Ile Gly Gln Cys Thr Asn Arg
            485                 490                 495

Gln Cys Pro Cys Phe Ala Ala Asn Arg Glu Cys Asp Pro Asp Leu Cys
            500                 505                 510

Arg Ser Cys Pro Leu Ser Cys Gly Asp Gly Thr Leu Gly Glu Thr Pro
        515                 520                 525

Val Gln Ile Gln Cys Lys Asn Met Gln Phe Leu Leu Gln Thr Asn Lys
        530                 535                 540

Lys Ile Leu Ile Gly Lys Ser Asp Val His Gly Trp Gly Ala Phe Thr
545                 550                 555                 560

Trp Asp Ser Leu Lys Lys Asn Glu Tyr Leu Gly Glu Tyr Thr Gly Glu
            565                 570                 575

Leu Ile Thr His Asp Glu Ala Asn Glu Arg Gly Arg Ile Glu Asp Arg
            580                 585                 590

Ile Gly Ser Ser Tyr Leu Phe Thr Leu Asn Asp Gln Leu Glu Ile Asp
        595                 600                 605

Ala Arg Arg Lys Gly Asn Glu Phe Lys Phe Leu Asn His Ser Ala Arg
        610                 615                 620

Pro Asn Cys Tyr Ala Lys Leu Met Ile Val Arg Gly Asp Gln Arg Ile
625                 630                 635                 640

Gly Leu Phe Ala Glu Arg Ala Ile Glu Glu Gly Glu Glu Leu Phe Phe
            645                 650                 655

Asp Tyr Cys Tyr Gly Pro Glu His Ala Asp Trp Ser Arg Gly Arg Glu
            660                 665                 670

Pro Arg Lys Thr Gly Ala Ser Lys Arg Ser Lys Glu Ala Arg Pro Ala
        675                 680                 685

Arg Gly Ser Pro Gly Gly Gly Gly Gly Gly Gly Gly Gly Gly Gly Gly
        690                 695                 700

Gly Gly Gly Met Arg Thr His Ile Glu Gly His Glu Glu Leu Asp Ala
705                 710                 715                 720

Ala Ser Leu Arg Glu His Glu Glu Phe Thr Lys Val Lys Asn Ile Ser
            725                 730                 735

Thr Ile Glu Leu Gly Lys Tyr Glu Ile Glu Thr Trp Tyr Phe Ser Pro
        740                 745                 750

Phe Pro Pro Glu Tyr Asn Asp Cys Val Lys Leu Phe Phe Cys Glu Phe
        755                 760                 765

Cys Leu Asn Phe Met Lys Arg Lys Glu Gln Leu Gln Arg His Met Arg
        770                 775                 780

Lys Cys Asp Leu Lys His Pro Pro Gly Asp Glu Ile Tyr Arg Ser Gly
```

```
                785                 790                 795                 800
Thr Leu Ser Met Phe Glu Val Asp Gly Lys Lys Asn Lys Val Tyr Ala
                    805                 810                 815
Gln Asn Leu Cys Tyr Leu Ala Lys Leu Phe Leu Asp His Lys Thr Leu
                820                 825                 830
Tyr Tyr Asp Val Asp Leu Phe Leu Phe Tyr Val Leu Cys Glu Cys Asp
            835                 840                 845
Asp Arg Gly Cys His Met Val Gly Tyr Phe Ser Lys Glu Lys His Ser
        850                 855                 860
Glu Glu Ala Tyr Asn Leu Ala Cys Ile Leu Thr Leu Pro Ser Tyr Gln
865                 870                 875                 880
Arg Lys Gly Tyr Gly Lys Phe Leu Ile Ala Phe Ser Tyr Glu Leu Ser
                885                 890                 895
Lys Lys Glu Gly Lys Val Gly Thr Pro Xaa Lys Thr Leu Val Gly Ser
                900                 905                 910
Arg Leu Thr Lys Leu Gln Arg Leu Leu Asp Ser Cys Ser Ile Arg Asn
            915                 920                 925
Leu Glu Lys Thr
    930

<210> SEQ ID NO 16
<211> LENGTH: 2799
<212> TYPE: DNA
<213> ORGANISM: Artificial Sequence
<220> FEATURE:
<223> OTHER INFORMATION: Description of Artificial Sequence:MEA-15G-ESA1
      chimeric HAT nucleic acid construct encoded by
      transgene plasmid pCRS304-5UAS MEA-15G-ESA1

<400> SEQUENCE: 16
atggagaagg aaaaccatga ggacgatggt gagggtttgc cacccgaact aaatcagata      60
aaagagcaaa tcgaaaagga gagatttctg catatcaaga gaaaattcga gctgagatac     120
attccaagtg tggctactca tgcttcacac catcaatcgt ttgacttaaa ccagcccgct     180
gcagaggatg ataatggagg agacaacaaa tcacttttgt cgagaatgca aaacccactt     240
cgtcatttca gtgcctcatc tgattataat tcttacgaag atcaaggtta tgttcttgat     300
gaggatcaag attatgctct tgaagaagat gtaccattat ttcttgatga agatgtacca     360
ttattaccaa gtgtcaagct tccaattgtt gagaagctac cacgatccat tacatgggtc     420
ttcaccaaaa gtagccagct gatggctgaa agtgattctg tgattggtaa agacaaaatc     480
tattatttga atggtgaggc actagaattg agcagtgaag aagatgagga agatgaagaa     540
gaagatgagg aagaaatcaa gaaagaaaaa tgcgaatttt ctgaagatgt agaccgattt     600
atatggacgg ttgggcagga ctatggtttg gatgatctgg tcgtgcggcg tgctctcgcc     660
aagtacctcg aagtggatgt ttcggacata ttggaaagat acaatgaact caagcttaag     720
aatgatggaa ctgctggtga ggcttctgat ttgacatcca agacaataac tactgctttc     780
caggattttg ctgatagacg tcattgccgt cgttgcatga tattcgattg tcatatgcat     840
gagaagtatg agcccgagtc tagatccagc gaagacaaat ctagtttgtt tgaggatgaa     900
gatagacaac catgcagtga gcattgttac ctcaaggtca ggagtgtgac agaagctgat     960
catgtgatgg ataatgataa ctctatatca aacaagattg tggtctcaga tccaaacaac    1020
actatgtgga cgcctgtaga gaaggatctt tacttgaaag gaattgagat atttggagaa    1080
aacagttgtg atgttgcatt aaacatactt cgggggctta gacgtgcct agagatttac    1140
```

```
aattacatgc gcgaacaaga tcaatgtact atgtcattag accttaacaa aactacacaa    1200
agacacaatc aggttaccaa aaaagtatct cgaaaaagta gtaggtcggt ccgcaaaaaa    1260
tcgagactcc gaaaatatgc tcgttatccg cctgctttaa agaaaacaac tagtggagaa    1320
gctaagtttt ataagcacta cacaccatgc acttgcaagt caaaatgtgg acagcaatgc    1380
ccttgtttaa ctcacgaaaa ttgctgcgag aaatattgcg ggtgctcaaa ggattgcaac    1440
aatcgctttg gaggatgtaa ttgtgcaatt ggccaatgca caaatcgaca atgtccttgt    1500
tttgctgcta atcgtgaatg cgatccagat ctttgtcgga gttgtcctct agctgtgga    1560 gatggcactc ttggtgagac accagtgcaa atccaatgca gaacatgca attcctcctt    1620 caaaccaata aaaagattct cattggaaag tctgatgttc atggatgggg tgcatttaca    1680
tgggactctc ttaaaaagaa tgagtatctc ggagaatata ctggagaact gatcactcat    1740
gatgaagcta atgagcgtgg gagaatagaa gatcggattg gttcttccta cctctttacc    1800
ttgaatgatc agctcgaaat cgatgctcgc cgtaaaggaa acgagttcaa atttctcaat    1860
cactcagcaa gacctaactg ctacgccaag ttgatgattg tgagaggaga tcagaggatt    1920
ggtctatttg cggagagagc aatcgaagaa ggtgaggagc ttttcttcga ctactgctat    1980
ggaccagaac atgcggattg gtcgcgtggt cgagaaccta aaagactgg tgcttctaaa    2040 aggtctaagg aagcccgtcc agctcgtgga tcccccggag gtggaggtgg aggtggaggt    2100
ggaggtggag gtggaggtgg aatgaggaca catatagagg gtcatgaaga gctggatgca    2160
gcaagtttgc gtgaacatga agagttcacg aaagtgaaga acatatcaac aattgagctt    2220
ggaaaatatg agattgagac ttggtacttc tcccctttc cgccagaata caatgactgt    2280
gtgaagctct tttttgtga gttttgcctg aacttcatga acgcaaaga gcagcttcaa    2340 aggcatatga graagtgtga cctgaagcac ccacctggtg atgaaattta ccgaagtggt    2400
accttgtcaa tgtttgaggt agatggcaaa agaacaagg tttatgcaca gaatctctgc    2460
tacctggcaa agttatttct tgaccacaaa actctttact acgatgttga tttgtttcta    2520
ttctacgttc tttgcgaatg tgatgaccga ggatgccaca tggttgggta cttttcaaag    2580
gagaagcatt cggaagaagc atacaactta gcttgcattc taaccctgcc ttcatatcaa    2640
agaaaaggct atggaaagtt cttaatagcc ttttcctatg aactgtcaaa gaaagaggga    2700
aaagttggga caccggraaa gacccttgtc ggatctaggc ttactaagct acagaggtta    2760
ttggactcgt gttctattag aaatcttgaa aaaacataa                           2799
```

<210> SEQ ID NO 17

<400> SEQUENCE: 17

000

<210> SEQ ID NO 18
<211> LENGTH: 226
<212> TYPE: PRT
<213> ORGANISM: Artificial Sequence
<220> FEATURE:
<223> OTHER INFORMATION: Description of Artificial Sequence:
      GAL4-UAS-VP16 transcription activator

<400> SEQUENCE: 18

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

```
Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Glu Glu Ser Ser Asn Lys Gly Gln Arg Gln Leu
        130                 135                 140

Thr Val Ser Thr Ala Pro Pro Thr Asp Val Ser Leu Gly Asp Glu Leu
145                 150                 155                 160

His Leu Asp Gly Glu Asp Val Ala Met Ala His Ala Asp Ala Leu Asp
                165                 170                 175

Asp Phe Asp Leu Asp Met Leu Gly Asp Gly Asp Ser Pro Gly Pro Gly
                180                 185                 190

Phe Thr Pro His Asp Ser Ala Pro Tyr Gly Ala Leu Asp Met Ala Asp
                195                 200                 205

Phe Glu Phe Glu Gln Met Phe Thr Asp Ala Leu Gly Ile Asp Glu Tyr
            210                 215                 220

Gly Gly
225

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence:exemplary
      SET domain

<400> SEQUENCE: 19

Ser Asp Val His Gly Trp Gly Ala Phe Thr Trp Asp Ser Leu Lys Lys
  1               5                  10                  15

Asn Glu Tyr Leu Gly Glu Tyr Thr Gly Glu Leu Ile Thr His Asp Glu
                 20                  25                  30

Ala Asn Glu Arg Gly Arg Ile Glu Asp Arg Ile Gly Ser Ser Tyr Leu
             35                  40                  45

Phe Thr Leu Asn Asp Gln Leu Glu Ile Asp Ala Arg Arg Lys Gly Asn
 50                  55                  60

Glu Phe Lys Phe Leu Asn His Ser Ala Arg Pro Asn Cys Tyr Ala Lys
 65                  70                  75                  80

Leu Met Ile Val Arg Gly Asp Gln Arg Ile Gly Leu Phe Ala Glu Arg
                 85                  90                  95

Ala Ile Glu Glu Gly Glu Glu Leu Phe Phe Asp Tyr Cys Tyr Gly Pro
            100                 105                 110

Glu His Ala
        115

<210> SEQ ID NO 20
<211> LENGTH: 6
<212> TYPE: PRT
```

```
<213> ORGANISM: Artificial Sequence
<220> FEATURE:
<223> OTHER INFORMATION: Description of Artificial Sequence:linker
      sequence

<400> SEQUENCE: 20

Gly Gly Gly Gly Gly Gly
  1               5

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:primer
      FIE-Sal

<400> SEQUENCE: 21
atgtcgacga gagtcagaca gagagagag                                        29

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:primer
      FIE-NcoI

<400> SEQUENCE: 22
caccatggct ccgccacctc cgccacccct tggtaatcacg tcccagcg                  48

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence:primer
      FIE-Sph

<400> SEQUENCE: 23
ttcctataag aggcatgcga ggaagcgagc aagtacaca                             39

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:primer
      FIE-SalRV

<400> SEQUENCE: 24
tctgactctc gtcgactaat ctaagctcac aagtctctca                            40

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:primer
      579dXba

<400> SEQUENCE: 25
cattactgcc attggtgtat ctcttattat cta                                   33

<210> SEQ ID NO 26
<211> LENGTH: 23
<212> TYPE: DNA
```

-continued

```
<213> ORGANISM: Artificial Sequence
<220> FEATURE:
<223> OTHER INFORMATION: Description of Artificial Sequence:primer 48S4

<400> SEQUENCE: 26
cactgttgac gtcaatgact cgg                                         23

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:primer
      FIE-RTf

<400> SEQUENCE: 27
ctgtaatcag gcaaacagcc                                             20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:primer
      GFP274r

<400> SEQUENCE: 28
gcatggcgga cttgaaga                                               18

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:APETALA1
      (AP1) gene-specific primer AP1500f

<400> SEQUENCE: 29
gatgatataa gaacatcgaa catttgcca                                   29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence:APETALA1
      (AP1) gene-specific primer AP1991r

<400> SEQUENCE: 30
gatgatataa gaacatcgaa catttgcca                                   29

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:LEAFY (LFY)
      gene-specific primer LFY4042f

<400> SEQUENCE: 31
gctaaagacc gtggcgaa                                               18

<210> SEQ ID NO 32
<211> LENGTH: 18
<212> TYPE: DNA
<213> ORGANISM: Artificial Sequence
<220> FEATURE:
```

```
<223> OTHER INFORMATION: Description of Artificial Sequence:LEAFY (LFY)
      gene-specific primer LFY5371r

<400> SEQUENCE: 32
gcatccacca cgtccaga                                                   18

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:AGAMOUS (AG)
      gene-specific primer 5523f

<400> SEQUENCE: 33
gttgatttgc ataacgataa ccaga                                           25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:AGAMOUS (AG)
      gene-specific primer AG6116r

<400> SEQUENCE: 34
ttcactgata caacattcat gggat                                           25

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:PISTILLATA
      (PI) gene-specific primer PI1500f

<400> SEQUENCE: 35
cacgccattg aacatggcct                                                 20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:PISTILLATA
      (PI) gene-specific primer PI2020r

<400> SEQUENCE: 36
tcgatgatca atcgatgacc aa                                              22

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:actin
      gene-specific primer ACT.conf

<400> SEQUENCE: 37
gatttggcat cacactttct acaatg                                          26

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:actin
```

-continued gene-specific primer ACT.conr

<400> SEQUENCE: 38
gttccaccac tgagcacaat g                                       21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:primer PKf

<400> SEQUENCE: 39
cttcaccaca tgggtcaca                                          19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:primer PKr2

<400> SEQUENCE: 40
ctaaaccgga aggaatgga                                          19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:primer APGf

<400> SEQUENCE: 41
cttgtgtctc tggttgatca                                         20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:primer APGr2

<400> SEQUENCE: 42
ctctgtgttt gcttggagga                                         20

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence:intervening
      peptide spacer

<400> SEQUENCE: 43

Gly Gly Gly Gly Gly Gly Gly Gly Gly Gly Gly Gly Gly Gly Gly
 1               5                  10                  15

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence:oligo(dT)-18
      primer, oligo dTV

<400> SEQUENCE: 44
tttttttttt tttttttv                                                    19

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence:hP/CAF and
      hGCN5 GCN5 family peptide, GCN5 family HAT
      functional domain consensus sequence

<400> SEQUENCE: 45

Leu Ala Leu Ile Lys Asp Gly Arg Val Ile Gly Gly Ile Cys Phe
 1               5                  10                  15

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence:hP/CAF and
      hGCN5 GCN5 family peptide

<400> SEQUENCE: 46

Gly Phe Thr Glu Ile Val Phe Cys Ala Val Thr Ser Asn Glu Gln Val
 1               5                  10                  15

Lys Gly Tyr Gly Thr His Leu Met Asn His Leu Lys Glu Tyr His Ile
             20                  25                  30

Lys His Asn
         35

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence:hP/CAF GCN5
      family peptide

<400> SEQUENCE: 47

Leu Thr Tyr Ala Asp Glu Tyr Ala Ile Gly Tyr Phe Lys Lys Gln Gly
 1               5                  10                  15

Phe Ser Lys Asp Ile
             20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence:hGCN5 GCN5
      family peptide

<400> SEQUENCE: 48

Leu Thr Tyr Ala Asp Glu Tyr Ala Ile Gly Tyr Phe Ile Lys Lys Gln
 1               5                  10                  15

Gly Phe Ser Lys Asp Ile
             20

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence:yGcn5p GCN5
      family peptide

```
<400> SEQUENCE: 49

Ala Val Ile Arg Lys Pro Leu Thr Val Val Gly Gly Ile Thr Tyr
1               5                   10                  15

<210> SEQ ID NO 50
<211> LENGTH: 35
<212> TYPE: PRT
<213> ORGANISM: Artificial Sequence
<220> FEATURE:
<223> OTHER INFORMATION: Description of Artificial Sequence:yGcn5p GCN5
      family peptide

<400> SEQUENCE: 50

Glu Phe Ala Glu Ile Val Phe Cys Ala Ile Ser Ser Thr Glu Gln Val
1               5                   10                  15

Arg Gly Tyr Gly Ala His Leu Met Asn His Leu Lys Asp Tyr Val Arg
            20                  25                  30

Asn Thr Ser
        35

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence:yGcn5p GCN5
      family peptide

<400> SEQUENCE: 51

Leu Thr Tyr Ala Asp Asn Tyr Ala Ile Gly Tyr Phe Lys Lys Gln Gly
1               5                   10                  15

Phe Thr Lys Glu Ile
            20

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence:tHatA GCN5
      family peptide

<400> SEQUENCE: 52

Val Ile Leu Lys Asn Lys Gln Lys Val Ile Gly Gly Ile Cys Phe
1               5                   10                  15

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence:tHatA GCN5
      family peptide

<400> SEQUENCE: 53

Arg Phe Ala Glu Val Ala Phe Leu Ala Val Thr Ala Asn Glu Gln Val
1               5                   10                  15

Arg Gly Tyr Gly Thr Arg Leu Met Asn Lys Phe Lys Asp His Met Gln
            20                  25                  30

Lys Gln Asn
        35

<210> SEQ ID NO 54
```

```
<211> LENGTH: 21
<212> TYPE: PRT
<213> ORGANISM: Artificial Sequence
<220> FEATURE:
<223> OTHER INFORMATION: Description of Artificial Sequence:tHatA GCN5
      family peptide

<400> SEQUENCE: 54

Leu Thr Tyr Ala Asp Asn Phe Ala Ile Gly Tyr Phe Lys Lys Gln Gly
 1               5                  10                  15

Phe Thr Lys Glu His
            20

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 55

Glu Ile Val Phe Cys Ala Val Thr Ser Asn Glu Gln Val Lys Gly Tyr
 1               5                  10                  15

Gly Thr His Leu Met Asn His Leu Lys Glu Tyr His Ile Lys His Asn
            20                  25                  30

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 56

Leu Thr Tyr Ala Asp
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 57

Tyr Ala Ile Gly Tyr Phe
 1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 58

Lys Lys Gln Gly Phe Ser Lys Glu Ile
 1               5

<210> SEQ ID NO 59
<211> LENGTH: 69
<212> TYPE: PRT
<213> ORGANISM: Artificial Sequence
```

```
<220> FEATURE:
<223> OTHER INFORMATION: Description of Artificial Sequence:ySas2 SAS
      (aka MYST) family peptide

<400> SEQUENCE: 59

Ser Thr Lys Pro Met Gly Phe Phe Ser Lys Asp Leu Val Ser Tyr Gln
 1               5                  10                  15

Gln Asn Asn Leu Ala Cys Ile Leu Ile Phe Pro Pro Tyr Gln Arg Arg
             20                  25                  30

Gly Leu Gly Leu Leu Leu Ile Glu Phe Ser Tyr Lys Leu Ser Gln Leu
         35                  40                  45

Glu Gly Val Ile Ser Gly Pro Glu Val Pro Leu Ser Pro Phe Gly Leu
     50                  55                  60

Ile Gly Tyr Leu Lys
 65

<210> SEQ ID NO 60
<211> LENGTH: 71
<212> TYPE: PRT
<213> ORGANISM: Artificial Sequence
<220> FEATURE:
<223> OTHER INFORMATION: Description of Artificial Sequence:hTIP60 SAS
      (aka MYST) family peptide

<400> SEQUENCE: 60

Cys Lys Gly Phe His Ile Val Gly Tyr Phe Ser Lys Glu Lys Glu Ser
 1               5                  10                  15

Thr Glu Asp Tyr Asn Val Ala Cys Ile Leu Thr Leu Pro Pro Tyr Gln
             20                  25                  30

Arg Arg Gly Tyr Gly Lys Leu Leu Ile Glu Phe Ser Tyr Glu Leu Ser
         35                  40                  45

Lys Val Glu Gly Lys Thr Gly Thr Pro Glu Lys Pro Leu Ser Asp Leu
     50                  55                  60

Gly Leu Leu Ser Tyr Arg Ser
 65                  70

<210> SEQ ID NO 61
<211> LENGTH: 70
<212> TYPE: PRT
<213> ORGANISM: Artificial Sequence
<220> FEATURE:
<223> OTHER INFORMATION: Description of Artificial Sequence:dmMOF SAS
      (aka MYST) family peptide

<400> SEQUENCE: 61

Glu Gly Ser His Ile Val Gly Tyr Phe Ser Lys Glu Lys Ser Leu
 1               5                  10                  15

Glu Asn Tyr Asn Val Ala Cys Ile Leu Val Leu Pro Pro His Gln Arg
             20                  25                  30

Lys Gly Phe Gly Lys Leu Leu Ile Ala Phe Ser Tyr Glu Leu Ser Arg
         35                  40                  45

Lys Glu Gly Val Ile Gly Ser Pro Glu Lys Pro Leu Ser Asp Leu Gly
     50                  55                  60

Arg Leu Ser Tyr Arg Ser
 65                  70

<210> SEQ ID NO 62
<211> LENGTH: 71
<212> TYPE: PRT
<213> ORGANISM: Artificial Sequence
<220> FEATURE:
```

-continued

<223> OTHER INFORMATION: Description of Artificial Sequence:yMof SAS
      (aka MYST) family peptide

<400> SEQUENCE: 62

Glu Leu Gly His His Leu Val Gly Tyr Phe Ser Lys Glu Lys Glu Ser
 1               5                  10                  15

Ala Asp Gly Tyr Asn Val Ala Cys Ile Leu Thr Leu Pro Gln Tyr Gln
            20                  25                  30

Arg Met Gly Tyr Gly Lys Leu Leu Ile Glu Phe Ser Tyr Glu Leu Ser
        35                  40                  45

Lys Lys Glu Asn Lys Val Gly Ser Pro Glu Lys Pro Leu Ser Asp Leu
    50                  55                  60

Gly Leu Leu Ser Tyr Arg Ala
65                  70

<210> SEQ ID NO 63
<211> LENGTH: 71
<212> TYPE: PRT
<213> ORGANISM: Artificial Sequence
<220> FEATURE:
<223> OTHER INFORMATION: Description of Artificial Sequence:spYD6D SAS
      (aka MYST) family peptide

<400> SEQUENCE: 63

Gly Gln Glu Cys Lys Val Ile Gly Tyr Phe Ser Lys Glu Lys Arg Ser
 1               5                  10                  15

Ala Ser Asp Tyr Asn Val Ser Cys Ile Leu Thr Leu Pro Ile Tyr Gln
            20                  25                  30

Arg Arg Gly Tyr Gly Val Phe Leu Ile Asp Phe Ser Tyr Leu Leu Thr
        35                  40                  45

Gln Val Glu Gly Lys Leu Gly Ser Pro Glu Lys Pro Leu Ser Asp Leu
    50                  55                  60

Gly Leu Val Thr Tyr Arg Ser
65                  70

<210> SEQ ID NO 64
<211> LENGTH: 71
<212> TYPE: PRT
<213> ORGANISM: Artificial Sequence
<220> FEATURE:
<223> OTHER INFORMATION: Description of Artificial Sequence:hMOZ SAS
      (aka MYST) family peptide

<400> SEQUENCE: 64

Val Lys Gly Cys His Leu Val Gly Tyr Phe Ser Lys Glu Lys His Cys
 1               5                  10                  15

Gln Gln Lys Tyr Asn Val Ser Cys Ile Met Ile Leu Pro Gln Tyr Gln
            20                  25                  30

Arg Lys Gly Tyr Gly Arg Phe Leu Ile Asp Phe Ser Tyr Leu Leu Ser
        35                  40                  45

Lys Arg Glu Gly Gln Ala Gly Ser Pro Glu Lys Pro Leu Ser Asp Leu
    50                  55                  60

Gly Arg Leu Ser Tyr Met Ala
65                  70

<210> SEQ ID NO 65
<211> LENGTH: 71
<212> TYPE: PRT
<213> ORGANISM: Artificial Sequence
<220> FEATURE:
<223> OTHER INFORMATION: Description of Artificial Sequence:ySas3 SAS (aka MYST) family peptide

<400> SEQUENCE: 65

Ala Ala Lys Phe His Phe Val Gly Tyr Phe Ser Lys Glu Lys Phe Asn
1               5                   10                  15

Ser Asn Asp Tyr Asn Leu Ser Cys Ile Leu Thr Leu Pro Ile Tyr Gln
            20                  25                  30

Arg Lys Gly Tyr Gly Gln Phe Leu Met Glu Phe Ser Tyr Leu Leu Ser
        35                  40                  45

Arg Lys Glu Ser Lys Phe Gly Thr Pro Glu Lys Pro Leu Ser Asp Leu
    50                  55                  60

Gly Leu Leu Thr Tyr Arg Thr
65                  70

<210> SEQ ID NO 66
<211> LENGTH: 71
<212> TYPE: PRT
<213> ORGANISM: Artificial Sequence
<220> FEATURE:
<223> OTHER INFORMATION: Description of Artificial Sequence:
      ceR07B5.8 SAS (aka MYST) family peptide

<400> SEQUENCE: 66

Asp Ile Gly Cys His Phe Ala Gly Tyr Phe Ser Lys Glu Lys Tyr Glu
1               5                   10                  15

Pro Asp Val Asn Asn Leu Ser Cys Ile Met Thr Leu Pro Cys Tyr Gln
            20                  25                  30

Glu Met Gly Leu Gly Arg Phe Leu Ile Asp Ile Ser Tyr Ala Leu Ser
        35                  40                  45

Arg Lys Glu Lys Trp Phe Gly Gly Pro Glu Gln Pro Leu Ser Glu Leu
    50                  55                  60

Gly Arg Lys Ala Tyr Gly Gly
65                  70

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 67

His Ile Val Gly Tyr Phe Ser Lys Glu Lys
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 68

Cys Ile Leu Thr Leu Pro
1               5

<210> SEQ ID NO 69
<211> LENGTH: 8
<212> TYPE: PRT
<213> ORGANISM: Artificial Sequence
<220> FEATURE:

-continued

```
<223> OTHER INFORMATION: Description of Artificial Sequence:consensus
      HAT functional domain sequence

<400> SEQUENCE: 69

Tyr Gln Arg Arg Gly Tyr Gly Lys
  1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 70

Leu Ile Glu Phe Ser Tyr
  1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 71

Leu Ser Lys Lys Glu Gly
  1               5

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 72

Gly Thr Pro Glu Lys Pro Leu Ser Asp Leu Gly Leu Leu Ser Tyr Arg
  1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence:yKL087
      peptide

<400> SEQUENCE: 73

Tyr Glu Pro Asp Lys Lys Asp Ile Leu Ile Gly Leu Leu Arg Leu
  1               5                  10                  15

<210> SEQ ID NO 74
<211> LENGTH: 35
<212> TYPE: PRT
<213> ORGANISM: Artificial Sequence
<220> FEATURE:
<223> OTHER INFORMATION: Description of Artificial Sequence:yKL087
      peptide

<400> SEQUENCE: 74

Gly Ser Val Val Pro Leu His Ser Arg Asp Pro Arg Lys Phe Gln His
  1               5                  10                  15

Gln Gly Phe Gly Thr Leu Leu Met Glu Glu Ala Glu Arg Ile Ala Lys
```

-continued

```
                    20                  25                  30
Glu Glu His
        35

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence:yKL087
      peptide

<400> SEQUENCE: 75

Ser Val Ile Ser Gly Val Gly Val Arg Asn Tyr Tyr Gly Lys Leu Gly
1               5                   10                  15

Tyr Glu Leu Asp Gly
            20

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence:yHat1p
      peptide

<400> SEQUENCE: 76

Leu Leu Asn Lys Lys Thr Lys Glu Leu Ile Gly Phe Val Thr Thr
1               5                   10                  15

<210> SEQ ID NO 77
<211> LENGTH: 35
<212> TYPE: PRT
<213> ORGANISM: Artificial Sequence
<220> FEATURE:
<223> OTHER INFORMATION: Description of Artificial Sequence:yHat1p
      peptide

<400> SEQUENCE: 77

Phe Arg Ala Lys Ile Ser Gln Phe Leu Ile Phe Pro Pro Tyr Gln Asn
1               5                   10                  15

Lys Gly His Gly Ser Cys Leu Tyr Glu Ala Ile Ile Gln Ser Trp Leu
            20                  25                  30

Glu Asp Lys
        35

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence:yHat1p
      peptide

<400> SEQUENCE: 78

Asp Asp Leu Arg Asp Arg Asn Asp Ile Gln Arg Leu Arg Lys Leu Gly
1               5                   10                  15

Tyr Asp Ala Val Phe
            20

<210> SEQ ID NO 79
<211> LENGTH: 15
<212> TYPE: PRT
<213> ORGANISM: Artificial Sequence
<220> FEATURE:
```

```
<223> OTHER INFORMATION: Description of Artificial Sequence:yOR109
      peptide

<400> SEQUENCE: 79

His Pro Cys Tyr Glu Leu Lys Lys Leu Leu Ser Asn Gly Ser Phe
 1               5                  10                  15

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence:yOR109
      peptide

<400> SEQUENCE: 80

Tyr Ser Ser Asp Ser Asp Leu Thr Ser Thr Leu Gln His Arg Gly Tyr
 1               5                  10                  15

Gly Gln His Ser Leu Ser Thr Asp Thr Tyr Glu Glu Glu Tyr
            20                  25                  30

<210> SEQ ID NO 81
<211> LENGTH: 34
<212> TYPE: PRT
<213> ORGANISM: Artificial Sequence
<220> FEATURE:
<223> OTHER INFORMATION: Description of Artificial Sequence:YPR193c
      peptide

<400> SEQUENCE: 81

Ile Tyr Ile Asn Asp Leu Tyr Val Asp Glu Asn Ser Arg Val Lys Gly
 1               5                  10                  15

Ala Gly Gly Lys Leu Ile Gln Phe Val Tyr Asp Glu Ala Asp Lys Leu
            20                  25                  30

Gly Thr w<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence:YEH6 peptide

<400> SEQUENCE: 82

Ala Phe Asp Thr Glu Thr Gly Asp Ala Ile Gly Phe Ala His Tyr
 1               5                  10                  15

<210> SEQ ID NO 83
<211> LENGTH: 35
<212> TYPE: PRT
<213> ORGANISM: Artificial Sequence
<220> FEATURE:
<223> OTHER INFORMATION: Description of Artificial Sequence:YEH6 peptide

<400> SEQUENCE: 83

Glu Val Val Tyr Met Asn Asp Leu Tyr Val Thr Glu Arg Ala Arg Val
 1               5                  10                  15

Lys Gly Val Gly Arg Lys Leu Ile Glu Phe Val Tyr Ser Arg Ala Asp
            20                  25                  30

Glu Leu Gly
        35

<210> SEQ ID NO 84
<211> LENGTH: 21
```

```
<212> TYPE: PRT
<213> ORGANISM: Artificial Sequence
<220> FEATURE:
<223> OTHER INFORMATION: Description of Artificial Sequence:YEH6 peptide

<400> SEQUENCE: 84

Thr Asp His Tyr Asn His Arg Ala Gln Leu Leu Tyr Thr Lys Val Ala
1               5                  10                  15

Tyr Lys Thr Asp Lys
            20

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence:YMR069w
      peptide

<400> SEQUENCE: 85

Met Leu Thr Glu Glu Thr Gly Leu Val Glu Gly Asp Ala Leu His Glu
1               5                  10                  15

<210> SEQ ID NO 86
<211> LENGTH: 31
<212> TYPE: PRT
<213> ORGANISM: Artificial Sequence
<220> FEATURE:
<223> OTHER INFORMATION: Description of Artificial Sequence:YMR069w
      peptide

<400> SEQUENCE: 86

Pro Val Ile Tyr Leu Tyr Glu Val His Val Ala Ser Ala His Arg Gly
1               5                  10                  15

His Gly Ile Gly Arg Arg Leu Leu Glu His Ala Leu Cys Asp Gly
            20                  25                  30

<210> SEQ ID NO 87
<211> LENGTH: 33
<212> TYPE: PRT
<213> ORGANISM: Artificial Sequence
<220> FEATURE:
<223> OTHER INFORMATION: Description of Artificial Sequence:ySpt10
      peptide

<400> SEQUENCE: 87

Val Val Thr Gly Thr Phe Leu Val Asn Ala Gly Ile Arg Gly Lys Gly
1               5                  10                  15

Ile Gly Lys Thr Leu Met Glu Thr Phe Ile Glu Trp Ser Lys Lys Leu
            20                  25                  30

Gly

<210> SEQ ID NO 88
<211> LENGTH: 34
<212> TYPE: PRT
<213> ORGANISM: Artificial Sequence
<220> FEATURE:
<223> OTHER INFORMATION: Description of Artificial Sequence:spATS1
      peptide

<400> SEQUENCE: 88

Val Gly Ile Tyr Leu Glu Asp Leu Tyr Val Arg Pro Gln Phe Arg Gly
1               5                  10                  15

Lys Gly Tyr Gly Ser Tyr Leu Leu Ser Tyr Leu Ala Arg Glu Ser Leu
            20                  25                  30
```

-continued

```
Arg Ile

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 89

Val Ile Tyr Ile
  1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 90

Asp Leu Tyr Val
  1

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence:consensus
      HAT functional domain sequence

<400> SEQUENCE: 91

Arg Gly Lys Gly Val Gly Arg Lys Leu Ile Glu Phe Val
  1               5                  10
```